United States Patent
Liu et al.

(10) Patent No.: US 11,498,977 B2
(45) Date of Patent: *Nov. 15, 2022

(54) HETERODIMERIC IMMUNOGLOBULIN CONSTRUCTS AND PREPARATION METHODS THEREOF

(71) Applicant: BEIJING HANMI PHARMACEUTICAL CO., LTD., Beijing (CN)

(72) Inventors: Jiawang Liu, Beijing (CN); Nanmeng Song, Beijing (CN); Dongge Yang, Beijing (CN); Yaping Yang, Beijing (CN); Maengsup Kim, Beijing (CN)

(73) Assignee: BEIJING HANMI PHARMACEUTICAL CO., LTD., Beijing (CN)

(*) Notice: Subject to any disclaimer, the term of this patent is extended or adjusted under 35 U.S.C. 154(b) by 371 days.

This patent is subject to a terminal disclaimer.

(21) Appl. No.: 16/337,854

(22) PCT Filed: Sep. 28, 2017

(86) PCT No.: PCT/CN2017/104044
§ 371 (c)(1),
(2) Date: Mar. 28, 2019

(87) PCT Pub. No.: WO2018/059502
PCT Pub. Date: Apr. 5, 2018

(65) Prior Publication Data
US 2019/0284299 A1 Sep. 19, 2019

(30) Foreign Application Priority Data
Sep. 29, 2016 (CN) .......................... 201610863814.7

(51) Int. Cl.
| | |
|---|---|
| C07K 16/32 | (2006.01) |
| A61P 35/00 | (2006.01) |
| C07K 16/28 | (2006.01) |
| C07K 16/30 | (2006.01) |
| A61P 37/02 | (2006.01) |
| C07K 16/46 | (2006.01) |
| A61K 39/00 | (2006.01) |

(52) U.S. Cl.
CPC .............. *C07K 16/32* (2013.01); *A61P 35/00* (2018.01); *A61P 37/02* (2018.01); *C07K 16/2809* (2013.01); *C07K 16/2827* (2013.01); *C07K 16/2887* (2013.01); *C07K 16/30* (2013.01); *C07K 16/468* (2013.01); *A61K 2039/505* (2013.01); *C07K 2317/31* (2013.01); *C07K 2317/52* (2013.01); *C07K 2317/526* (2013.01); *C07K 2317/622* (2013.01); *C07K 2317/64* (2013.01); *C07K 2317/66* (2013.01); *C07K 2317/73* (2013.01); *C07K 2317/92* (2013.01); *C07K 2317/94* (2013.01)

(58) Field of Classification Search
CPC .......... C07K 2317/31; C07K 2317/526; C07K 2317/94; C07K 2317/90
USPC ............................................. 424/133.1, 135.3
See application file for complete search history.

(56) References Cited

U.S. PATENT DOCUMENTS

| | | |
|---|---|---|
| 5,173,168 A | 12/1992 | van Haastrecht et al. |
| 5,731,168 A | 3/1998 | Carter et al. |
| 5,869,046 A | 2/1999 | Presta et al. |
| 8,354,509 B2 | 1/2013 | Carven et al. |
| 9,562,109 B2 | 2/2017 | Von Kreudenstein et al. |
| 9,574,010 B2 | 2/2017 | Spreter Von Kreudenstein et al. |
| 9,732,155 B2 | 8/2017 | Spreter Von Kreudenstein et al. |
| 9,758,805 B2 | 9/2017 | De Kruif et al. |
| 9,914,785 B2 | 3/2018 | Corper et al. |
| 9,988,460 B2 | 6/2018 | Spreter Von Kreudenstein et al. |
| 10,344,050 B2 | 7/2019 | Gramer et al. |
| 2006/0074225 A1 | 4/2006 | Chamberlain et al. |
| 2006/0280747 A1 | 12/2006 | Fuh et al. |
| 2013/0195849 A1 | 8/2013 | Spreter Von Kreudenstein et al. |
| 2013/0336981 A1 | 12/2013 | De Kruif et al. |
| 2015/0203579 A1 | 7/2015 | Papadopoulos et al. |
| 2015/0210769 A1 | 7/2015 | Freeman et al. |
| 2016/0193334 A1 | 7/2016 | Strack et al. |
| 2019/0010232 A1 | 1/2019 | Kalos et al. |
| 2019/0367633 A1* | 12/2019 | Liu ................ C07K 16/2818 |
| 2020/0299412 A1* | 9/2020 | Liu ........................ A61P 35/00 |
| 2021/0032343 A1* | 2/2021 | Liu ........................ A61P 35/00 |
| 2021/0040193 A1* | 2/2021 | Yang ..................... C07K 16/32 |
| 2021/0230277 A1* | 7/2021 | Liu ..................... C07K 16/468 |
| 2022/0010006 A1* | 1/2022 | Liu ..................... C07K 14/525 |

FOREIGN PATENT DOCUMENTS

| | | |
|---|---|---|
| CN | 1299370 A | 6/2001 |
| CN | 103429620 A | 12/2013 |
| CN | 104080811 A | 10/2014 |
| CN | 104114579 A | 10/2014 |
| CN | 104520320 A | 4/2015 |
| CN | 105111314 A | 12/2015 |
| CN | 105175545 A | 12/2015 |
| CN | 105828837 A | 8/2016 |
| CN | 106883297 A | 6/2017 |
| CN | 107325184 A | 11/2017 |

(Continued)

OTHER PUBLICATIONS

Atwell et al (J. Molec. Biol. 270:26-35 (1997)).*
Camilla De Nardis et al., "A new approach for generating bispecific antibodies based on a common light chain format and the stable architecture of human immunoglobulin G1", J. Biol. Chem., 2017, vol. 292, No. 35, pp. 14706-14717 (12 pages total).

(Continued)

*Primary Examiner* — Lynn A Bristol
(74) *Attorney, Agent, or Firm* — Sughrue Mion, PLLC

(57) ABSTRACT

The present invention provides a method for production of stable and highly specific heterodimeric immunoglobulin constructs, e.g., bispecific antibodies, retaining desirable properties of native IgG and lacking undesirable heavy chain-light chain mispairing, that can simultaneously bind two target molecules and are more potent in the treatment of complex diseases.

37 Claims, 33 Drawing Sheets
Specification includes a Sequence Listing.

(56) References Cited

FOREIGN PATENT DOCUMENTS

| | | |
|---|---|---|
| EP | 3 533 804 A1 | 9/2019 |
| JP | 2010-530753 A | 9/2010 |
| JP | 2014-530891 A | 11/2014 |
| JP | 2014-533243 A | 12/2014 |
| JP | 2016-508117 A | 3/2016 |
| WO | 96/27011 A1 | 9/1996 |
| WO | 99/57134 A1 | 11/1999 |
| WO | 2009089004 A1 | 7/2009 |
| WO | 2010/121766 A1 | 10/2010 |
| WO | 2011/063348 A1 | 5/2011 |
| WO | 2012/058768 A1 | 5/2012 |
| WO | 2012/131555 A2 | 10/2012 |
| WO | 2012/145493 A1 | 10/2012 |
| WO | 2013/063702 A1 | 5/2013 |
| WO | 2013060867 A2 | 5/2013 |
| WO | 2013/157953 A1 | 10/2013 |
| WO | 2013/157954 A1 | 10/2013 |
| WO | 2014/049003 A1 | 4/2014 |
| WO | 2014/067011 A1 | 5/2014 |
| WO | 2014/087248 A2 | 6/2014 |
| WO | 2015/095404 A2 | 6/2015 |
| WO | 2015/095412 A1 | 6/2015 |
| WO | 2015/095418 A1 | 6/2015 |
| WO | 2016/024021 A1 | 2/2016 |
| WO | 2016/057933 A1 | 4/2016 |
| WO | 2016/109415 A1 | 7/2016 |
| WO | 2016/115274 A1 | 7/2016 |
| WO | 2016/170039 A1 | 10/2016 |
| WO | 2016/201051 A1 | 12/2016 |
| WO | 2017/101828 A1 | 6/2017 |
| WO | 2017/117179 A1 | 7/2017 |
| WO | 2017/167919 A1 | 10/2017 |
| WO | 2018/002339 A1 | 1/2018 |
| WO | 3018/068336 A1 | 4/2018 |
| WO | 2018/090950 A1 | 5/2018 |
| WO | 2019/068302 A1 | 4/2019 |

OTHER PUBLICATIONS

International Search Report for PCT/CN2017/104044 dated Jan. 8, 2018 [PCT/ISA/210].
Written Opinion for PCT/CN2017/104044 dated Jan. 8, 2018 [PCT/ISA/237].
Sokolosky, Jonathan, et al., "The neonatal Fc receptor, FcRn, as a target for drug delivery and therapy", Advanced Drug Delivery Reviews, 2014, pp. 1-16.
Stapleton, Nigel, et al.,"The multiple facets of FcRn in immunity", Immunological Reviews, 2015, vol. 268, pp. 253-268.
Pyzik, Michal, et al., "FcRn: The Architect Behind the Immune and Nonimmune Functions of IgG and Albumin", The Journal of Immunology, vol. 194, 2015, pp. 4595-4603 (10 pages).
Ward, E. Sally, et al., "Targeting FcRn for the modulation of antibody dynamics", Molecular Immunology, 2015, pp. 1-11.
Roopenian, Derry, et al., " FcRn: the neonatal Fc receptor comes of age", Nature Reviews Immunology, vol. 7, 2007, pp. 715-725.
Ecuadorean Intellectual Property Office; Communication dated Oct. 8, 2019 issued in counterpart application No. SENADI-2019-22190.
Anja Loffler, et al., "A recombinant bispecific single-chain antibody, CD19 x CD3, induces rapid and high Lymphoma-directed cytotoxicity by unstimulated T lymphocytes", Blood, Mar. 15, 2000, pp. 2098-2103, vol. 95, No. 6.
Ashley Mentlik James, et al., "Combination immune therapies to enhance anti-tumor responses by NK cells", Frontiers in Immunology, Dec. 23, 2013, 12 pages, vol. 4.
Christopher Wright, et al., "Expression of c-erbB-2 Oncoprotein: A Prognostic Indicator in Himan Breast Cancer", Cancer Research, Apr. 15, 1989, pp. 2087-2090, vol. 49.
Cornelia Haas, et al., "Mode of cytotoxic action of T cell-engaging BiTE antibody MT110", Imnmunobiology, 2009, pp. 441-453, vol. 214.
Dennis J. Slamon, et al., "Human Breast Cancer: Correlation of Relapse and Survival with Amplification of the HER-2/neu Oncogene", Science, Jan. 9, 1987, pp. 177-182, vol. 235.
DJ Slamon, et al., "Use of chemotherapy plus a monoclonal antibody against HER2 for metastatic breast cancer that overexpresses HER2", New England Journal of Medicine, Mar. 15, 2001, 4 pages, 783-792, vol. 344, No. 11.
Drew M. Pardoll, "The blockade of immune checkpoints in cancer immunotherapy", Nature, Apr. 2012, pp. 252-264, vol. 12.
Elena Gianchecci, et al., "Recent insights into the role of the PD-1/PD-L1 pathway in immunological tolerance and autoimmunity", Autoimmunity Reviews, 2013, pp. 1091-1100, vol. 12.
F. Revillion, et al., "ERBB2 Oncogene in Human Breast Cancer and its Clinical Significance", European Journal of Cancer, 1998, pp. 791-808, vol. 34, No. 6.
Greg T. Motz, et al., "Deciphering and Reversing Tumor Immune Suppression", Immunity Review, Jul. 25, 2013, pp. 61-73, vol. 39.
Hye-Ji Choi, et al., "A Heterodimeric Fc-Based Bispecific Antibody Simultaneously Targeting VEGFR-2 and Met Exhibits Potent Antitumor Activity", Molecular Cancer Therapeutics, Oct. 16, 2013, vol. 12, No. 12, pp. 2748-2759 (14 pages total).
Hye-Ji Choi, et al., "Engineering of Immunoglobulin Fc Heterodimers Using Yeast Surface-Displayed Combinatorial Fc Library Screening", PLOS One, Dec. 16, 2015, vol. 10, No. 12.
International Search Report for PCT/CN2017/111310 dated Feb. 22, 2018 [PCT/ISA/210].
Kim C. Ohaegbulam, et al., "Human cancer immunotherapy with antibodies to the PD-1 and PD-L1 pathway", Trends Mol Med, Jan. 2015, 23 pages, vol. 21, No. 1.
Michael A. Postow, et al., "Immune Checkpoint Blockade in Cancer Therapy", Journal of Clinical Oncology, Jun. 10, 2015, pp. 1974-1982, vol. 33, No. 17.
Michael Jager, et al., Immunomonitoring Results of a Phase II?-III Study of Malignant Ascites Patients Treated with the Trifunctional Antibody Catumaxomab (Anti-EpCAM) x Anti-CD3), Cancer Research, Jan. 1, 2012, pp. 24-32, vol. 72, No. 1.
Sara Pilotto, et al., "Immune Checkpoint Inhibitors for Non-small-cell Lung Cancer: Does that Represent a a 'New Frontier'?", Anti-Cancer Agent in Medicinal Chemistry, 2015, 7 pages, vol. 15, No. 0.
Sehar Afreen, et al., "The immunoinhibitory B7 H1 molecule as a potential target in cancer: Killing many birds with one stone", Hematol Oncol Stem Cell, First Quarter 2014, 17 pages, vol. 7, No. 1.
Gunasekaran K. et al., Enhancing Antibody Fc Heterodimer Formation Through Electrostatic Steering Effects: Applications to Bispecific Molecules and Monovalent IgG, J Biol Chem., Apr. 16, 2010, vol. 285, No. 25, pp. 19637-19646 (10 Pages).
Written Opinion of the International Searching Authority for PCT/IB2019/051008, dated May 29, 2019.
International Search Report for PCT/IB2019/051008 dated May 29, 2019 [PCT/ISA/210].
International Search Report for PCT/CN2018/118800 dated Mar. 4, 2019 [PCT/ISA/210].
Brekken et al., "Selective inhibition of Vascular Endothelial Growth Factor (VEGF) Receptor 2 (KDR/Fik-1) Activity by a Monoclonal Anti-VEGF Antibody Blocks Tumor Growth in Mice", Cancer Research, 60, Sep. 15, 2000, pp. 5117-5124.
Brinkmann, Ulrich, "The making of bispecific antibodies", MABS, vol. 9, No. 2, (Jan. 10, 2017), 182-212.
Bruns et al., "Effect of the Vascular Endothelial Growth Factor Receptor-2 Antibody DC101 Plus Gemcitabine on Growth, Metastasis and Angiogenesis of Human Pancreatic Cancer Growth Orthoropically in Nude Mice", Int. J. Cancer, 2002, 102, pp. 101-108.
Chen et al., "Molecular Pathways: Next Generation Immunotherapy—Inhibiting Programmed Death-Ligand 1 and Programmed Death-1", Clin. Cancer Res., Dec. 15, 2012, 18(24), pp. 6580-6587, 9 pages.
Chen, Lieping, et al., "Anti-PD-1/PD-L1 therapy of human cancer: past, present, and future", The Journal of Clinical Investigation, 125(9), (Sep. 2015), 3384-3391.
Extended European Search Report dated Dec. 7, 2020 in European Application No. 18777419.5.

(56) References Cited

OTHER PUBLICATIONS

Ferrara et al., "The Biology of VEGF and its Receptors", Angiogenesis Focus, Nature Medicine, vol. 9 No. 6, Jun. 2003, pp. 669-676.
Folkman, J., "Angiogenesis: An Organizing Principle for Drug Discovery?", Nature Reviews, Drug Discovery, vol. 6, Apr. 2007, pp. 273-286.
Folkman, J., "Clinical Applications of Research on Angiogenesis", New England Journal of Medicine, Seminars in Medicine of the Beth Israel Hospital, Boston, vol. 333, No. 26, Dec. 28, 1995, pp. 1757-1763.
Gasparini et al., "Clinical Importance of the Determination of Tumor Angiogenesis in Breast Carcinoma: Much More Than a New Prognostic Tool", Journal of Clinical Oncology, vol. 13, No. 3, Mar. 1995, pp. 765-782.
Ha, Ji-Hee, "Immunoglobulin Fc Heterodimer Platform Technology: From Design to Applications in Therapeutic Antibodies and Proteins", Frontiers in Immunology, vol. 7, (Oct. 6, 2016), 1-16.
Hartkopf, Andreas D., et al., "PD-1 and PDL1 immune Checkpoint Blockade to Treat Breast Cancer", Breast Care, vol. 11, No. 6, (Jan. 1, 2016), 385-390.
Henick et al., "The PD-1 Pathway as a Therapeutic Target to Overcome Immune Escape Mechanisms in Cancer" Expert Opin. Ther. Targets, (2014), 18(12), 14 pages.
"IMGT/2Dstructure-DB card for INN 9798", © Copyright 1995-2015 IMGT© [online], [archived on Apr. 25, 2015], Retrieved from the Internet: <URL: www.imgt.org/3Dstructure-DB/cgi/details.Ggi?pdbcode=9798>, (2015), 2 pgs.
International Search Report and Written Opinion for International Application PCT/CN2019/074541, dated Apr. 30, 2019, 24 pages.
International Search Report dated Jun. 21, 2018 in International Application No. PCT/CN2018/080858.
Johnson et al., "Randomized Phase II Trial Comparing Bevacizumab Plus Carboplatin and Paclitaxel With Carboplatin and Paclitaxel Alone in Previously Untreated Locally Advanced or Metastatic Non-Small-Cell Lung Cancer", Journal of Clinical Oncology, vol. 22, No. 11, Jun. 1, 2004, pp. 2184-2191.
Kabbinavar et al., "Phase II, Randomized Trial Comparing Bevacizumab Plus Fluorouracil (FU)/Leucovorin (LV) With FU/LV Alone in Patients with Metastatic Colorectal Cancer", J. Clin. Oncol., vol. 21, No. 1, Jan. 1, 2003, pp. 60-65.
Kim et al., "Prospects for Targeting PD-1 and PD-L1 in Various Tumor Types", Oncology Journal, Nov. 11, 2014 vol. 28, Issue 11, 12 pages.
Kumar et al., "Breast Carcinoma: Vascular Density Determined Using CD105 Antibody Correlates with Tumor Prognosis", Cancer Research, 59, Feb. 15, 1999, pp. 856-861.
Liu Boning, "Construction and anti-tumor effects of a new novel bispecific fusion protein targeting pd-L1 and cd47", South China University of Technology, 122 pages (2016).
Liu et al., "Fc Engineering for Developing Therapeutic Bispecific Antibodies and Novel Scaffolds", Frontiers in Immunology, Jan. 2017, vol. 8, Article 38, 15 pages.
Mellman, I., "The Renaissance of Immunotherapy is a Revolution for Cancer Patients", ASCO, GU 2015, 29 pages.
Shaheen et al., "Inhibited Growth of Colon Cancer Carcinomatosis by Antibodies to Vascular Endothelial and Epidermal Growth Factor Receptors", British Journal of Cancer, (2001), 85(4), pp. 584-589.
Sockolosky et al., "Durable antitumor responses to CD47 blockade require adaptive immune stimulation", PNAS, 113(19): E2646-E2654 (2016).
Tartour et al., "Angiogenesis and Immunity: A Bidirectional Link Potentially Relevant for the Monitoring of Antiangiogenic Therapy and the Development of Novel Therapeutic Combination with Immunotherapy", Cancer Metastasis Rev., (2011), 30, pp. 83-95.
Tischer et al., "The Human Gene for Vascular Endothelial Growth Factor", The Journal of Biological Chemistry, vol. 266, No. 18, Jun. 25, 1991, pp. 11947-11954.
Von Kreudenstein et al., "Improving biophysical properties of a bispecific antibody scaffold to aid developability", mAbs, 5(5): 646-654 (2013).
Written Opinion dated Jun. 21, 2018 in International Application No. PCT/CN2018/080858.
Yasuda et al., "Simultaneous Blockade of Programmed Death 1 and Vascular Endothelial Growth Factor Receptor 2 (VEGFR2) Induces Synergistic Anti-tumour Effect In Vivo", British Society for Immunology, Clinical and Experimental Immunology, 2013, 172, pp. 500-506.
Albanell et al., "Trastuzumab, a humanized anti-HER2 monoclonal antibody, for the treatment of breast cancer", Drugs of Today, vol. 35, No. 12, p. 931, 1999 (1 page total).

* cited by examiner

1. Molecular weight standard
2. purified heterodimer antibody 1      2

1. Molecular weight standard
2. Purified heterodimer antibody 1    2

1. Molecular weight standard
2. Purified heterodimer antibody

1. Molecular weight standard
2. Purified heterodimer antibody

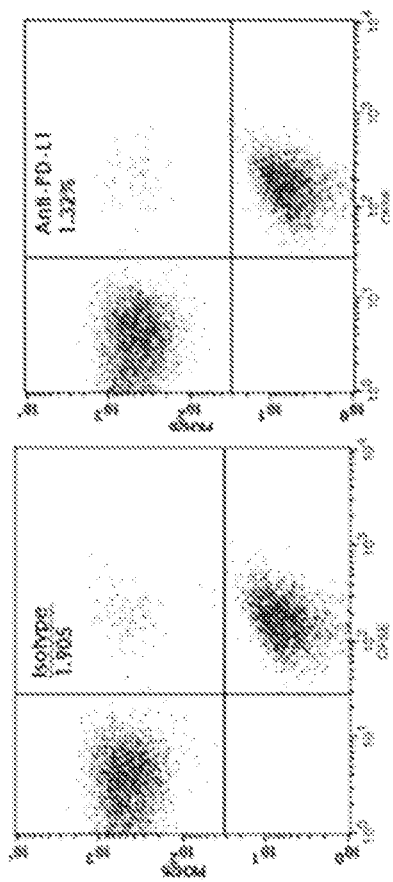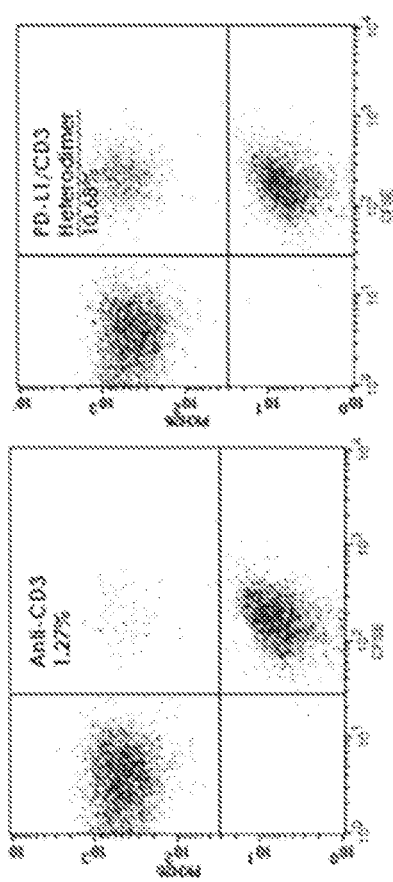
FIG. 22A  FIG. 22B  FIG. 22C  FIG. 22D

1. Air, Day1
2. Air, Day3
3. Air, Day5
4. (L)- dHAA, 0.5mM
5. (L)- dHAA, 1mM
6. (L)- dHAA, 5mM
7. (L)- dHAA, 10mM
8. (L)- dHAA, 5mM, 5hr
9. (L)- dHAA, 5mM, 24hr

1. Molecular weight standard
2. Purified heterodimer antibody

1. CD20-Fc1 homodimer
2. CD20-Fc1 monomer
3. CD20-Fc1+Her2-Fc2 re-oxidized sample
4. Her2-Fc2 monomer
5. Her2-Fc2 homodimer

SEQUENCE LISTING

```
<160> NUMBER OF SEQ ID NOS: 80

<210> SEQ ID NO 1
<211> LENGTH: 22
<212> TYPE: DNA
<213> ORGANISM: Artificial
<220> FEATURE:
<223> OTHER INFORMATION: Synthetic

<400> SEQUENCE: 1
tggggcccag ccggccagat ct                                          22

<210> SEQ ID NO 2
<211> LENGTH: 27
<212> TYPE: DNA
<213> ORGANISM: Artificial
<220> FEATURE:
<223> OTHER INFORMATION: Synthetic

<400> SEQUENCE: 2
ataagaatgc ggccgcgtcg acctgca                                     27

<210> SEQ ID NO 3
<211> LENGTH: 41
<212> TYPE: DNA
<213> ORGANISM: Artificial
```

```
<220> FEATURE:
<223> OTHER INFORMATION: Synthetic

<400> SEQUENCE: 3
atcgagtcaa tattagggtt agtaaaaggg tcctaaggaa c                     41

<210> SEQ ID NO 4
<211> LENGTH: 44
<212> TYPE: DNA
<213> ORGANISM: Artificial
<220> FEATURE:
<223> OTHER INFORMATION: Synthetic

<400> SEQUENCE: 4
cagtcgataa tattaagaat taattctcat gtttgacagc ttat                  44

<210> SEQ ID NO 5
<211> LENGTH: 37
<212> TYPE: DNA
<213> ORGANISM: Artificial
<220> FEATURE:
<223> OTHER INFORMATION: Synthetic

<400> SEQUENCE: 5
tagcctcccc ctagggtggg cgaagaactc cagcatg                          37

<210> SEQ ID NO 6
<211> LENGTH: 49
<212> TYPE: DNA
<213> ORGANISM: Artificial
<220> FEATURE:
<223> OTHER INFORMATION: Synthetic

<400> SEQUENCE: 6
tttggaggcc taggcttttg caaagatcga tcaagagaca ggatgagga             49

<210> SEQ ID NO 7
<211> LENGTH: 2773
<212> TYPE: DNA
<213> ORGANISM: Artificial
<220> FEATURE:
<223> OTHER INFORMATION: Synthetic

<400> SEQUENCE: 7
tgctggggcc cagccggcca tgagcgacag cgaggtgaac caggaggcca aacccgaggt    60
gaagcccgag gtgaaacccg agacccacat caacctgaag gtgagcgacg gcagcagcga   120
gatcttcttc aagatcaaga agaccacccc cctgaggagg ctgatggagg ccttcgccaa   180
gaggcagggc aaggagatgg acagcctgag gttcctgtac gacggcatcc gtattcaagc   240
cgaccagacc cctgaggacc tggacatgga ggacaacgac atcatcgagg cccacaggga   300
gcagatcggc ggcgaaccca gtccagcga taagacccac acatgccctc cctgtcctgc   360
tcccgaactg ctgggaggac cctccgtctt cctgttcccc cccaagccca aagcacact   420 gatgatcagc aggaccctg aagtgacctg cgtggtcgtg gacgtgagcc acgaggaccc   480
cgaggtcaag tttaactggt acgtggacgg cgtggaggtc cacaacgcca agaccaagcc   540
cagggaggag cagtacaaca gcacctacag ggtcgtgtcc gtgctgaccg tgctccacca   600
agattggctc aacggcaagg agtataagtg caaagtcagc aacaaggccc tccccgcccc   660
catcgagaaa accatcagca aggccaaggg ccaaccgcgg gaacctcaag tgtatacccc   720
ccctcccagc cgggatgagc tgaccaagaa ccaagtctcc ctcacctgcc tggtcaaggg   780
```

| | |
|---|---|
| attctaccct tccgacattg ccgtcgaatg ggagagcaat ggccagcccg agaacaacta | 840 |
| caagacaacc cccccgtcc tggatagcga cggatccttc ttcctgtact ccaagctcac | 900 |
| cgtcgacaag agccggtggc aacagggcaa cgtgttctcc tgtagcgtga tgcacgaagc | 960 |
| cctccacaac cactataccc agaagagcct gagcctcagc cccggcaaat gatgaagatc | 1020 |
| tctagagctc gctgatcagc ctcgactgtg ccttctagtt gccagccatc tgttgtttgc | 1080 |
| ccctcccccg tgccttcctt gaccctggaa ggtgccactc ccactgtcct ttcctaataa | 1140 |
| aatgaggaaa ttgcatcgca ttgtctgagt aggtgtcatt ctattctggg gggtggggtg | 1200 |
| gggcaggaca gcaaggggga ggattgggaa gacaatagca ggcatgctgg ggatgcggtg | 1260 |
| ggctctatgg cttctgaggc ggaaagaacc agctggggct ctaggggggta tccccacgcg | 1320 |
| ccctgtagcg cgcagcgcg cgttgacatt gattattgac tagttattaa tagtaatcaa | 1380 |
| ttacggggtc attagttcat agcccatata tggagttccg cgttacataa cttacggtaa | 1440 |
| atggcccgcc tggctgaccg cccaacgacc cccgcccatt gacgtcaata atgacgtatg | 1500 |
| ttcccatagt aacgccaata gggactttcc attgacgtca atgggtggac tatttacggt | 1560 |
| aaactgccca cttggcagta catcaagtgt atcatatgcc aagtacgccc cctattgacg | 1620 |
| tcaatgacgg taaatggccc gcctggcatt atgcccagta catgacccta tgggactttc | 1680 |
| ctacttggca gtacatctac gtattagtca tcgctattac catggtgatg cggttttggc | 1740 |
| agtacatcaa tgggcgtgga tagcggtttg actcacgggg atttccaagt ctccacccca | 1800 |
| ttgacgtcaa tgggagtttg ttttggcacc aaaatcaacg ggactttcca aaatgtcgta | 1860 |
| acaactccgc cccattgacg caaatgggcg gtaggcgtgt acggtgggag gtctatataa | 1920 |
| gcagagctct ctggctaact agagaaccca ctgcttactg gcttatcgaa atgccaccat | 1980 |
| ggagacagac acactcctgc tatgggtact gctgctctgg gttccaggtt ccactggtga | 2040 |
| ctatccatat gatgttccag attatgctga gcccaagtcc agcgacaaga cccacacatg | 2100 |
| ccccccttgt cctgccccctg aactgctcgg aggcccctagc gtgttcctct tccctcccaa | 2160 |
| acccaaggac accctcatga tctccaggac ccctgaggtg acctgcgtcg tggtggacgt | 2220 |
| cagccacgag gaccccgagg tgaagttcaa ctggtacgtg gacggcgtcg aggtccacaa | 2280 |
| cgccaagaca aagcccaggg aggaacagta caacagcacc tacagggtgg tcagcgtgct | 2340 |
| gaccgtgctg caccaggatt ggctcaacgg caaggagtac aagtgcaaag tctccaacaa | 2400 |
| ggccctgccc gcccccatcg agaagaccat ctccaaggct aagggacagc ccagggagcc | 2460 |
| ccaagtgtac accctccctc ccagcccggga tgagctgacc aagaaccaag tctccctcac | 2520 |
| ctgcctggtc aagggattct acccttccga cattgccgtc gaatgggaga gcaatggcca | 2580 |
| gcccgagaac aactacaaga caccccccc cgtcctggat agcgacggat ccttcttcct | 2640 |
| gtactccaag ctcaccgtcg acaagagcag atggcagcag ggcaacgtgt tcagctgtag | 2700 |
| cgtgatgcac gaggccctgc acaaccacta cacccagaag agcctgtccc tcagcccgg | 2760 |
| caagctgcag aat | 2773 |

<210> SEQ ID NO 8
<211> LENGTH: 69
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (41)..(42)
<223> OTHER INFORMATION: n can be a, c, g or t

<400> SEQUENCE: 8
tcccagccgg gatgagctga ccaagaacca agtctccctc nnstgcctgg tcaagggatt    60
ctacccttc                                                           69

<210> SEQ ID NO 9
<211> LENGTH: 66
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (44)..(45)
<223> OTHER INFORMATION: n can be a, c, g or t

<400> SEQUENCE: 9
gtccacggtg agcttggagt acaggaagaa ggatccgtcg ctsnncagga cggggggggt    60
tgtctt                                                              66

<210> SEQ ID NO 10
<211> LENGTH: 27
<212> TYPE: DNA
<213> ORGANISM: Artificial
<220> FEATURE:
<223> OTHER INFORMATION: Synthetic

<400> SEQUENCE: 10
tactccaagc tcaccgtgga caagagc                                       27

<210> SEQ ID NO 11
<211> LENGTH: 52
<212> TYPE: DNA
<213> ORGANISM: Artificial
<220> FEATURE:
<223> OTHER INFORMATION: Synthetic

<400> SEQUENCE: 11
cgatccaatc gatggaagat cttcatcatt tgccggggct gaggctcagg ct           52

<210> SEQ ID NO 12
<211> LENGTH: 70
<212> TYPE: DNA
<213> ORGANISM: Artificial
<220> FEATURE:
<223> OTHER INFORMATION: Synthetic

<400> SEQUENCE: 12
caagggccag ccgcgggaac ctcaagtgta taccctccct cccagccggg atgagctgac    60
caagaaccaa                                                          70

<210> SEQ ID NO 13
<211> LENGTH: 52
<212> TYPE: DNA
<213> ORGANISM: Artificial
<220> FEATURE:
<223> OTHER INFORMATION: Synthetic

<400> SEQUENCE: 13
cgatccaatc gatggaagat cttcatcatt tgccggggct gaggctcagg ct           52

<210> SEQ ID NO 14
<211> LENGTH: 54
<212> TYPE: DNA

<213> ORGANISM: Artificial
<220> FEATURE:
<223> OTHER INFORMATION: Synthetic
<220> FEATURE:
<221> NAME/KEY: misc_feature
<222> LOCATION: (31)..(32)
<223> OTHER INFORMATION: n can be a, c, g or t

<400> SEQUENCE: 14
ggccagccca gggaacctca agtgtacacc nnscctccca gccgggatga gctg    54

<210> SEQ ID NO 15
<211> LENGTH: 63
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (35)..(36)
<223> OTHER INFORMATION: n can be a, c, g or t
<220> FEATURE:
<221> NAME/KEY: misc_feature
<222> LOCATION: (41)..(42)
<223> OTHER INFORMATION: n can be a, c, g or t

<400> SEQUENCE: 15
gccctgttgc caccggctct tgtcgacggt gagsnnggas nncaggaaga aggatccgtc    60
gct    63

<210> SEQ ID NO 16
<211> LENGTH: 232
<212> TYPE: PRT
<213> ORGANISM: Artificial
<220> FEATURE:
<223> OTHER INFORMATION: Fc1 sequence

<400> SEQUENCE: 16

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Leu Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Cys Ser Asp Gly Ser Phe Phe Leu Tyr
            180                 185                 190

```
Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
        210                 215                 220

Ser Leu Ser Leu Ser Pro Gly Lys
225                 230

<210> SEQ ID NO 17
<211> LENGTH: 232
<212> TYPE: PRT
<213> ORGANISM: Artificial
<220> FEATURE:
<223> OTHER INFORMATION: Fc2 sequence

<400> SEQUENCE: 17

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Gly Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Leu
            180                 185                 190

Ser Cys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
        210                 215                 220

Ser Leu Ser Leu Ser Pro Gly Lys
225                 230

<210> SEQ ID NO 18
<211> LENGTH: 232
<212> TYPE: PRT
<213> ORGANISM: Artificial
<220> FEATURE:
<223> OTHER INFORMATION: Fc1 sequence

<400> SEQUENCE: 18

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
```

```
            20                  25                  30
Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Leu Cys Leu Val Lys Gly Phe Tyr Pro Ser
145                 150                 155                 160

Asp Ile Ala Val Glu Trp Ser Asn Gly Gln Pro Glu Asn Asn Tyr
                165                 170                 175

Lys Thr Thr Pro Pro Val Leu Cys Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 19
<211> LENGTH: 232
<212> TYPE: PRT
<213> ORGANISM: Artificial
<220> FEATURE:
<223> OTHER INFORMATION: Fc2 sequence

<400> SEQUENCE: 19

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Tyr Pro Pro Ser Arg Asp Glu Leu Thr
    130                 135                 140

Lys Asn Gln Val Ser Leu Thr Cys Leu Val Lys Gly Phe Tyr Pro Ser
```

```
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Ala
                180                 185                 190

Ser Pro Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro Gly Lys
225                 230
```

<210> SEQ ID NO 20
<211> LENGTH: 232
<212> TYPE: PRT
<213> ORGANISM: Artificial
<220> FEATURE:
<223> OTHER INFORMATION: Fc1 sequence

<400> SEQUENCE: 20

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Val Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Thr Ser Asp Gly Ser Phe Phe Leu Tyr
                180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro Gly Lys
225                 230
```

<210> SEQ ID NO 21
<211> LENGTH: 232
<212> TYPE: PRT
<213> ORGANISM: Artificial
<220> FEATURE:
<223> OTHER INFORMATION: Fc2 sequence

<400> SEQUENCE: 21

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Lys Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Thr
            180                 185                 190

Ser Gln Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 22
<211> LENGTH: 232
<212> TYPE: PRT
<213> ORGANISM: Artificial
<220> FEATURE:
<223> OTHER INFORMATION: Fc1 sequence

<400> SEQUENCE: 22

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

```
Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Leu Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Ala Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 23
<211> LENGTH: 232
<212> TYPE: PRT
<213> ORGANISM: Artificial
<220> FEATURE:
<223> OTHER INFORMATION: Fc2 sequence

<400> SEQUENCE: 23

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Trp Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu His
            180                 185                 190

Ser Arg Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 24
<211> LENGTH: 232
<212> TYPE: PRT
<213> ORGANISM: Artificial
<220> FEATURE:
<223> OTHER INFORMATION: Fc1 sequence

<400> SEQUENCE: 24

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Pro Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asn Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 25
<211> LENGTH: 232
<212> TYPE: PRT
<213> ORGANISM: Artificial
<220> FEATURE:
<223> OTHER INFORMATION: Fc2 sequence

<400> SEQUENCE: 25

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80
```

```
Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Val Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Pro
            180                 185                 190

Ser Ser Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 26
<211> LENGTH: 232
<212> TYPE: PRT
<213> ORGANISM: Artificial
<220> FEATURE:
<223> OTHER INFORMATION: Fc1 sequence

<400> SEQUENCE: 26

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Pro Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Ile Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205
```

```
Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 27
<211> LENGTH: 232
<212> TYPE: PRT
<213> ORGANISM: Artificial
<220> FEATURE:
<223> OTHER INFORMATION: Fc2 sequence

<400> SEQUENCE: 27

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Phe
            180                 185                 190

Ser Phe Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 28
<211> LENGTH: 232
<212> TYPE: PRT
<213> ORGANISM: Artificial
<220> FEATURE:
<223> OTHER INFORMATION: Fc1 sequence

<400> SEQUENCE: 28

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
```

```
                    35                  40                  45
Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
                115                 120                 125

Arg Glu Pro Gln Val Tyr Thr Leu Pro Pro Ser Arg Asp Glu Leu Thr
                130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Gly Ser Asp Gly Ser Phe Phe Leu Tyr
                180                 185                 190

Ser Lys Leu Thr Val Asp Lys Ser Arg Trp Gln Gln Gly Asn Val Phe
                195                 200                 205

Ser Cys Ser Val Met His Glu Ala Leu His Asn His Tyr Thr Gln Lys
                210                 215                 220

Ser Leu Ser Leu Ser Pro Gly Lys
225                 230

<210> SEQ ID NO 29
<211> LENGTH: 232
<212> TYPE: PRT
<213> ORGANISM: Artificial
<220> FEATURE:
<223> OTHER INFORMATION: Fc2 sequence

<400> SEQUENCE: 29

Glu Pro Lys Ser Cys Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
                 20                  25                  30

Lys Asp Thr Leu Met Ile Ser Arg Thr Pro Glu Val Thr Cys Val Val
                 35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
                115                 120                 125

Arg Glu Pro Gln Val Tyr Thr Asp Pro Pro Ser Arg Asp Glu Leu Thr
                130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
```

165                 170                 175
Lys Thr Thr Pro Pro Val Leu Asp Ser Asp Gly Ser Phe Phe Leu Pro
                180                 185                 190

Ser Ser Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro Gly Lys
225                 230

<210> SEQ ID NO 30
<211> LENGTH: 232
<212> TYPE: PRT
<213> ORGANISM: Artificial
<220> FEATURE:
<223> OTHER INFORMATION: Fc1 sequence

<400> SEQUENCE: 30

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Leu Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Arg Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 31
<211> LENGTH: 232
<212> TYPE: PRT
<213> ORGANISM: Artificial
<220> FEATURE:
<223> OTHER INFORMATION: Fc2 sequence

<400> SEQUENCE: 31

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Glu Pro Pro Ser Arg Asp Glu Leu Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Leu
            180                 185                 190

Ser Val Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 32
<211> LENGTH: 312
<212> TYPE: DNA
<213> ORGANISM: Artificial
<220> FEATURE:
<223> OTHER INFORMATION: VL sequence

<400> SEQUENCE: 32
gacattcaga tgactcagag cccttcttca ctgtcagctt ccgtgggcga cagagtcact      60
atcacctgcc gcgcaagtca ggatgtgaac accgcagtcg cctggtacca gcagaagctc     120
ggcaaagctc caaagctgct gatctacagc gcatctttcc tgtattctgg agtgcccagt     180
aggtttagtg gtcacggtc cggtaccgac ttcacactga ctatctccag cctgcagcct     240
gaggattttg ccacatacta ttgccagcag cactatacca caccccctac tttcggccag     300
ggaaccaaag tg                                                         312

<210> SEQ ID NO 33
<211> LENGTH: 104
<212> TYPE: PRT
<213> ORGANISM: Artificial
<220> FEATURE:
<223> OTHER INFORMATION: VL sequence

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val
            100

<210> SEQ ID NO 34
<211> LENGTH: 330
<212> TYPE: DNA
<213> ORGANISM: Artificial
<220> FEATURE:
<223> OTHER INFORMATION: CL sequence

<400> SEQUENCE: 34
gagatcaagc gaactgtggc cgctccaagc gtcttcattt ttccaccctc tgacgaacag     60
ctgaagtcag ggacagcttc cgtggtctgt ctgctgaaca atttttaccc caggaggcc    120 aaagtgcagt ggaaggtcga taacgctctg cagagcggaa attctcagga gagtgtgaca    180
gaacaggact caaaagattc cacttatagc ctgtctagta ccctgacact gtccaaggca    240
gactacgaaa agcataaagt gtatgcctgt gaggtcacac atcagggtct gtcaagcccc    300
gtcactaagt ccttcaatcg tggcgaatgc                                      330

<210> SEQ ID NO 35
<211> LENGTH: 110
<212> TYPE: PRT
<213> ORGANISM: Artificial
<220> FEATURE:
<223> OTHER INFORMATION: CL sequence

<400> SEQUENCE: 35

Glu Ile Lys Arg Thr Val Ala Ala Pro Ser Val Phe Ile Phe Pro Pro
1               5                   10                  15

Ser Asp Glu Gln Leu Lys Ser Gly Thr Ala Ser Val Val Cys Leu Leu
            20                  25                  30

Asn Asn Phe Tyr Pro Arg Glu Ala Lys Val Gln Trp Lys Val Asp Asn
        35                  40                  45

Ala Leu Gln Ser Gly Asn Ser Gln Glu Ser Val Thr Glu Gln Asp Ser
    50                  55                  60

Lys Asp Ser Thr Tyr Ser Leu Ser Ser Thr Leu Thr Leu Ser Lys Ala
65                  70                  75                  80

Asp Tyr Glu Lys His Lys Val Tyr Ala Cys Glu Val Thr His Gln Gly
                85                  90                  95

Leu Ser Ser Pro Val Thr Lys Ser Phe Asn Arg Gly Glu Cys
            100                 105                 110

<210> SEQ ID NO 36
<211> LENGTH: 360
<212> TYPE: DNA
<213> ORGANISM: Artificial
<220> FEATURE:
<223> OTHER INFORMATION: VH sequence

<400> SEQUENCE: 36

```
gaggtgcagc tggtcgaaag tgggggtggg ctggtgcagc caggcggatc actgaggctg    60
tcctgcgccg ctagcggctt caacatcaaa gacacctata ttcactgggt ccgacaggca   120
ccagggaagg gtctggaatg ggtggctcgt atctacccta caaatggtta cactagatat   180
gccgactccg tgaaaggccg gtttactatt tctgctgata ccagtaagaa cacagcatac   240
ctgcagatga atagcctgag ggctgaggat accgcagtgt actattgctc tcggtggggg   300
ggtgacggct ctacgctat ggattattgg ggccagggaa ctctggtcac cgtgtccagc    360
```

<210> SEQ ID NO 37
<211> LENGTH: 120
<212> TYPE: PRT
<213> ORGANISM: Artificial
<220> FEATURE:
<223> OTHER INFORMATION: VH sequence

<400> SEQUENCE: 37

```
Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
            100                 105                 110
Gly Thr Leu Val Thr Val Ser Ser
        115                 120
```

<210> SEQ ID NO 38
<211> LENGTH: 990
<212> TYPE: DNA
<213> ORGANISM: Artificial
<220> FEATURE:
<223> OTHER INFORMATION: CH sequence

<400> SEQUENCE: 38

```
gcttcaacaa aaggaccttc cgtgtttcca ctggcaccct ctagtaagag tacttcagga    60
ggaaccgcag cactgggatg tctggtgaag gactacttcc cagagccgt caccgtgtct    120
tggaacagtg gagcactgac ctccggggtc catacatttc ctgccgtgct gcagtcatcc   180
ggtctgtata gcctgagctc tgtggtcaca gtcccaagtt catccctggg cacccagaca   240
tacatctgca acgtgaatca caaaccttcc aatactaagg tcgacaagaa agtggaacca   300
aaaagctgtg ataagactca tacctgccca ccttgtcctg caccagagct gctgggaggt   360
ccaagcgtgt tcctgttccc acccaagccc aagacacac tgatgatttc tcgcacaccc    420
gaagtcactt gtgtggtcgt ggacgtgtcc cacgaggatc ctgaagtcaa gttcaactgg   480
tacgtggatg gcgtcgaggt gcataatgct aagaccaaac ccagagagga acagtacaac   540
agcacctatc gcgtcgtgtc tgtcctgaca gtgctgcacc aggattggct gaacggaaag   600
```

```
gagtacaagt gcaaagtgag caacaaggcc ctgcccgctc ctatcgagaa gaccatttct    660
aaggctaaag gccagcctag agaaccacag gtgtatacac tgcctccaag tcgcgacgag    720
ctgacaaaaa accaggtctc cctgctgtgt ctggtgaagg gattctaccc tagcgatatc    780
gcagtggagt gggaatctaa tgggcagcca gaaaacaatt ataagaccac accccctgtg    840
ctgtgctcag atggttcctt ctttctgtac agtaaactga ccgtggacaa gtccaggtgg    900
cagcagggga acgtcttttc ctgcagcgtg atgcatgagg ccctgcacaa tcattacaca    960
cagaaatctc tgagtctgtc accaggaaag                                     990
```

<210> SEQ ID NO 39
<211> LENGTH: 330
<212> TYPE: PRT
<213> ORGANISM: Artificial
<220> FEATURE:
<223> OTHER INFORMATION: CH sequence

<400> SEQUENCE: 39

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Leu Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Cys Ser Asp Gly Ser Phe Phe
        275                 280                 285

Leu Tyr Ser Lys Leu Thr Val Asp Lys Ser Arg Trp Gln Gln Gly Asn
```

```
                290              295              300
        Val Phe Ser Cys Ser Val Met His Glu Ala Leu His Asn His Tyr Thr
        305              310              315              320

Gln Lys Ser Leu Ser Leu Ser Pro Gly Lys
                         325              330
```

<210> SEQ ID NO 40
<211> LENGTH: 990
<212> TYPE: DNA
<213> ORGANISM: Artificial
<220> FEATURE:
<223> OTHER INFORMATION: CH sequence

<400> SEQUENCE: 40

```
gcttcaacaa aaggaccttc cgtgtttcca ctggcaccct ctagtaagag tacttcagga      60
ggaaccgcag cactgggatg tctggtgaag gactacttcc cagagcccgt caccgtgtct    120
tggaacagtg gagcactgac ctccggggtc catacatttc ctgccgtgct gcagtcatcc    180
ggtctgtata gcctgagctc tgtggtcaca gtcccaagtt catccctggg cacccagaca    240
tacatctgca acgtgaatca caaaccttcc aatactaagg tcgacaagaa agtggaacca    300
aaaagctgtg ataagactca tacctgccca ccttgtcctg caccagagct gctgggaggt    360
ccaagcgtgt tcctgtttcc acccaagccc aaagacacac tgatgatttc tcgcacaccc    420
gaagtcactt gtgtggtcgt ggacgtgtcc cacgaggatc ctgaagtcaa gttcaactgg    480
tacgtggatg gcgtcgaggt gcataatgct aagaccaaac ccagagagga acagtacaac    540
agcacctatc gcgtcgtgtc tgtcctgaca gtgctgcacc aggattggct gaacggaaag    600
gagtacaagt gcaaagtgag caacaaggcc ctgcccgctc ctatcgagaa gaccatttct    660
aaggctaaag gccagcctag agaaccacag gtgtatacag agcctccaag tcgcgacgag    720
ctgacaaaaa accaggtctc cctgacttgt ctggtgaagg gattctaccc tagcgatatc    780
gcagtggagt gggaatctaa tgggcagcca gaaaacaatt ataagaccac ccccctgtg    840
ctggactcag atggttcctt ctttctgctg agtgtgctga ccgtggacaa gtccaggtgg    900
cagcagggga acgtcttttc ctgcagcgtg atgcatgagg ccctgcacaa tcattacaca    960
cagaaatctc tgagtctgtc accaggaaag                                     990
```

<210> SEQ ID NO 41
<211> LENGTH: 330
<212> TYPE: PRT
<213> ORGANISM: Artificial
<220> FEATURE:
<223> OTHER INFORMATION: CH sequence

<400> SEQUENCE: 41

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Glu Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
    275                 280                 285

Leu Leu Ser Val Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 42
<211> LENGTH: 309
<212> TYPE: DNA
<213> ORGANISM: Artificial
<220> FEATURE:
<223> OTHER INFORMATION: VL sequence

<400> SEQUENCE: 42
cagatcgtgc tgagccagag ccccgccatc ctgagcgcca gccccggcga gaaggtgacc    60
atgacctgca gggccagcag cagcgtgagc tacatccact ggttccagca gaagcccggc   120
agcagcccca agcctggat ctacgccacc agcaacctgg ccagcggcgt gcccgtgagg   180
ttcagcggca gcggcagcgg caccagctac agcctgacca tcagcagggt ggaggccgag   240
gacgccgcca cctactactg ccagcagtgg accagcaacc cccccacctt cggcggcggc   300
accaagctg                                                           309

<210> SEQ ID NO 43
<211> LENGTH: 103
<212> TYPE: PRT
<213> ORGANISM: Artificial
<220> FEATURE:
<223> OTHER INFORMATION: VL sequence

<400> SEQUENCE: 43

Gln Ile Val Leu Ser Gln Ser Pro Ala Ile Leu Ser Ala Ser Pro Gly

```
            1               5                  10                 15
        Glu Lys Val Thr Met Thr Cys Arg Ala Ser Ser Val Ser Tyr Ile
                        20                  25                  30
        His Trp Phe Gln Gln Lys Pro Gly Ser Ser Pro Lys Pro Trp Ile Tyr
                        35                  40                  45
        Ala Thr Ser Asn Leu Ala Ser Gly Val Pro Val Arg Phe Ser Gly Ser
                    50                  55                  60
        Gly Ser Gly Thr Ser Tyr Ser Leu Thr Ile Ser Arg Val Glu Ala Glu
        65                  70                  75                  80
        Asp Ala Ala Thr Tyr Tyr Cys Gln Gln Trp Thr Ser Asn Pro Pro Thr
                        85                  90                  95
        Phe Gly Gly Gly Thr Lys Leu
                    100
```

<210> SEQ ID NO 44
<211> LENGTH: 363
<212> TYPE: DNA
<213> ORGANISM: Artificial
<220> FEATURE:
<223> OTHER INFORMATION: VH sequence

<400> SEQUENCE: 44

```
caggtgcagc tgcagcagcc cggcgccgag ctggtgaagc ccggcgccag cgtgaagatg    60
agctgcaagg ccagcggcta caccttcacc agctacaaca tgcactgggt gaagcagacc   120
cccggcaggg gcctggagtg gatcggcgcc atctaccccg gcaacggcga caccagctac   180
aaccagaagt tcaagggcaa ggccaccctg accgccgaca gagcagcag caccgcctac   240
atgcagctga gcagcctgac cagcgaggac agcgccgtgt actactgcgc caggagcacc   300
tactacggcg gcgactggta cttcaacgtg tggggcgccg gcaccaccgt gaccgtgagc   360
gcc                                                                  363
```

<210> SEQ ID NO 45
<211> LENGTH: 121
<212> TYPE: PRT
<213> ORGANISM: Artificial
<220> FEATURE:
<223> OTHER INFORMATION: VH sequence

<400> SEQUENCE: 45

```
        Gln Val Gln Leu Gln Gln Pro Gly Ala Glu Leu Val Lys Pro Gly Ala
        1               5                  10                  15
        Ser Val Lys Met Ser Cys Lys Ala Ser Gly Tyr Thr Phe Thr Ser Tyr
                        20                  25                  30
        Asn Met His Trp Val Lys Gln Thr Pro Gly Arg Gly Leu Glu Trp Ile
                        35                  40                  45
        Gly Ala Ile Tyr Pro Gly Asn Gly Asp Thr Ser Tyr Asn Gln Lys Phe
                    50                  55                  60
        Lys Gly Lys Ala Thr Leu Thr Ala Asp Lys Ser Ser Thr Ala Tyr
        65                  70                  75                  80
        Met Gln Leu Ser Ser Leu Thr Ser Glu Asp Ser Ala Val Tyr Tyr Cys
                        85                  90                  95
        Ala Arg Ser Thr Tyr Tyr Gly Gly Asp Trp Tyr Phe Asn Val Trp Gly
                    100                 105                 110
        Ala Gly Thr Thr Val Thr Val Ser Ala
                    115                 120
```

<210> SEQ ID NO 46
<211> LENGTH: 990
<212> TYPE: DNA
<213> ORGANISM: Artificial
<220> FEATURE:
<223> OTHER INFORMATION: CH sequence

<400> SEQUENCE: 46

| | | |
|---|---|---|
| gcttcaacaa aaggaccttc cgtgtttcca ctggcaccct ctagtaagag tacttcagga | 60 |
| ggaaccgcag cactgggatg tctggtgaag gactacttcc cagagcccgt caccgtgtct | 120 |
| tggaacagtg gagcactgac ctccggggtc catacatttc ctgccgtgct gcagtcatcc | 180 |
| ggtctgtata gcctgagctc tgtggtcaca gtcccaagtt catccctggg cacccagaca | 240 |
| tacatctgca acgtgaatca caaaccttcc aatactaagg tcgacaagaa agtggaacca | 300 |
| aaaagctgtg ataagactca tacctgccca ccttgtcctg caccagagct gctgggaggt | 360 |
| ccaagcgtgt tcctgtttcc acccaagccc aaagacacac tgatgatttc tcgcacaccc | 420 |
| gaagtcactt gtgtggtcgt ggacgtgtcc cacgaggatc ctgaagtcaa gttcaactgg | 480 |
| tacgtggatg gcgtcgaggt gcataatgct aagaccaaac ccagagagga acagtacaac | 540 |
| agcacctatc gcgtcgtgtc tgtcctgaca gtgctgcacc aggattggct gaacggaaag | 600 |
| gagtacaagt gcaaagtgag caacaaggcc ctgcccgctc ctatcgagaa gaccatttct | 660 |
| aaggctaaag gccagcctag agaaccacag gtgtatacac tgcctccaag tcgcgacgag | 720 |
| ctgacaaaaa accaggtctc cctgctgtgt ctggtgaagg gattctaccc tagcgatatc | 780 |
| gcagtggagt gggaatctaa tgggcagcca gaaaacaatt ataagaccac ccccctgtg | 840 |
| ctgtgctcag atggttcctt ctttctgtac agtaaactga ccgtggacaa gtccaggtgg | 900 |
| cagcagggga acgtcttttc ctgcagcgtg atgcatgagg ccctgcacaa tcattacaca | 960 |
| cagaaatctc tgagtctgtc accaggaaag | 990 |

<210> SEQ ID NO 47
<211> LENGTH: 990
<212> TYPE: DNA
<213> ORGANISM: Artificial
<220> FEATURE:
<223> OTHER INFORMATION: CH sequence

<400> SEQUENCE: 47

| | | |
|---|---|---|
| gcttcaacaa aaggaccttc cgtgtttcca ctggcaccct ctagtaagag tacttcagga | 60 |
| ggaaccgcag cactgggatg tctggtgaag gactacttcc cagagcccgt caccgtgtct | 120 |
| tggaacagtg gagcactgac ctccggggtc catacatttc ctgccgtgct gcagtcatcc | 180 |
| ggtctgtata gcctgagctc tgtggtcaca gtcccaagtt catccctggg cacccagaca | 240 |
| tacatctgca acgtgaatca caaaccttcc aatactaagg tcgacaagaa agtggaacca | 300 |
| aaaagctgtg ataagactca tacctgccca ccttgtcctg caccagagct gctgggaggt | 360 |
| ccaagcgtgt tcctgtttcc acccaagccc aaagacacac tgatgatttc tcgcacaccc | 420 |
| gaagtcactt gtgtggtcgt ggacgtgtcc cacgaggatc ctgaagtcaa gttcaactgg | 480 |
| tacgtggatg gcgtcgaggt gcataatgct aagaccaaac ccagagagga acagtacaac | 540 |
| agcacctatc gcgtcgtgtc tgtcctgaca gtgctgcacc aggattggct gaacggaaag | 600 |
| gagtacaagt gcaaagtgag caacaaggcc ctgcccgctc ctatcgagaa gaccatttct | 660 |
| aaggctaaag gccagcctag agaaccacag gtgtatacac tgcctccaag tcgcgacgag | 720 |
| ctgacaaaaa accaggtctc cctgctgtgt ctggtgaagg gattctaccc tagcgatatc | 780 |

```
gcagtggagt gggaatctaa tgggcagcca gaaaacaatt ataagaccac accccctgtg    840
ctgcggtcag atggttcctt ctttctgtac agtaaactga ccgtggacaa gtccaggtgg    900 cagcaggga  acgtctttc  ctgcagcgtg atgcatgagg ccctgcacaa tcattacaca    960
cagaaatctc tgagtctgtc accaggaaag                                     990
```

<210> SEQ ID NO 48
<211> LENGTH: 330
<212> TYPE: PRT
<213> ORGANISM: Artificial
<220> FEATURE:
<223> OTHER INFORMATION: CH sequence

<400> SEQUENCE: 48

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Leu Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Cys Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
```

<210> SEQ ID NO 49
<211> LENGTH: 330
<212> TYPE: PRT
<213> ORGANISM: Artificial
<220> FEATURE:
<223> OTHER INFORMATION: CH sequence

<400> SEQUENCE: 49

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Leu Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Arg Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 50
<211> LENGTH: 312
<212> TYPE: DNA

<213> ORGANISM: Artificial
<220> FEATURE:
<223> OTHER INFORMATION: VL sequence

<400> SEQUENCE: 50

```
gatatccagc tgacccagag ccctagcagc ctgagcgcta gcgtgggcga cagggtgagc    60
atcacctgca aggccagcca ggacgtgtcc atcgccgtgg cctggtatca acagaagccc   120
ggcaaggccc ccaagctgct gatctacagc gccagctaca gtacaccgg cgtgcccgac    180
agatttagcg gcagcggctc cggcacagac ttcaccctga ccatcagcag cctgcagccc   240
gaggacttcg ccgtgtacta ctgccagcag cactacatca ccccccctga ctttggcgcc   300
ggcaccaaag tg                                                       312
```

<210> SEQ ID NO 51
<211> LENGTH: 104
<212> TYPE: PRT
<213> ORGANISM: Artificial
<220> FEATURE:
<223> OTHER INFORMATION: VL sequence

<400> SEQUENCE: 51

Asp Ile Gln Leu Thr Gln Ser Pro Ser Ser Leu Ser Ala Ser Val Gly
1               5                   10                  15

Asp Arg Val Ser Ile Thr Cys Lys Ala Ser Gln Asp Val Ser Ile Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ile Thr Pro Leu
                85                  90                  95

Thr Phe Gly Ala Gly Thr Lys Val
            100

<210> SEQ ID NO 52
<211> LENGTH: 360
<212> TYPE: DNA
<213> ORGANISM: Artificial
<220> FEATURE:
<223> OTHER INFORMATION: VH sequence

<400> SEQUENCE: 52

```
gtgcagctgc agcagtccgg cagcgagctg aagaagcctg cgccagcgt gaaggtgagc     60
tgcaaggcca gcggctacac cttcaccaac tacggcatga ctgggtgaa gcaggcccct    120
ggccagggac tgaagtggat gggctggatc aacacctaca ccggcgagcc cacctacacc    180
gacgacttca gggcaggtt cgccttcagc ctggacacca gcgtgtccac cgcctacctg    240
cagatctcca gcctgaaggc cgacgacacc gccgtgtact ctgcgccag aggcggcttc    300
ggcagcagct actggtactt cgacgtgtgg ggccagggaa gcctggtgac cgtgagcagc   360
```

<210> SEQ ID NO 53
<211> LENGTH: 120
<212> TYPE: PRT
<213> ORGANISM: Artificial
<220> FEATURE:
<223> OTHER INFORMATION: VH sequence

<400> SEQUENCE: 53

| | | | | | | | | | | | | | | |
|---|---|---|---|---|---|---|---|---|---|---|---|---|---|---|
|Val|Gln|Leu|Gln|Gln|Ser|Gly|Ser|Glu|Leu|Lys|Lys|Pro|Gly|Ala|Ser|
|1| | | |5| | | | |10| | | | |15|

Val Lys Val Ser Cys Lys Ala Ser Gly Tyr Thr Phe Thr Asn Tyr Gly
          20                25              30

Met Asn Trp Val Lys Gln Ala Pro Gly Gln Gly Leu Lys Trp Met Gly
       35             40              45

Trp Ile Asn Thr Tyr Thr Gly Glu Pro Thr Tyr Thr Asp Asp Phe Lys
   50               55                60

Gly Arg Phe Ala Phe Ser Leu Asp Thr Ser Val Ser Thr Ala Tyr Leu
65              70              75            80

Gln Ile Ser Ser Leu Lys Ala Asp Asp Thr Ala Val Tyr Phe Cys Ala
            85              90            95

Arg Gly Gly Phe Gly Ser Ser Tyr Trp Tyr Phe Asp Val Trp Gly Gln
         100              105          110

Gly Ser Leu Val Thr Val Ser Ser
       115            120

<210> SEQ ID NO 54
<211> LENGTH: 990
<212> TYPE: DNA
<213> ORGANISM: Artificial
<220> FEATURE:
<223> OTHER INFORMATION: CH sequence

<400> SEQUENCE: 54

```
gcttcaacaa aaggaccttc cgtgtttcca ctggcaccct ctagtaagag tacttcagga      60
ggaaccgcag cactgggatg tctggtgaag gactacttcc cagagcccgt caccgtgtct     120
tggaacagtg gagcactgac ctccggggtc catacatttc ctgccgtgct gcagtcatcc     180
ggtctgtata gcctgagctc tgtggtcaca gtcccaagtt catccctggg cacccagaca     240
tacatctgca acgtgaatca caaaccttcc aatactaagg tcgacaagaa agtggaacca     300
aaaagctgtg ataagactca tacctgccca ccttgtcctg caccagagct gctgggaggt     360
ccaagcgtgt tcctgtttcc acccaagccc aaagacacac tgatgatttc tcgcacaccc     420
gaagtcactt gtgtggtcgt ggacgtgtcc cacgaggatc ctgaagtcaa gttcaactgg     480
tacgtggatg gcgtcgaggt gcataatgct aagaccaaac cagagagga acagtacaac      540
agcacctatc gcgtcgtgtc tgtcctgaca gtgctgcacc aggattggct gaacggaaag     600
gagtacaagt gcaaagtgag caacaaggcc ctcccgctc ctatcgagaa gaccatttct      660
aaggctaaag gccagcctag agaaccacag gtgtatacac tgcctccaag tcgcgacgag     720
ctgacaaaaa accaggtctc cctgccctgt ctggtgaagg gattctaccc tagcgatatc     780
gcagtggagt gggaatctaa tgggcagcca gaaacaatt ataagaccac accccctgtg      840
ctgaactcag atggttcctt ctttctgtac agtaaactga ccgtggacaa gtccaggtgg     900
cagcagggga acgtcttttc ctgcagcgtg atgcatgagg ccctgcacaa tcattacaca     960
cagaaatctc tgagtctgtc accaggaaag                                     990
```

<210> SEQ ID NO 55
<211> LENGTH: 330
<212> TYPE: PRT
<213> ORGANISM: Artificial
<220> FEATURE:
<223> OTHER INFORMATION: CH sequence

<400> SEQUENCE: 55

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Pro Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asn Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 56
<211> LENGTH: 312
<212> TYPE: DNA
<213> ORGANISM: Artificial
<220> FEATURE:
<223> OTHER INFORMATION: VL sequence

<400> SEQUENCE: 56
gacatccaga tgacccagag ccctagcagc ctgagcgcta gcgtgggcga cagggtgacc    60
atcacctgca gggccagcca ggatgtgagc accgctgtgg cctggtatca acagaagccc   120
ggcaaggccc ccaagctgct gatctacagc gccagcttcc tgtacagcgg cgtgcccagc   180

```
agatttagcg gcagcggcag cggcaccgat tcaccctga ccatcagcag cctgcagccc    240
gaggacttcg ccacctacta ctgccagcag tacctgtacc atcccgccac cttcggccag    300
ggcaccaagg tg                                                        312
```

<210> SEQ ID NO 57
<211> LENGTH: 104
<212> TYPE: PRT
<213> ORGANISM: Artificial
<220> FEATURE:
<223> OTHER INFORMATION: VL sequence

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val
            100

<210> SEQ ID NO 58
<211> LENGTH: 354
<212> TYPE: DNA
<213> ORGANISM: Artificial
<220> FEATURE:
<223> OTHER INFORMATION: VH sequence

<400> SEQUENCE: 58

```
gaggtgcagc tggtggagag cggaggagga ctggtgcagc ctggaggatc cctgagactg     60
agctgcgccg ccagcggctt caccttcagc gacagctgga tccactgggt gagacaggcc    120
cctggcaagg gcctggaatg ggtggcctgg atctccccctt acggcggcag cacctactac    180
gccgacagcg tgaagggcag gttcaccatc agcgccgaca ccagcaagaa caccgcctac    240
ctgcagatga acagcctgag ggccgaggac accgccgtgt actactgcgc cagaagacac    300
tggcccggcg gattcgacta ctggggacag ggcaccctgg tgaccgtgag cgcc          354
```

<210> SEQ ID NO 59
<211> LENGTH: 118
<212> TYPE: PRT
<213> ORGANISM: Artificial
<220> FEATURE:
<223> OTHER INFORMATION: VH sequence

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg His Trp Pro Gly Gly Phe Asp Tyr Trp Gly Gln Gly Thr
            100                 105                 110

Leu Val Thr Val Ser Ala
        115

<210> SEQ ID NO 60
<211> LENGTH: 990
<212> TYPE: DNA
<213> ORGANISM: Artificial
<220> FEATURE:
<223> OTHER INFORMATION: CH sequence

<400> SEQUENCE: 60
gcttcaacaa aaggaccttc cgtgtttcca ctggcaccct ctagtaagag tacttcagga      60
ggaaccgcag cactgggatg tctggtgaag gactacttcc cagagcccgt caccgtgtct     120
tggaacagtg gagcactgac ctccggggtc catacatttc ctgccgtgct gcagtcatcc     180
ggtctgtata gcctgagctc tgtggtcaca gtcccaagtt catccctggg cacccagaca     240
tacatctgca acgtgaatca caaaccttcc aatactaagg tcgacaagaa agtggaacca     300
aaaagctgtg ataagactca tacctgccca ccttgtcctg caccagagct gctgggaggt     360
ccaagcgtgt tcctgtttcc acccaagccc aaagacacac tgatgatttc tcgcacaccc     420
gaagtcactt gtgtggtcgt ggacgtgtcc cacgaggatc ctgaagtcaa gttcaactgg     480
tacgtggatg gcgtcgaggt gcataatgct aagaccaaac ccagagagga acagtacaac     540
agcacctatc gcgtcgtgtc tgtcctgaca gtgctgcacc aggattggct gaacggaaag     600
gagtacaagt gcaaagtgag caacaaggcc ctgcccgctc tatcgagaa gaccatttct     660 aaggctaaag gccagcctag agaaccacag gtgtatacac tgcctccaag tcgcgacgag     720
ctgacaaaaa accaggtctc cctgtggtgt ctggtgaagg gattctaccc tagcgatatc     780
gcagtggagt gggaatctaa tgggcagcca gaaaacaatt ataagaccac accccctgtg     840
ctgggatcag atggttcctt ctttctgtac agtaaactga ccgtggacaa gtccaggtgg     900
cagcagggga acgtcttttc ctgcagcgtg atgcatgagg ccctgcacaa tcattacaca     960
cagaaatctc tgagtctgtc accaggaaag                                       990

<210> SEQ ID NO 61
<211> LENGTH: 330
<212> TYPE: PRT
<213> ORGANISM: Artificial
<220> FEATURE:
<223> OTHER INFORMATION: CH sequence

<400> SEQUENCE: 61

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser

|   |   |   |   |   |   |   |   |   |   |   |
|---|---|---|---|---|---|---|---|---|---|---|
| | | 50 | | | 55 | | | 60 | | |
| Leu | Ser | Ser | Val | Val | Thr | Val | Pro | Ser | Ser | Leu | Gly | Thr | Gln | Thr |
| 65 | | | | | 70 | | | | 75 | | | | | 80 |
| Tyr | Ile | Cys | Asn | Val | Asn | His | Lys | Pro | Ser | Asn | Thr | Lys | Val | Asp | Lys |
| | | | | 85 | | | | | 90 | | | | | 95 | |
| Lys | Val | Glu | Pro | Lys | Ser | Cys | Asp | Lys | Thr | His | Thr | Cys | Pro | Pro | Cys |
| | | | 100 | | | | | 105 | | | | | 110 | | |
| Pro | Ala | Pro | Glu | Leu | Leu | Gly | Gly | Pro | Ser | Val | Phe | Leu | Phe | Pro | Pro |
| | | 115 | | | | | 120 | | | | | 125 | | | |
| Lys | Pro | Lys | Asp | Thr | Leu | Met | Ile | Ser | Arg | Thr | Pro | Glu | Val | Thr | Cys |
| | 130 | | | | | 135 | | | | | 140 | | | | |
| Val | Val | Val | Asp | Val | Ser | His | Glu | Asp | Pro | Glu | Val | Lys | Phe | Asn | Trp |
| 145 | | | | | 150 | | | | | 155 | | | | | 160 |
| Tyr | Val | Asp | Gly | Val | Glu | Val | His | Asn | Ala | Lys | Thr | Lys | Pro | Arg | Glu |
| | | | | 165 | | | | | 170 | | | | | 175 | |
| Glu | Gln | Tyr | Asn | Ser | Thr | Tyr | Arg | Val | Val | Ser | Val | Leu | Thr | Val | Leu |
| | | | 180 | | | | | 185 | | | | | 190 | | |
| His | Gln | Asp | Trp | Leu | Asn | Gly | Lys | Glu | Tyr | Lys | Cys | Lys | Val | Ser | Asn |
| | | 195 | | | | | 200 | | | | | 205 | | | |
| Lys | Ala | Leu | Pro | Ala | Pro | Ile | Glu | Lys | Thr | Ile | Ser | Lys | Ala | Lys | Gly |
| | 210 | | | | | 215 | | | | | 220 | | | | |
| Gln | Pro | Arg | Glu | Pro | Gln | Val | Tyr | Thr | Leu | Pro | Pro | Ser | Arg | Asp | Glu |
| 225 | | | | | 230 | | | | | 235 | | | | | 240 |
| Leu | Thr | Lys | Asn | Gln | Val | Ser | Leu | Trp | Cys | Leu | Val | Lys | Gly | Phe | Tyr |
| | | | | 245 | | | | | 250 | | | | | 255 | |
| Pro | Ser | Asp | Ile | Ala | Val | Glu | Trp | Glu | Ser | Asn | Gly | Gln | Pro | Glu | Asn |
| | | | 260 | | | | | 265 | | | | | 270 | | |
| Asn | Tyr | Lys | Thr | Thr | Pro | Pro | Val | Leu | Gly | Ser | Asp | Gly | Ser | Phe | Phe |
| | | 275 | | | | | 280 | | | | | 285 | | | |
| Leu | Tyr | Ser | Lys | Leu | Thr | Val | Asp | Lys | Ser | Arg | Trp | Gln | Gln | Gly | Asn |
| | 290 | | | | | 295 | | | | | 300 | | | | |
| Val | Phe | Ser | Cys | Ser | Val | Met | His | Glu | Ala | Leu | His | Asn | His | Tyr | Thr |
| 305 | | | | | 310 | | | | | 315 | | | | | 320 |
| Gln | Lys | Ser | Leu | Ser | Leu | Ser | Pro | Gly | Lys | | | | | | |
| | | | | 325 | | | | | 330 | | | | | | |

<210> SEQ ID NO 62
<211> LENGTH: 729
<212> TYPE: DNA
<213> ORGANISM: Artificial
<220> FEATURE:
<223> OTHER INFORMATION: variable region sequence

<400> SEQUENCE: 62

```
gatatcaagc tgcagcagag cggtgcagaa ctggccagac ctggcgcttc agtgaaaatg    60
tcctgtaaga ctagcggcta cacattcact cgatatacca tgcactgggt gaagcagcgt   120
ccagggcagg gtctggagtg gatcggatat attaacccct ctcgcgggta caccaactat   180
aatcagaagt ttaaagacaa ggccacactg actaccgata agagctctag tactgcttac   240
atgcagctgt catccctgac cagcgaagac tctgcagtgt actattgcgc ccgatactat   300
gacgatcatt actgtctgga ctactgggc cagggaacaa ctctgactgt cagctctgtg   360
gagggaggaa gtgaaggttc aggaggatcc ggaggtagcg aggagtggac gatatccag   420
ctgacccagt ctcccgccat tatgtccgct agccctggcg agaaagtcac catgacatgc   480
```

| | |
|---|---|
| agagccagtt catccgtgtc ctacatgaat tggtatcagc agaaatctgg aacaagtcca | 540 |
| aagaggtgga tctacgacac ttctaaggtc gcaagtgggg tgccctatcg gttttctggg | 600 |
| agtggttcag gcacttccta cagcctgacc attagctcta tggaggccga agatgctgca | 660 |
| acctactatt gccagcagtg gagtagcaat cctctgacat tggagcagg gactaaactg | 720 |
| gaactgaag | 729 |

<210> SEQ ID NO 63
<211> LENGTH: 243
<212> TYPE: PRT
<213> ORGANISM: Artificial
<220> FEATURE:
<223> OTHER INFORMATION: variable region sequence

<400> SEQUENCE: 63

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Ser Gly
            115                 120                 125

Gly Ser Gly Gly Ser Gly Gly Val Asp Asp Ile Gln Leu Thr Gln Ser
        130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
            165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
            195                 200                 205

Leu Thr Ile Ser Ser Met Glu Ala Glu Asp Ala Ala Thr Tyr Tyr Cys
        210                 215                 220

Gln Gln Trp Ser Ser Asn Pro Leu Thr Phe Gly Ala Gly Thr Lys Leu
225                 230                 235                 240

Glu Leu Lys

<210> SEQ ID NO 64
<211> LENGTH: 990
<212> TYPE: DNA
<213> ORGANISM: Artificial
<220> FEATURE:
<223> OTHER INFORMATION: constant region sequence

<400> SEQUENCE: 64

| | |
|---|---|
| gcttcaacaa aaggaccttc cgtgtttcca ctggcaccct ctagtaagag tacttcagga | 60 |

| | |
|---|---|
| ggaaccgcag cactgggatg tctggtgaag gactacttcc cagagcccgt caccgtgtct | 120 |
| tggaacagtg gagcactgac ctccggggtc catacatttc ctgccgtgct gcagtcatcc | 180 |
| ggtctgtata gcctgagctc tgtggtcaca gtcccaagtt catccctggg cacccagaca | 240 |
| tacatctgca acgtgaatca caaaccttcc aatactaagg tcgacaagaa agtggaacca | 300 |
| aaaagctgtg ataagactca tacctgccca ccttgtcctg caccagagct gctgggaggt | 360 |
| ccaagcgtgt tcctgtttcc acccaagccc aaagacacac tgatgatttc tcgcacaccc | 420 |
| gaagtcactt gtgtggtcgt ggacgtgtcc cacgaggatc ctgaagtcaa gttcaactgg | 480 |
| tacgtggatg gcgtcgaggt gcataatgct aagaccaaac ccagagagga acagtacaac | 540 |
| agcacctatc gcgtcgtgtc tgtcctgaca gtgctgcacc aggattggct gaacggaaag | 600 |
| gagtacaagt gcaaagtgag caacaaggcc ctgcccgctc tatcgagaa gaccatttct | 660 |
| aaggctaaag gccagcctag agaaccacag gtgtatacag gacctccaag tcgcgacgag | 720 |
| ctgacaaaaa accaggtctc cctgacttgt ctggtgaagg gattctaccc tagcgatatc | 780 |
| gcagtggagt gggaatctaa tgggcagcca gaaaacaatt ataagaccac acccctgtg | 840 |
| ctggactcag atggttcctt ctttctgctc agttgtctga ccgtggacaa gtccaggtgg | 900 |
| cagcagggga acgtcttttc ctgcagcgtg atgcatgagg ccctgcacaa tcattacaca | 960 |
| cagaaatctc tgagtctgtc accaggaaag | 990 |

<210> SEQ ID NO 65
<211> LENGTH: 990
<212> TYPE: DNA
<213> ORGANISM: Artificial
<220> FEATURE:
<223> OTHER INFORMATION: constant region sequence

<400> SEQUENCE: 65

| | |
|---|---|
| gcttcaacaa aaggaccttc cgtgtttcca ctggcaccct ctagtaagag tacttcagga | 60 |
| ggaaccgcag cactgggatg tctggtgaag gactacttcc cagagcccgt caccgtgtct | 120 |
| tggaacagtg gagcactgac ctccggggtc catacatttc ctgccgtgct gcagtcatcc | 180 |
| ggtctgtata gcctgagctc tgtggtcaca gtcccaagtt catccctggg cacccagaca | 240 |
| tacatctgca acgtgaatca caaaccttcc aatactaagg tcgacaagaa agtggaacca | 300 |
| aaaagctgtg ataagactca tacctgccca ccttgtcctg caccagagct gctgggaggt | 360 |
| ccaagcgtgt tcctgtttcc acccaagccc aaagacacac tgatgatttc tcgcacaccc | 420 |
| gaagtcactt gtgtggtcgt ggacgtgtcc cacgaggatc ctgaagtcaa gttcaactgg | 480 |
| tacgtggatg gcgtcgaggt gcataatgct aagaccaaac ccagagagga acagtacaac | 540 |
| agcacctatc gcgtcgtgtc tgtcctgaca gtgctgcacc aggattggct gaacggaaag | 600 |
| gagtacaagt gcaaagtgag caacaaggcc ctgcccgctc tatcgagaa gaccatttct | 660 |
| aaggctaaag gccagcctag agaaccacag gtgtatacat atcctccaag tcgcgacgag | 720 |
| ctgacaaaaa accaggtctc cctgacttgt ctggtgaagg gattctaccc tagcgatatc | 780 |
| gcagtggagt gggaatctaa tgggcagcca gaaaacaatt ataagaccac acccctgtg | 840 |
| ctggactcag atggttcctt ctttctggca agtcctctga ccgtggacaa gtccaggtgg | 900 |
| cagcagggga acgtcttttc ctgcagcgtg atgcatgagg ccctgcacaa tcattacaca | 960 |
| cagaaatctc tgagtctgtc accaggaaag | 990 |

<210> SEQ ID NO 66
<211> LENGTH: 990

<212> TYPE: DNA
<213> ORGANISM: Artificial
<220> FEATURE:
<223> OTHER INFORMATION: constant region sequence

<400> SEQUENCE: 66

```
gcttcaacaa aaggaccttc cgtgtttcca ctggcaccct ctagtaagag tacttcagga      60
ggaaccgcag cactgggatg tctggtgaag gactacttcc cagagcccgt caccgtgtct    120
tggaacagtg gagcactgac ctccggggtc catacatttc ctgccgtgct gcagtcatcc    180
ggtctgtata gcctgagctc tgtggtcaca gtcccaagtt catccctggg cacccagaca    240
tacatctgca acgtgaatca caaaccttcc aatactaagg tcgacaagaa agtggaacca    300
aaaagctgtg ataagactca tacctgccca ccttgtcctg caccagagct gctgggaggt    360
ccaagcgtgt tcctgtttcc acccaagccc aaagacacac tgatgatttc tcgcacaccc    420
gaagtcactt gtgtggtcgt ggacgtgtcc cacgaggatc ctgaagtcaa gttcaactgg    480
tacgtggatg gcgtcgaggt gcataatgct aagaccaaac ccagagagga acagtacaac    540
agcacctatc gcgtcgtgtc tgtcctgaca gtgctgcacc aggattggct gaacggaaag    600
gagtacaagt gcaaagtgag caacaaggcc ctgcccgctc ctatcgagaa gaccatttct    660
aaggctaaag gccagcctag agaaccacag gtgtatacag ttcctccaag tcgcgacgag    720
ctgacaaaaa accaggtctc cctgacttgt ctggtgaagg gattctaccc tagcgatatc    780
gcagtggagt gggaatctaa tgggcagcca gaaaacaatt ataagaccac accccctgtg    840
ctggactcag atggttcctt ctttctgcca agttcactga ccgtggacaa gtccaggtgg    900
cagcagggga acgtcttttc ctgcagcgtg atgcatgagg ccctgcacaa tcattacaca    960
cagaaatctc tgagtctgtc accaggaaag                                     990
```

<210> SEQ ID NO 67
<211> LENGTH: 990
<212> TYPE: DNA
<213> ORGANISM: Artificial
<220> FEATURE:
<223> OTHER INFORMATION: constant region sequence

<400> SEQUENCE: 67

```
gcttcaacaa aaggaccttc cgtgtttcca ctggcaccct ctagtaagag tacttcagga      60
ggaaccgcag cactgggatg tctggtgaag gactacttcc cagagcccgt caccgtgtct    120
tggaacagtg gagcactgac ctccggggtc catacatttc ctgccgtgct gcagtcatcc    180
ggtctgtata gcctgagctc tgtggtcaca gtcccaagtt catccctggg cacccagaca    240
tacatctgca acgtgaatca caaaccttcc aatactaagg tcgacaagaa agtggaacca    300
aaaagctgtg ataagactca tacctgccca ccttgtcctg caccagagct gctgggaggt    360
ccaagcgtgt tcctgtttcc acccaagccc aaagacacac tgatgatttc tcgcacaccc    420
gaagtcactt gtgtggtcgt ggacgtgtcc cacgaggatc ctgaagtcaa gttcaactgg    480
tacgtggatg gcgtcgaggt gcataatgct aagaccaaac ccagagagga acagtacaac    540
agcacctatc gcgtcgtgtc tgtcctgaca gtgctgcacc aggattggct gaacggaaag    600
gagtacaagt gcaaagtgag caacaaggcc ctgcccgctc ctatcgagaa gaccatttct    660
aaggctaaag gccagcctag agaaccacag gtgtatacag atcctccaag tcgcgacgag    720
ctgacaaaaa accaggtctc cctgacttgt ctggtgaagg gattctaccc tagcgatatc    780
gcagtggagt gggaatctaa tgggcagcca gaaaacaatt ataagaccac accccctgtg    840
```

```
ctggactcag atggttcctt ctttctgcca agtagtctga ccgtggacaa gtccaggtgg    900
cagcagggga acgtcttttc ctgcagcgtg atgcatgagg ccctgcacaa tcattacaca    960
cagaaatctc tgagtctgtc accaggaaag                                    990
```

```
<210> SEQ ID NO 68
<211> LENGTH: 330
<212> TYPE: PRT
<213> ORGANISM: Artificial
<220> FEATURE:
<223> OTHER INFORMATION: constant region sequence

<400> SEQUENCE: 68
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Gly Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Leu Ser Cys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 69
<211> LENGTH: 330
<212> TYPE: PRT
<213> ORGANISM: Artificial
<220> FEATURE:
<223> OTHER INFORMATION: constant region sequence

<400> SEQUENCE: 69

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Tyr Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Ala Ser Pro Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 70
<211> LENGTH: 330
<212> TYPE: PRT
<213> ORGANISM: Artificial
<220> FEATURE:

<223> OTHER INFORMATION: constant region sequence

<400> SEQUENCE: 70

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Val Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Pro Ser Ser Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 71
<211> LENGTH: 330
<212> TYPE: PRT
<213> ORGANISM: Artificial
<220> FEATURE:
<223> OTHER INFORMATION: constant region sequence

<400> SEQUENCE: 71

```
Ala Ser Thr Lys Gly Pro Ser Val Phe Pro Leu Ala Pro Ser Ser Lys
1               5                   10                  15
```

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Asp Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Pro Ser Ser Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 72
<211> LENGTH: 15
<212> TYPE: PRT
<213> ORGANISM: Artificial
<220> FEATURE:
<223> OTHER INFORMATION: Synthetic

<400> SEQUENCE: 72

Gly Gly Gly Gly Ser Gly Gly Gly Ser Gly Gly Gly Gly Ser
1               5                   10                  15

<210> SEQ ID NO 73
<211> LENGTH: 213
<212> TYPE: PRT
<213> ORGANISM: Artificial
```

<220> FEATURE:
<223> OTHER INFORMATION: Anti-CD20 light chain in anti-CD20 homodimer

<400> SEQUENCE: 73

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 74
<211> LENGTH: 451
<212> TYPE: PRT
<213> ORGANISM: Artificial
<220> FEATURE:
<223> OTHER INFORMATION: Anti-CD20 heavy chain in anti-CD20 homodimer

<400> SEQUENCE: 74

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
```

```
            115                 120                 125
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Leu Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Arg Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 75
<211> LENGTH: 214
<212> TYPE: PRT
<213> ORGANISM: Artificial
<220> FEATURE:
<223> OTHER INFORMATION: Anti-HER2 light chain in anti-HER2 homodimer

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
```

```
                20                  25                  30
Val Ala Trp Tyr Gln Gln Lys Pro Gly Lys Ala Pro Lys Leu Leu Ile
            35                  40                  45
Tyr Ser Ala Ser Phe Leu Tyr Ser Gly Val Pro Ser Arg Phe Ser Gly
        50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 76
<211> LENGTH: 450
<212> TYPE: PRT
<213> ORGANISM: Artificial
<220> FEATURE:
<223> OTHER INFORMATION: Anti-HER2 heavy chain in anti-HER2 homodimer

<400> SEQUENCE: 76

Glu Val Gln Leu Val Glu Ser Gly Gly Gly Leu Val Gln Pro Gly Gly
1               5                  10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
```

165                 170                 175
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Glu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Leu Ser Val Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 77
<211> LENGTH: 213
<212> TYPE: PRT
<213> ORGANISM: Artificial
<220> FEATURE:
<223> OTHER INFORMATION: Anti-CD20 light chain in anti-CD20/HER2
      heterodimer

<400> SEQUENCE: 77

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

```
Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                 85                  90                  95

Phe Gly Gly Gly Thr Lys Leu Glu Ile Lys Arg Thr Val Ala Ala Pro
             100                 105                 110

Ser Val Phe Ile Phe Pro Pro Ser Asp Glu Gln Leu Lys Ser Gly Thr
         115                 120                 125

Ala Ser Val Val Cys Leu Leu Asn Asn Phe Tyr Pro Arg Glu Ala Lys
     130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 78
<211> LENGTH: 451
<212> TYPE: PRT
<213> ORGANISM: Artificial
<220> FEATURE:
<223> OTHER INFORMATION: Anti-CD20 heavy chain in anti-CD20/HER2
      heterodimer

<400> SEQUENCE: 78

Gln Val Gln Leu Gln Gln Pro Gly Ala Glu Leu Val Lys Pro Gly Ala
1               5                  10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

Lys Pro Ser Asn Thr Lys Val Asp Lys Lys Val Glu Pro Lys Ser Cys
210 215 220

Asp Lys Thr His Thr Cys Pro Pro Cys Pro Ala Pro Glu Leu Leu Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser His
260 265 270

Glu Asp Pro Glu Val Lys Phe Asn Trp Tyr Val Asp Gly Val Glu Val
275 280 285

His Asn Ala Lys Thr Lys Pro Arg Glu Glu Gln Tyr Asn Ser Thr Tyr
290 295 300

Arg Val Val Ser Val Leu Thr Val Leu His Gln Asp Trp Leu Asn Gly
305 310 315 320

Lys Glu Tyr Lys Cys Lys Val Ser Asn Lys Ala Leu Pro Ala Pro Ile
325 330 335

Glu Lys Thr Ile Ser Lys Ala Lys Gly Gln Pro Arg Glu Pro Gln Val
340 345 350

Tyr Thr Leu Pro Pro Ser Arg Asp Glu Leu Thr Lys Asn Gln Val Ser
355 360 365

Leu Leu Cys Leu Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Val Leu Arg Ser Asp Gly Ser Phe Phe Leu Tyr Ser Lys Leu Thr Val
405 410 415

Asp Lys Ser Arg Trp Gln Gln Gly Asn Val Phe Ser Cys Ser Val Met
420 425 430

His Glu Ala Leu His Asn His Tyr Thr Gln Lys Ser Leu Ser Leu Ser
435 440 445

Pro Gly Lys
450

<210> SEQ ID NO 79
<211> LENGTH: 214
<212> TYPE: PRT
<213> ORGANISM: Artificial
<220> FEATURE:
<223> OTHER INFORMATION: Anti-HER2 light chain in anti-CD20/HER2
    heterodimer

<400> SEQUENCE: 79

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Pro
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 80
<211> LENGTH: 450
<212> TYPE: PRT
<213> ORGANISM: Artificial
<220> FEATURE:
<223> OTHER INFORMATION: Anti-HER2 heavy chain in anti-CD20/HER2
      heterodimer

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

-continued

```
Ser Arg Thr Pro Glu Val Thr Cys Val Val Asp Val Ser His Glu
        260             265             270

Asp Pro Glu Val Lys Phe Asn Trp Tyr Val Asp Gly Val Glu Val His
        275             280             285

Asn Ala Lys Thr Lys Pro Arg Glu Glu Gln Tyr Asn Ser Thr Tyr Arg
    290             295             300

Val Val Ser Val Leu Thr Val Leu His Gln Asp Trp Leu Asn Gly Lys
305             310             315             320

Glu Tyr Lys Cys Lys Val Ser Asn Lys Ala Leu Pro Ala Pro Ile Glu
            325             330             335

Lys Thr Ile Ser Lys Ala Lys Gly Gln Pro Arg Glu Pro Gln Val Tyr
            340             345             350

Thr Glu Pro Pro Ser Arg Asp Glu Leu Thr Lys Asn Gln Val Ser Leu
        355             360             365

Thr Cys Leu Val Lys Gly Phe Tyr Pro Ser Asp Ile Ala Val Glu Trp
    370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Leu Ser Val Leu Thr Val Asp
            405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
            435             440             445

Gly Lys
    450
```

HETERODIMERIC IMMUNOGLOBULIN CONSTRUCTS AND PREPARATION METHODS THEREOF

I. CROSS-REFERENCE TO RELATED APPLICATIONS

This Application is a National Stage of International Application No. PCT/CN2017/104044 filed Sep. 28, 2017, claiming priority to Chinese patent application Serial No. CN 2016108638147, filed Sep. 29, 2016, the disclosure of which is hereby incorporated by reference in its entirety.

II. FIELD OF THE INVENTION

The field of the invention is stable and highly specific immunoglobulin constructs that retain desirable properties of native IgG antibodies without undesirable heavy chain-light chain mispairing.

III. BACKGROUND

Monoclonal antibodies (mAbs) that possess monospecificity and interact with only a single epitope on a target antigen have been widely used for the treatment of many diseases, such as cancers, inflammatory and autoimmune diseases, and infectious diseases. However, to date, none of these therapeutic molecules have shown good enough potency as single agents due to the underlying complexity of the diseases, such as cancer or inflammatory disorders, which usually involve redundancy of disease-mediating molecular pathways as well as crosstalk between signal cascades. Because such mAbs interact with only a single target antigen, it is difficult to provide optimal therapeutic effects. Simultaneous blockade of multiple targets or multiple sites on one target should result in improved treatment potency. Additionally, targeting multiple antigens/epitopes with a single multi-specific molecule makes new drug development less complex because the therapy is reduced to a single molecule. It is also less complicated for both patients and healthcare workers when compared with the use of two or more monospecific molecule combinations.

Bispecific antibodies (BsAb) or multispecific molecules are generally known in the art. Initial attempts to make bispecific antibodies involved chemical conjugations of two existing IgG molecules, two Fab' or two (Fab')2 fragments using bifunctional coupling reagents. However, there are limitations for such kinds of chemically-conjugated BsAbs, including labor intensity for generation of the bispecific molecules, the difficulties of heterodimer purification, homodimer and original monoclonal antibody elimination, and low yield.

Another kind of BsAb molecule is a hybrid hybridoma or quadroma, produced by somatic hybridization of two hybridoma cells secreting different antibodies. Due to the random pairing of Ig heavy chains and light chains, approximately only one-tenth of the possible paired IgG mixture yields functional BsAbs, thus complicating purification and reducing production yields.

WO/2013060867 describes a method for large-scale production of heterodimeric bispecific antibodies by reduction of mixed two homodimeric immunoglobulins, resulting in Fab-arm exchange forced by the introduction of asymmetrical mutations in the CH3 domains of the homodimers, followed by reoxidation of the interchain disulfide bonds.

WO/2009089004 discloses a method of preparing a heterodimeric protein by introduction of one or more charged amino acids mutation within the CH3-CH3 interface that are electrostatically unfavorable to homodimer formation but electrostatically favorable to heterodimer formation.

U.S. Pat. No. 5,173,168 describes a method for making heterodimeric IgGs using a "knobs-into-holes" strategy. A "knob" at the CH3 domain interface of the first chain is first created by replacing a smaller amino acid side chain with a larger one; and a hole in the CH3 interface of the second chain is generated by replacing a larger amino acid side chain with a smaller one. The "knob and hole" interaction favors heterodimeric IgGs formation and disfavor homodimeric formation.

WO/2012058768 discloses a method for the generation of heterodimeric IgG, resulting from mutations introduced in the IgG1 CH3 domain involving negative and positive designs along with structural and computational modeling guided protein engineering techniques.

Neonatal Fc receptor, FcRn, includes one transmembrane heavy chain (P51 subunit α chain) and one soluble light chain (P14 subunit β chain), both of which combine with noncovalent interactions, shares homology with the family of major histocompatibility complex I (MHC I) heterodimer receptors in structure. FcRn has several important biological functions. FcRn, as a transport receptor, combines with IgG and albumin and passes through a variety of cell barriers. For example, FcRn transfers maternal IgG antibodies into the fetus to offer neonatal humoral immunity during gestation. The pH-dependent interaction between FcRn and IgG and albumin is critical for prolonging serum half-life through cycle collection and degradation reduction of protein, as disclosed in Adv Drug Deliv Rev. Aug. 30, 2015; 91:109-24; J Immunol. May 15, 2015; 194 (10):4595-603; and Nat Rev Immunol. 2007 September; 7(9):715-25. The binding site of FcRn and IgG is in the interface between CH2 and CH3 domain and involves amino acid residues 253, 310, and 435, as disclosed in Immunol Rev. 2015 November; 268(1):253-68 and Mol Immunol. 2015 October; 67 (2 Pt A):131-41.

IV. SUMMARY OF THE INVENTION

The present disclosure relates to heterodimeric immunoglobulin constructs, e.g., bispecific antibodies, having modified constant regions leading to increased stability and specificity, as well as methods of production and methods of use thereof.

Accordingly, in a first aspect, the present disclosure is directed to a heterodimer comprising an Fc receptor (FcR)-binding member and one or more recognition moieties covalently linked to the FcR-binding member. The FcR-binding member comprises a first polypeptide and a second polypeptide joined to each other by one or more disulfide bonds. The first polypeptide and the second polypeptide each comprise at least a portion of an immunoglobulin heavy chain constant region. The first polypeptide and second polypeptide comprise at least five amino acid substitutions at the following positions:

1) 366 and 399 in the first polypeptide and 351, 407 and 409 in the second polypeptide; or
2) 366 and 409 in the first polypeptide and 351, 399 and 407 in the second polypeptide; whereby the first and second polypeptides have higher dimerization affinity for each other than self.

In some embodiments, the at least five amino acid substitutions comprise at least one of the following substitutions:

a) Glycine, tyrosine, valine, proline, aspartate, glutamate, lysine or tryptophan for L351 in the second polypeptide;

b) Leucine, proline, tryptophan or valine for T366 in the first polypeptide;

c) Cysteine, asparagine, isoleucine, glycine, arginine, threonine or alanine for D399 in the first polypeptide and/or the second polypeptide;

d) leucine, alanine, proline, phenylalanine, threonine or histidine for Y407 in the second polypeptide; and e) cysteine, proline, serine, phenylalanine, valine, glutamate or arginine for K409 in the first polypeptide and/or the second polypeptide.

In some embodiments, the at least five amino acid substitutions comprise any one of the following combinations of any one member from each of Group I a)-h) and Group II a)-h):

Group I:
a) T366L in the first polypeptide and L351E, Y407L in the second polypeptide;
b) T366L in the first polypeptide and L351G, Y407L in the second polypeptide;
c) T366L in the first polypeptide and L351Y, Y407A in the second polypeptide;
d) T366P in the first polypeptide and L351V, Y407P in the second polypeptide;
e) T366W in the first polypeptide and L351D, Y407P in the second polypeptide;
f) T366P in the first polypeptide and L351P, Y407F in the second polypeptide;
g) T366V in the first polypeptide and L351K, Y407T in the second polypeptide; and
h) T366L in the first polypeptide and L351W, Y407H in the second polypeptide.

Group II:
a) D399R in the first polypeptide and K409V in the second polypeptide;
b) D399C in the first polypeptide and K409C in the second polypeptide;
c) D399C in the first polypeptide and K409P in the second polypeptide;
d) D399N in the first polypeptide and K409S in the second polypeptide;
e) D399G in the first polypeptide and K409S in the second polypeptide;
f) D399I in the first polypeptide and K409F in the second polypeptide;
g) D399T in the first polypeptide and K409Q in the second polypeptide; and
h) D399 Å in the first polypeptide and K409R in the second polypeptide.

In some embodiments, the at least five amino acid substitutions comprise any one of the following combinations of any one member from each of Group III a)-h) and Group IV a)-h):

Group III:
a) T366L in the first polypeptide and L351E, Y407L in the second polypeptide;
b) T366L in the first polypeptide and L351G, Y407L in the second polypeptide;
c) T366L in the first polypeptide and L351Y, Y407A in the second polypeptide;
d) T366P in the first polypeptide and L351V, Y407P in the second polypeptide;
e) T66W in the first polypeptide and L351D, Y407P in the second polypeptide;
f) T366P in the first polypeptide and L351P, Y407F in the second polypeptide;
g) T366V in the first polypeptide and L351K, Y407T in the second polypeptide; and
h) T366L in the first polypeptide and L351W, Y407H in the second polypeptide.

Group IV:
a) K409V in the first polypeptide and D399R in the second polypeptide;
b) K409C in the first polypeptide and D399C in the second polypeptide;
c) K409P in the first polypeptide and D399C in the second polypeptide;
d) K409S in the first polypeptide and D399N in the second polypeptide;
e) K409S in the first polypeptide and D399G in the second polypeptide;
f) K409F in the first polypeptide and D399I in the second polypeptide;
g) K409Q in the first polypeptide and D399T in the second polypeptide; and
h) K409R in the first polypeptide and D399 Å in the second polypeptide.

In some embodiments, the at least five amino acid substitutions comprise any of the following members of Group V a)-h):

Group V:
a) T366L and D399R in the first polypeptide and L351E, Y407L and K409V in the second polypeptide;
b) T366L and D399C in the first polypeptide and L351G, Y407L and K409C in the second polypeptide;
c) T366L and D399C in the first polypeptide and L351Y, Y407A and K409P in the second polypeptide;
d) T366P and D399N in the first polypeptide and L351V, Y407P and K409S in the second polypeptide;
e) T366W and D399G in the first polypeptide and L351D, Y407P and K409S in the second polypeptide;
f) T366P and D399I in the first polypeptide and L351P, Y407F and K409F in the second polypeptide;
g) T366V and D399T in the first polypeptide and L351K, Y407T and K409Q in the second polypeptide; and
h) T366L and D399 Å in the first polypeptide and L351W, Y407H and K409R in the second polypeptide.

In some embodiments, the at least five amino acid substitutions comprise any of the following members of Group VI a)-h):

Group VI:
a) T366L and K409V in the first polypeptide and L351E, Y407L and D399R in the second polypeptide;
b) T366L and K409C in the first polypeptide and L351G, Y407L and D399C in the second polypeptide;
c) T366L and K409P in the first polypeptide and L351Y, Y407A and D399C in the second polypeptide;
d) T366P and K409S in the first polypeptide and L351V, Y407P and D399N in the second polypeptide;
e) T366W and K409S in the first polypeptide and L351D, Y407P and D399G in the second polypeptide;
f) T366P and K409F in the first polypeptide and L351P, Y407F and D399I in the second polypeptide;
g) T366V and K409Q in the first polypeptide and L351K, Y407T and D399T in the second polypeptide; and
h) T366L and K409R in the first polypeptide and L351W, Y407H and D399 Å in the second polypeptide.

In some embodiments, the at least five amino acid substitutions comprise T366L and D399R in the first polypeptide. In some embodiments, the at least five amino acid substitutions comprise L351E, Y407L and K409V in the second polypeptide. In some embodiments, the at least five amino acid substitutions comprise T366L and D399R in the first polypeptide and L351E, Y407L and K409V in the second polypeptide.

In some embodiments, the FcR-binding member comprises an Fc domain. In some embodiments, the Fc domain is derived from an IgG Fc domain. In some embodiments, the Fc domain is derived from one of an IgG1 Fc domain, an IgG2 Fc domain, an IgG3 Fc domain, and an IgG4 Fc domain.

In some embodiments, the FcR-binding member is capable of specifically binding to an Fc receptor. In some embodiments, the Fc receptor is a neonatal Fc receptor (FcRn). In some embodiments, the Fc receptor is one of FcγRI, FcγRIIA, FcγRIIB1, FcγRIIB2, FcγRIIIA, FcγRIIIB, FcεRI, FcεRII, FcαRI, Fcα/μR, FcRn, and combinations thereof. In some embodiments, binding to the Fc receptor triggers antibody-dependent cell-mediated cytotoxicity (ADCC).

In some embodiments, the sequence of at least one of the first polypeptide and the second polypeptide comprises one of SEQ ID NOs: 16-31, 33, 35, 37, 39, 41, 43, 45, 48, 49, 51, 53, 55, 57, 59, 61, 63, 68, 69, 70 and 71.

In some embodiments, the one or more recognition moieties covalently linked to the FcR-binding member comprise at least one of antigen-binding (Fab) fragment or fragments, single chain variable fragment or fragments (scFv), extracellular domains of membrane receptors, peptide ligands of cell membrane receptors, cytokines, and affinity tags. In some embodiments, the one or more recognition moieties comprise a Fab fragment and a scFv fragment. In some embodiments, the one or more recognition moieties comprise two scFv fragments. In some embodiments, the two scFv fragments are non-identical. In some embodiments, the one or more recognition moieties comprise two Fab fragments. In some embodiments, the two Fab fragments are non-identical. In some embodiments, the heterodimers comprise immunoglobulin (Ig)-like molecules having two non-identical Fab fragments.

In some embodiments, the one or more recognition moieties recognize HER2. In some embodiments, the one or more recognition moieties recognize PD-L1. In some embodiments, the one or more recognition moieties recognize Trop2. In some embodiments, the one or more recognition moieties recognize CD3. In some embodiments, the one or more recognition moieties recognize CD20.

In some embodiments, recognition comprises specific binding. In some embodiments, the one or more recognition moieties specifically bind to HER2. In some embodiments, the one or more recognition moieties specifically bind to PD-L1. In some embodiments, the one or more recognition moieties specifically bind to Trop2. In some embodiments, the one or more recognition moieties specifically bind to CD3. In some embodiments, the one or more recognition moieties specifically bind to CD20.

In some embodiments, the one or more recognition moieties comprise a pair of recognition moieties selected from Group VII a)-d) below:

Group VII:
  a) Fab specifically binding to HER2 and scFv specifically binding to CD3;
  b) Fab specifically binding to Trop2 and scFv specifically binding to CD3;
  c) Fab specifically binding to CD20 and scFv specifically binding to CD3; and
  d) Fab specifically binding to PD-L1 and scFv specifically binding to CD3.

In some embodiments, the one or more recognition moieties comprises a Fab specifically binding to HER2 and a Fab specifically binding to CD20.

In some embodiments, the heterodimers involve non-identical first heavy chains and non-identical second heavy chains, and non-identical first light chains and non-identical second light chains.

In another aspect, the present disclosure is directed to a method of producing a heterodimer. In some embodiments, the method comprises the steps of 1) expressing one or more nucleic acids encoding the first polypeptide in a first host cell and one or more nucleic acids encoding the second polypeptide in a second host cell, the first host cell and the second host cell being separated from one another; 2) reducing the first polypeptide and the second polypeptides while separated; 3) combining the first polypeptide and the second polypeptide to form a resultant mixture; 4) oxidizing the resultant mixture; and 5) recovering the formed heterodimer.

In another aspect, the present disclosure is directed to a method of producing a heterodimer, the heterodimer comprising a bivalent heterologous immunoglobulin having a non-identical first heavy chain and a second heavy chain, and a non-identical first light chain and a second light chain. In some embodiments, the method comprises the steps of 1) expressing one or more nucleic acids encoding the first heavy chain and the first light chain in a first host cell and one or more nucleic acids encoding the second heavy chain and the second light chain in a second host cell, the first host cell and the second host cell being separated from one another; 2) reducing the first heavy chain and first light chain together and the second heavy chain and second light chain together; 3) combining the first heavy chain, first light chain, second heavy chain, and second light chain to form a resultant mixture; 4) oxidizing the resultant mixture; and 5) recovering the formed heterodimer. In some embodiments, the first heavy chain and the second heavy chain form an Fc region of the bivalent heterologous immunoglobulin.

In some embodiments, the Fc region comprises at least five amino acid substitutions, the at least five amino acid substitutions comprise any one of the following combinations of any one member from each of Group VIII a)-h) and Group IX a)-h):

Group VIII:
  a) T366L in the first heavy chain and L351E, Y407L in the second heavy chain;
  b) T366L in the first heavy chain and L351G, Y407L in the second heavy chain;
  c) T366L in the first heavy chain and L351Y, Y407A in the second heavy chain;
  d) T366P in the first heavy chain and L351V, Y407P in the second heavy chain;
  e) T366W in the first heavy chain and L351D, Y407P in the second heavy chain;
  f) T366P in the first heavy chain and L351P, Y407F in the second heavy chain;
  g) T366V in the first heavy chain and L351K, Y407T in the second heavy chain; and
  h) T366L in the first heavy chain and L351W, Y407H in the second heavy chain.

Group IX:
  a) D399R in the first heavy chain and K409V in the second heavy chain;
  b) D399C in the first heavy chain and K409C in the second heavy chain;
  c) D399C in the first heavy chain and K409P in the second heavy chain;

d) D399N in the first heavy chain and K409S in the second heavy chain;
e) D399G in the first heavy chain and K409S in the second heavy chain;
f) D399I in the first heavy chain and K409F in the second heavy chain;
g) D399T in the first heavy chain and K409Q in the second heavy chain; and
h) D399 Å in the first heavy chain and K409R in the second heavy chain.

In some embodiments, the at least five amino acid substitutions comprise any one of the following members from Group X a)-h):

Group X:
a) T366L and D399R in the first heavy chain and L351E, Y407L and K409V in the second heavy chain;
b) T366L and D399C in the first heavy chain and L351G, Y407L and K409C in the second heavy chain;
c) T366L and D399C in the first heavy chain and L351Y, Y407A and K409P in the second heavy chain;
d) T366P and D399N in the first heavy chain and L351V, Y407P and K409S in the second heavy chain;
e) T366W and D399G in the first polypeptide and L351D, Y407P and K409S in the second heavy chain;
f) T366P and D399I in the first polypeptide and L351P, Y407F and K409F in the second heavy chain
g) T366V and D399T in the first heavy chain and L351K, Y407T and K409Q in the second heavy chain; and
h) T366L and D399 Å in the first heavy chain and L351W, Y407H and K409R in the second heavy chain.

In some embodiments, the at least five amino acid substitutions comprise any one of the following members from Group XI a)-h):

Group XI:
a) T366L and K409V in the first heavy chain and L351E, Y407L and D399R in the second heavy chain;
b) T366L and K409C in the first heavy chain and L351G, Y407L and D399C in the second heavy chain;
c) T366L and K409P in the first heavy chain and L351Y, Y407A and D399C in the second heavy chain;
d) T366P and K409S in the first heavy chain and L351V, Y407P and D399N in the second heavy chain;
e) T366W and K409S in the first heavy chain and L351D, Y407P and D399G in the second heavy chain;
f) T366P and K409F in the first heavy chain and L351P, Y407F and D399I in the second heavy chain;
g) T366V and K409Q in the first heavy chain and L351K, Y407T and D399T in the second heavy chain; and
h) T366L and K409R in the first heavy chain and L351W, Y407H and D399 Å in the second heavy chain.

In another aspect, the present disclosure is directed to a method of producing a heterodimer, the heterodimer comprising an immunoglobulin heterodimer comprising a non-identical first heavy chain and a second heavy chain, and a non-identical first light chain and a second light chain. In some embodiments, the method comprises the steps of: 1) expressing one or more nucleic acids encoding the first heavy chain and the first light chain in a first host cell and one or more nucleic acids encoding the second heavy chain and the second light chain in a second host cell, the first host cell and the second host cell being separated from one another; 2) reducing the first heavy chain and first light chain together and the second heavy chain and second light chain together; 3) combining the first heavy chain, first light chain, second heavy chain, and second light chain to form a resultant mixture; 4) oxidizing the resultant mixture; and 5) recovering the formed heterodimer. In some embodiments, the first heavy chain and the second heavy chain form an Fc region of the bivalent heterologous immunoglobulin.

In some embodiments, the Fc domain comprises at least five amino acid substitutions, the at least five amino acid substitutions comprising any one of the following combinations of any one member from each of Group XII a)-h) and Group XIII a)-h):

Group XII:
a) T366L in the first heavy chain and L351E, Y407L in the second heavy chain;
b) T366L in the first heavy chain and L351G, Y407L in the second heavy chain;
c) T366L in the first heavy chain and L351Y, Y407A in the second heavy chain;
d) T366P in the first heavy chain and L351V, Y407P in the second heavy chain;
e) T366W in the first heavy chain and L351D, Y407P in the second heavy chain;
f) T366P in the first heavy chain and L351P, Y407F in the second heavy chain;
g) T366V in the first heavy chain and L351K, Y407T in the second heavy chain; and
h) T366L in the first heavy chain and L351W, Y407H in the second heavy chain.

Group XIII:
a) K409V in the first heavy chain and D399R in the second heavy chain;
b) K409C in the first heavy chain and D399C in the second heavy chain;
c) K409P in the first heavy chain and D399C in the second heavy chain;
d) K409S in the first heavy chain and D399N in the second heavy chain;
e) K409S in the first heavy chain and D399G in the second heavy chain;
f) K409F in the first heavy chain and D399I in the second heavy chain;
g) K409Q in the first heavy chain and D399T in the second heavy chain; and
h) K409R in the first heavy chain and D399 Å in the second heavy chain.

In another aspect, the present disclosure is directed to a method of producing a heterodimer, the heterodimer comprising a bivalent heterologous protein comprising a heavy chain, a light chain, and an scFv fragment linked to an Fc chain, wherein a portion of the heavy chain and the Fc chain linked to the scFv fragment forming an Fc region. In some embodiments, the method comprises the steps of 1) expressing one or more nucleic acids encoding the heavy chain, the light chain, and one or more nucleic acids encoding the scFv fragment linked to the Fc chain in a host cell; and 2) recovering the formed heterodimer.

In some embodiments, the Fc region comprises at least five amino acid substitutions, the at least five amino acid substitutions comprising any one of the following combinations of any one member from each of Group XIV a)-h) and Group XV a)-h):

Group XIV:
a) T366L in the first heavy chain and L351E, Y407L in the second heavy chain;
b) T366L in the first heavy chain and L351G, Y407L in the second heavy chain;
c) T366L in the first heavy chain and L351Y, Y407A in the second heavy chain;
d) T366P in the first heavy chain and L351V, Y407P in the second heavy chain;

e) T366W in the first heavy chain and L351D, Y407P in the second heavy chain;

f) T366P in the first heavy chain and L351P, Y407F in the second heavy chain;

g) T366V in the first heavy chain and L351K, Y407T in the second heavy chain; and h) T366L in the first heavy chain and L351W, Y407H in the second heavy chain.

Group XV:

a) D399R in the first heavy chain and K409V in the second heavy chain;

b) D399C in the first heavy chain and K409C in the second heavy chain;

c) D399C in the first heavy chain and K409P in the second heavy chain;

d) D399N in the first heavy chain and K409S in the second heavy chain;

e) D399G in the first heavy chain and K409S in the second heavy chain;

f) D399I in the first heavy chain and K409F in the second heavy chain;

g) D399T in the first heavy chain and K409Q in the second heavy chain; and h) D399 Å in the first heavy chain and K409R in the second heavy chain.

In some embodiments, the at least five amino acid substitutions comprise any one of the following combinations of any one member from each of Group XVI a)-h) and Group XVII a)-h):

Group XVI:

a) T366L in the first heavy chain and L351E, Y407L in the second heavy chain;

b) T366L in the first heavy chain and L351G, Y407L in the second heavy chain;

c) T366L in the first heavy chain and L351Y, Y407A in the second heavy chain;

d) T366P in the first heavy chain and L351V, Y407P in the second heavy chain;

e) T366W in the first heavy chain and L351D, Y407P in the second heavy chain;

f) T366P in the first heavy chain and L351P, Y407F in the second heavy chain;

g) T366V in the first heavy chain and L351K, Y407T in the second heavy chain; or h) T366L in the first heavy chain and L351W, Y407H in the second heavy chain.

Group XVII:

a) K409V in the first heavy chain and D399R in the second heavy chain;

b) K409C in the first heavy chain and D399C in the second heavy chain;

c) K409P in the first heavy chain and D399C in the second heavy chain;

d) K409S in the first heavy chain and D399N in the second heavy chain;

e) K409S in the first heavy chain and D399G in the second heavy chain;

f) K409F in the first heavy chain and D399I in the second heavy chain;

g) K409Q in the first heavy chain and D399T in the second heavy chain; and h) K409R in the first heavy chain and D399 Å in the second heavy chain.

In some embodiments of the aspects relating to methods of producing a heterodimer, the nucleic acids are located on a vector or a system of vectors. In some embodiments, the vector or system of vectors comprises plasmid vector(s) pX0GC modified from pCDNA vector(s).

In some embodiments of the aspects relating to methods of producing a heterodimer, the host cells comprise human embryonic kidney cells (HEK293) or HEK293T, HEK293E, HEK293F modified from HEK293, Chinese hamster ovary cells (CHO), CHO—S, CHO-dhfr⁻, CHO/DG44, ExpiCHO modified from CHO, and a combination thereof.

In some embodiments of the aspects relating to methods of producing a heterodimer, the steps involving reducing or reduction involve one or more reduction agents comprising at least one of 2-Aminoethanethiol, Dithiothreitol, TRIS™-(2-carboxyethyl)-phosphine hydrochloride, chemical derivatives thereof, and combinations thereof. In some embodiments, the methods further comprise reduction at about 2-8° C., e.g., 3-6° C. and 4° C., optionally for a time period of about at least 3 hours (e.g., 3-8 hours, 4-7 hours, and 5-6 hours). In yet further embodiments, the methods involve removal of the one or more reduction agents. In some embodiments, removing the one or more reduction agents involves a desalting method.

In some embodiments of the aspects relating to methods of producing a heterodimer, the steps involving oxidation or oxidizing involve one or more oxidizing agents comprising at least one of L-dehydroascorbic acid, chemical derivatives thereof, and combinations thereof. In some embodiments, the methods further comprise oxidation at about 2-8° C., e.g., 3-6° C. and 4° C., optionally for a time period of at least about 5 hours (e.g., 5 hours to 4 days, 5 hours to 3 days, 5 hours to 1 day). In some embodiments, the method further comprises recovery and/or purification.

In another aspect, the present disclosure is directed to nucleic acids encoding a portion of a heterodimer according to any aspect of the present disclosure. In some embodiments, the nucleic acid sequence comprises one of SEQ ID NOs: 32, 34, 36, 38, 40, 42, 44, 46, 47, 50, 52, 54, 56, 58, 60, 62, and 64-67, or a sequence having at least 70%, e.g., at least 75%, 80%, 85%, 90%, 95%, 96%, 97%, 98%, 99%, 99.1%, 99.2%, 99.3%, 99.4%, 99.5%, 99.6%, 99.7%, 99.8%, or at least 99.9% sequence identity with one or more of SEQ ID NOs: 32, 34, 36, 38, 40, 42, 44, 46, 47, 50, 52, 54, 56, 58, 60, 62, and 64-67. In some embodiments, the nucleic acid sequence comprises a sequence which will hybridize with one or more of SEQ ID NOs: 32, 34, 36, 38, 40, 42, 44, 46, 47, 50, 52, 54, 56, 58, 60, 62, and 64-67 under stringent conditions. In some embodiments, the nucleic acid sequence comprises a sequence which is complementary to one or more of SEQ ID NOs: 32, 34, 36, 38, 40, 42, 44, 46, 47, 50, 52, 54, 56, 58, 60, 62, and 64-67.

In another aspect, the present disclosure is directed to a vector or system of vectors which comprises at least one nucleic acid encoding a portion of a heterodimer according to any aspect of the present disclosure. In some embodiments, the vector or system of vectors comprise plasmid vector(s) pX0GC modified from pCDNA vector(s).

In another aspect, the present disclosure is directed to a host cell containing a vector or system of vectors which comprises any nucleic acid encoding a portion of a heterodimer according to any aspect of the present disclosure. In some embodiments, the host cell is one of human embryonic kidney cells (HEK293) or HEK293T, HEK293E, HEK293F modified from HEK293, Chinese hamster ovary cells (CHO), CHO—S, CHO-dhfr⁻, CHO/DG44, and ExpiCHO modified from CHO cells.

In another aspect, the present disclosure is directed to a method of recombinantly producing a portion of a heterodimer according to any aspect of the present disclosure. In some embodiments, the method involves providing a host cell containing a vector or system of vectors which comprises one or more nucleic acids encoding at least a first heavy chain and a second heavy chain of a heterodimer according to any aspect of the present disclosure, expressing the nucleic acids, and recovering the recombinantly produced heterodimer.

In another aspect, the present disclosure is directed to a composition comprising a heterodimer described above and a pharmaceutically acceptable carrier, preservative, or excipient.

In another aspect, the present disclosure is directed to a method of administering a heterodimer described above to a subject in need thereof. In some embodiments, the subject is administered the heterodimer to treat a disease or condition. In other embodiments, the subject is administered the heterodimer to prevent a disease or condition. In some embodiments, the subject is mammalian. In some embodiments, the subject is a human.

In some embodiments, the disease or condition comprises at least one of autoimmune diseases, immune response against grafts, allergic reactions, infections, neurodegenerative diseases, neoplastic diseases and cellular proliferative disorders, or combinations thereof. In some embodiments, the autoimmune diseases comprise at least one of arthritis, rheumatoid arthritis, psoriasis, multiple sclerosis (MS), ulcerative colitis, Crohn's disease, systemic lupus erythematosus (SLE), glomerulonephritis, dilated cardiomyopathy-like diseases, Sjogren's syndrome, allergic contact dermatitis, polymyositis, scleroderma, periarteritisnodosa, rheumatic fever, vitiligo, insulin-dependent diabetes mellitus, Behcet's syndrome, chronic thyroiditis, and combinations thereof. In some embodiments, the neurodegenerative diseases comprise at least one of Parkinson's disease, Huntington's disease, Machado-Joseph disease, amyotrophic lateral sclerosis (ALS), Creutzfeldt-Jakob disease, and combinations thereof. In some embodiments, theneoplastic diseases and cellular proliferative disorders comprise at least one of leukemia, lymphoma, myeloma, brain tumors, head and neck squamous cell carcinoma, non-small cell lung cancer (NSCLC), nasopharyngeal cancer, esophageal cancer, stomach cancer, pancreatic cancer, gallbladder cancer, liver cancer, colorectal cancer, breast cancer, ovarian cancer, cervical cancer, endometrial cancer, uterine sarcoma, prostate cancer, bladder cancer, renal cell carcinoma, melanoma, and combinations thereof.

In another aspect, the present disclosure is directed to a heterodimer as described above for use in medicine.

In another aspect, the present disclosure is directed to a heterodimer for use in treatment of a disease or condition. In some embodiments, the disease or condition comprises at least one of autoimmune diseases, immune response against grafts, allergic reactions, infections, neurodegenerative diseases, neoplastic diseases and cellular proliferative disorders, or combinations thereof.

In another aspect, the present disclosure is directed to use of a heterodimer as described above for the manufacture of a medicament.

In another aspect, the present disclosure is directed to use of a heterodimer as described above for the manufacture of a medicament for treatment of a disease or condition. In some embodiments, the heterodimer is a heterodimer according to any aspect of the present disclosure. In some embodiments, the disease or condition comprises at least one of autoimmune diseases, immune response against grafts, allergic reactions, infections, neurodegenerative diseases, neoplastic diseases and cellular proliferative disorders, or combinations thereof.

V. BRIEF DESCRIPTION OF THE FIGURES

FIG. 1 represents an exemplary pDis3 vector. Cmv is Cytomegalovirus promoter, sp is signal peptide, SUMO is Small ubiquitin-related modifier tag, Fc is fragment crystallizable, BGH is bovine growth hormone polyadenylation (bgh-PolyA) signal, HA is Human influenza hemagglutinin, PUC ori is origin of replication of pUC, Hydroishygromycin B resistant gene, AmpR is ampicillin resistant gene, oriP is the Epstein-Barr Virus replication origin.

(FIG. 8A), 1 mg/mL, 40° C. (FIG. 8B).

Figure 10B:
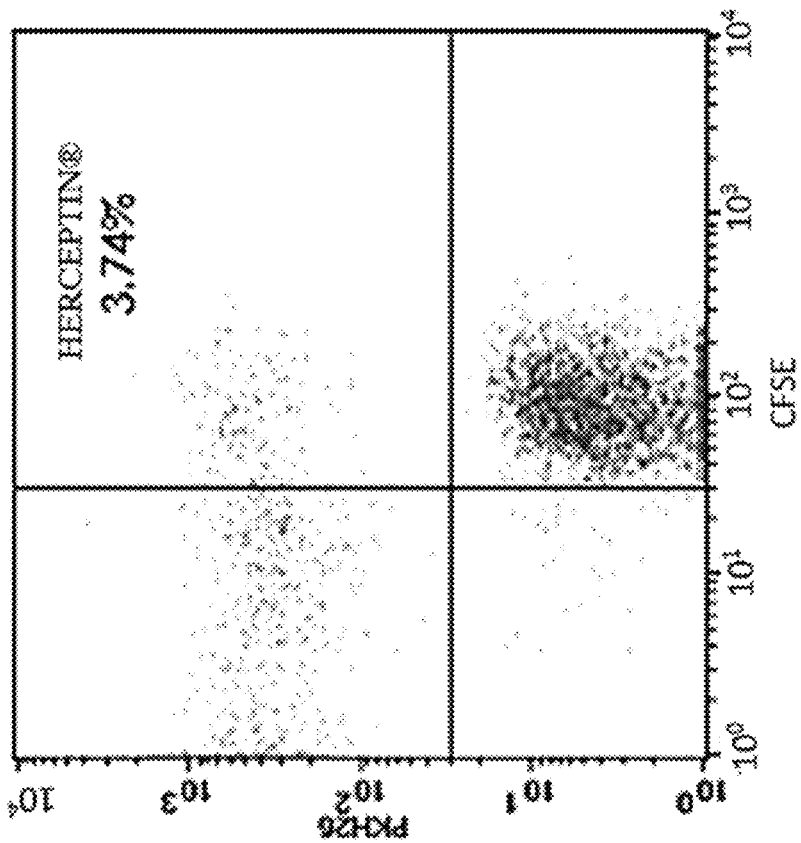
Figure 10A:
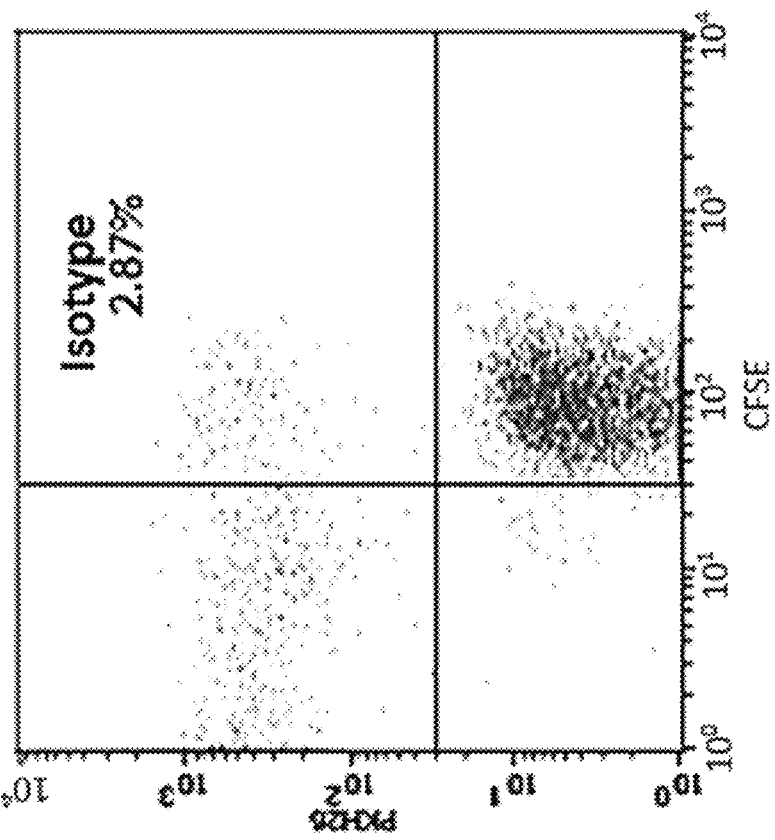
Figure 10D:
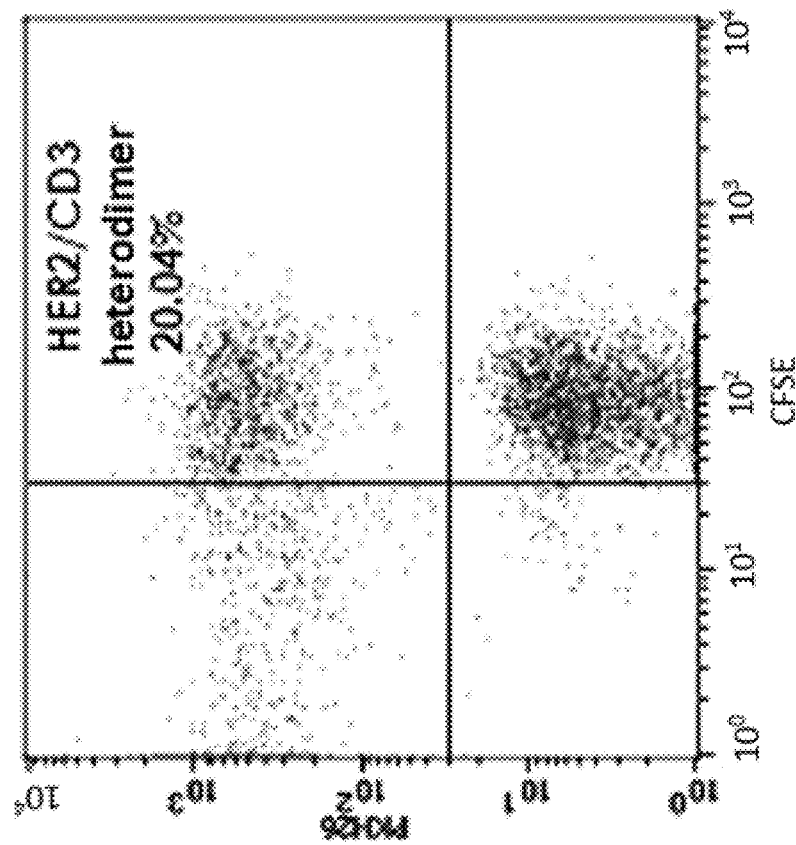
Figure 10C:
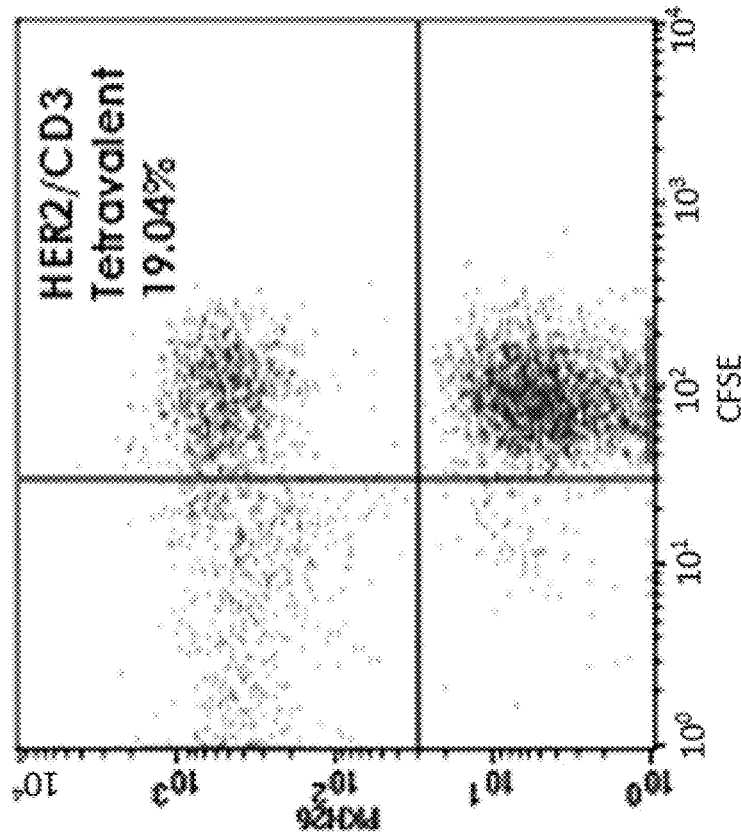

FIGS. 10A, 10B, 10C, and 10D represent simultaneous binding of the anti-HER2/anti CD3-scFv heterodimer to SK-BR-3 and Jurkat: Isotype (FIG. 10A), Anti-HER2 mAb (FIG. 10B), Anti-HER2/CD3 tetravalent homodimeric BsAb (FIG. 10C), Anti-HER2/CD3 bivalent heterodimeric BsAb (FIG. 10D).

Figure 11A:
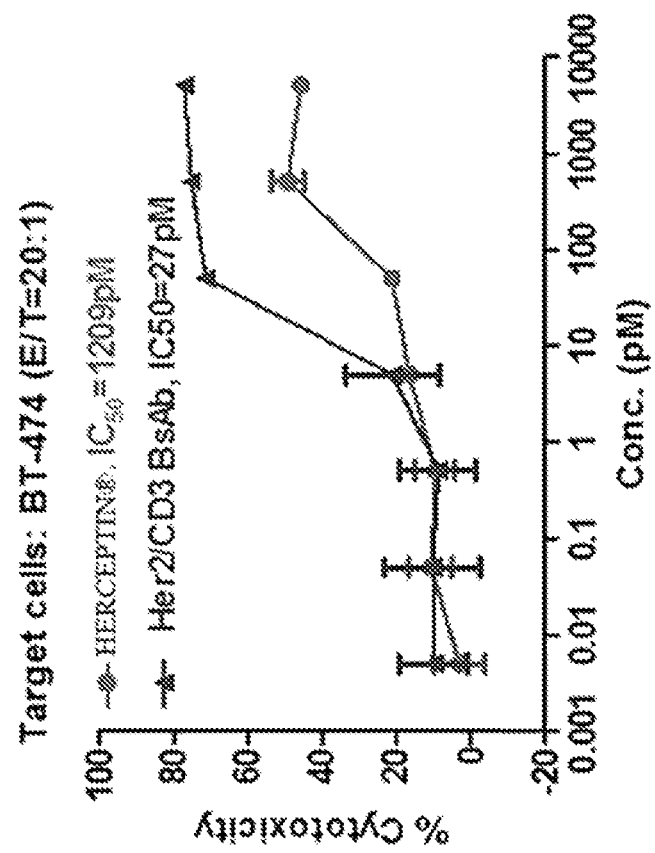
Figure 11B:
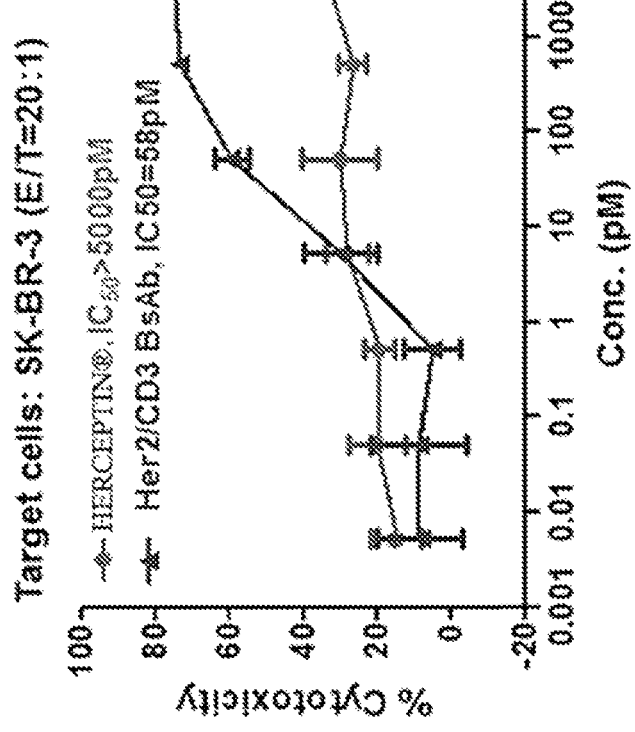

FIGS. 11A and 11B represent in-vitro cytotoxicity of the anti-HER2/anti CD3-scFv heterodimer in different target cells: SK—BR 3 (FIG. 11A), BT-474 (FIG. 11B).

Figure 12:
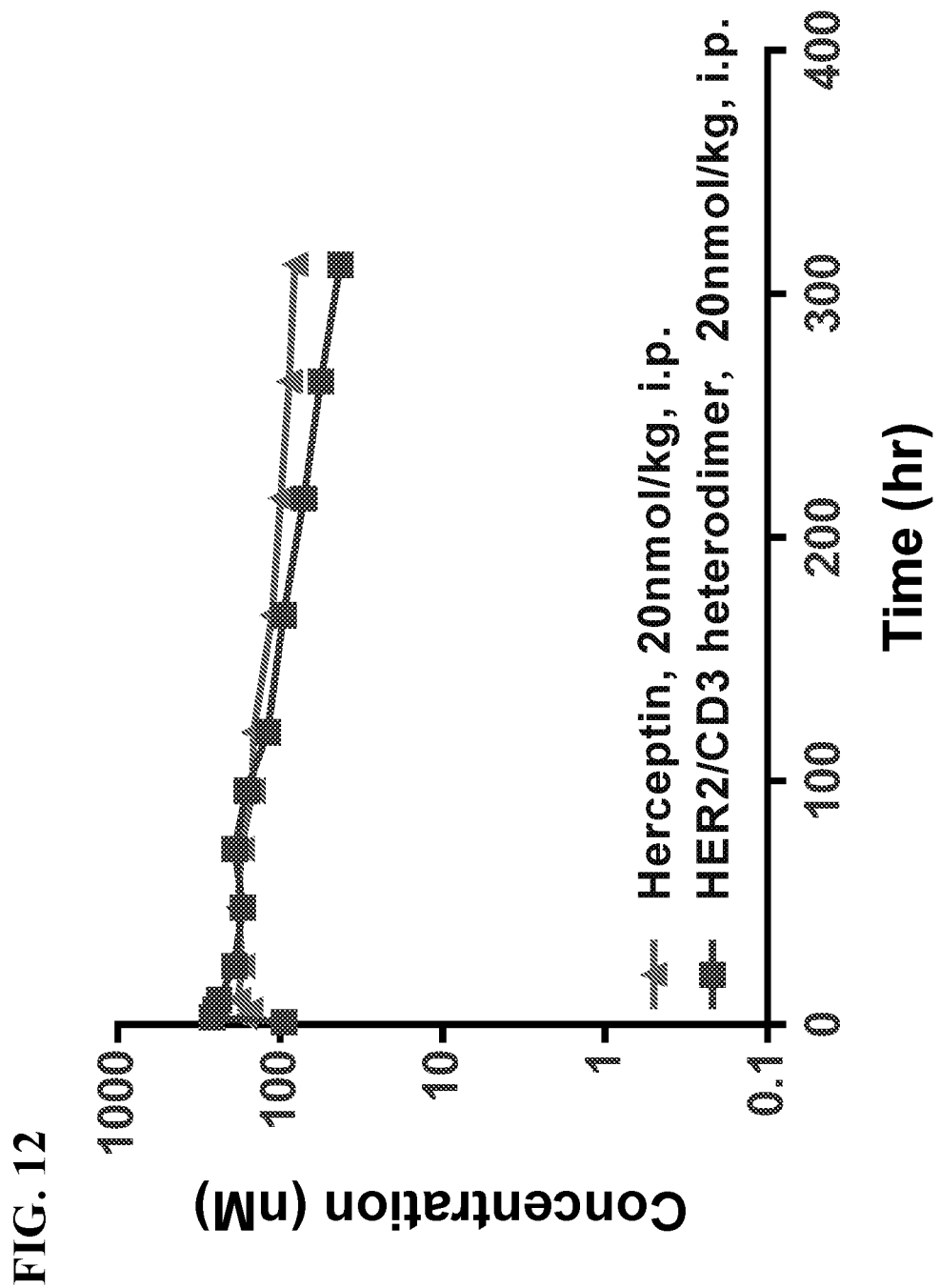

FIG. 12 represents one-dose pharmacokinetic (PK) profile of the anti-HER2/anti CD3-scFv heterodimer administered via i.p.

Figure 13:
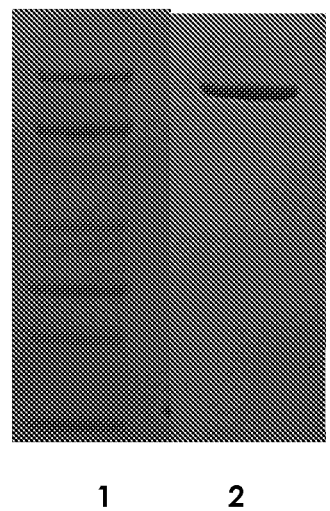

FIG. 13 represents an SDS-PAGE analysis of the anti-Trop2/anti CD3-scFv heterodimer.

Figure 14:
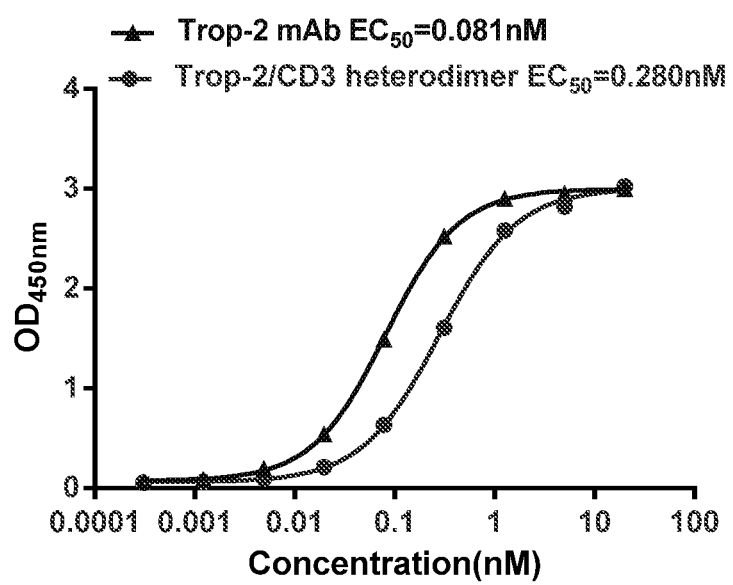

FIG. 14 represents Trop-2 binding affinity of the anti-Trop2/anti CD3-scFv heterodimer.

Figure 15A:
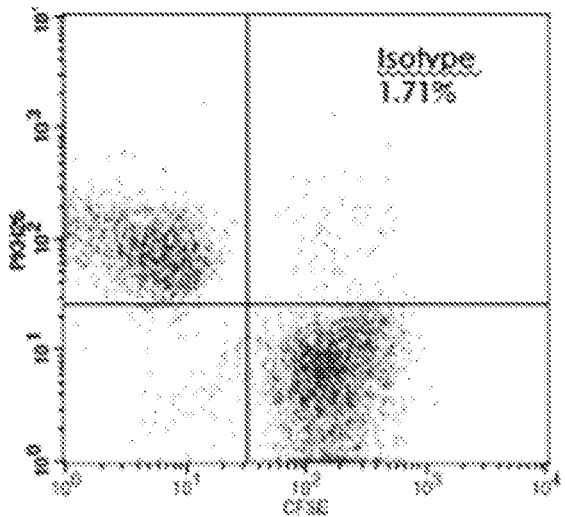
Figure 15B:
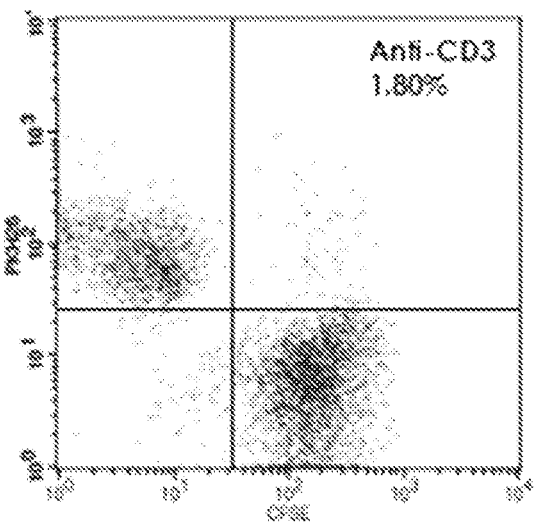
Figure 15C:
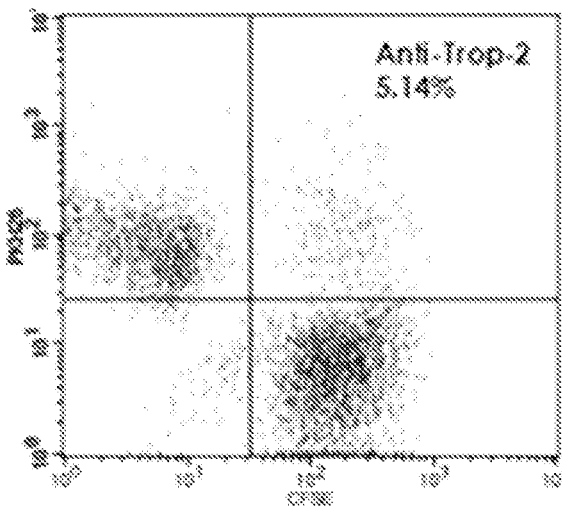
Figure 15D:
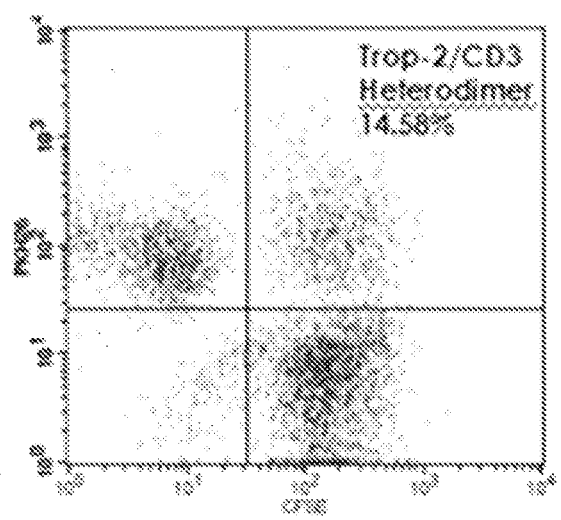

FIGS. 15A, 15B, 15C, and 15D represent simultaneous binding of anti-Trop2/anti CD3-scFv heterodimer to BxPC-3 and Jurkat: Isotype (FIG. 15A), Anti-CD3 mAb (FIG. 15B), Anti-Trop-2 mAb (FIG. 15C), Anti-Trop-2/CD3 heterodimeric BsAb (FIG. 15D).

Figure 16A:
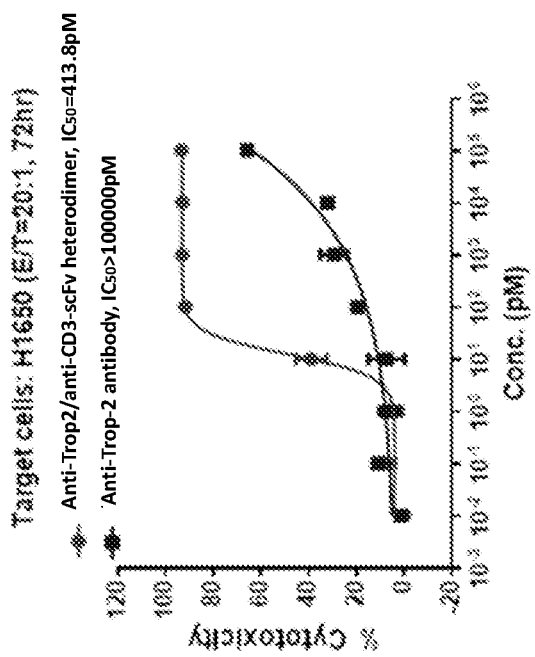
Figure 16B:
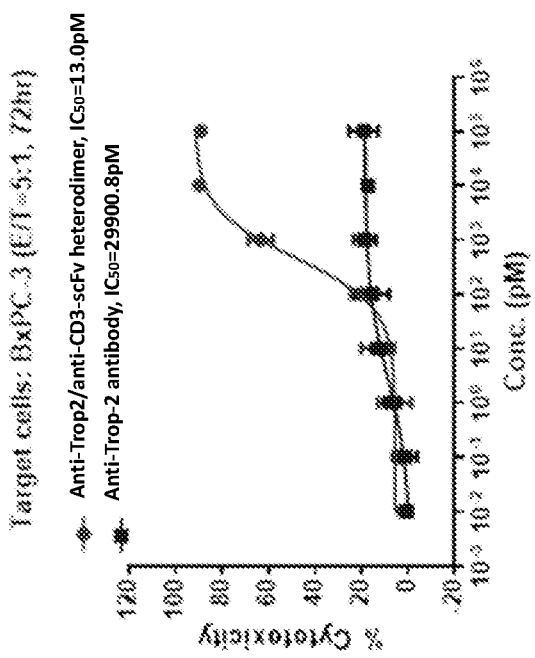

FIGS. 16A and 16B represent in-vitro cytotoxicity of the anti-Trop2/anti CD3-scFv heterodimer: H1650 (FIG. 16A) and BxPC-3 (FIG. 16B).

Figure 17:
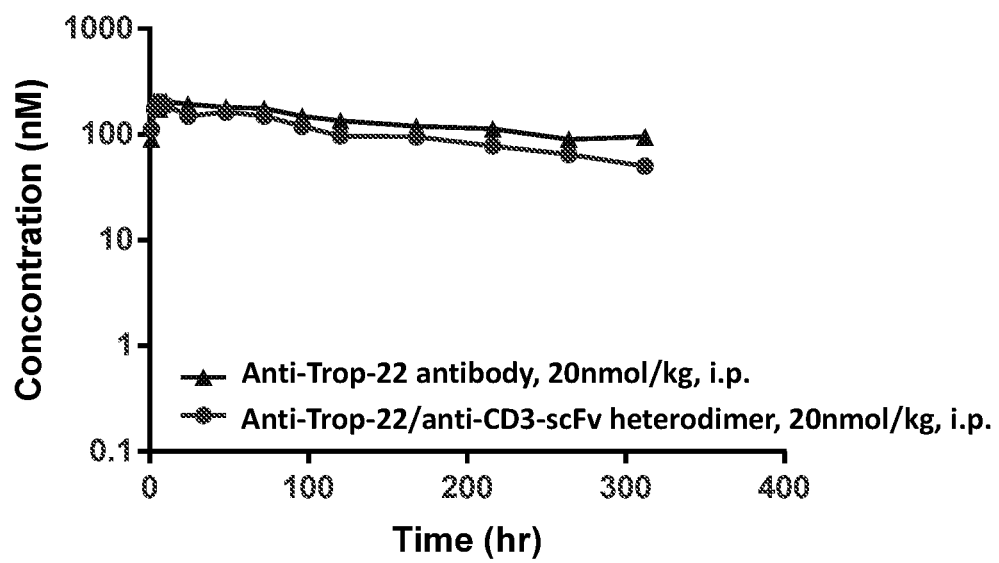

FIG. 17 represents one-dose pharmacokinetic (PK) profile of the anti-Trop2/anti CD3-scFv heterodimer administered via i.p.

Figure 18:
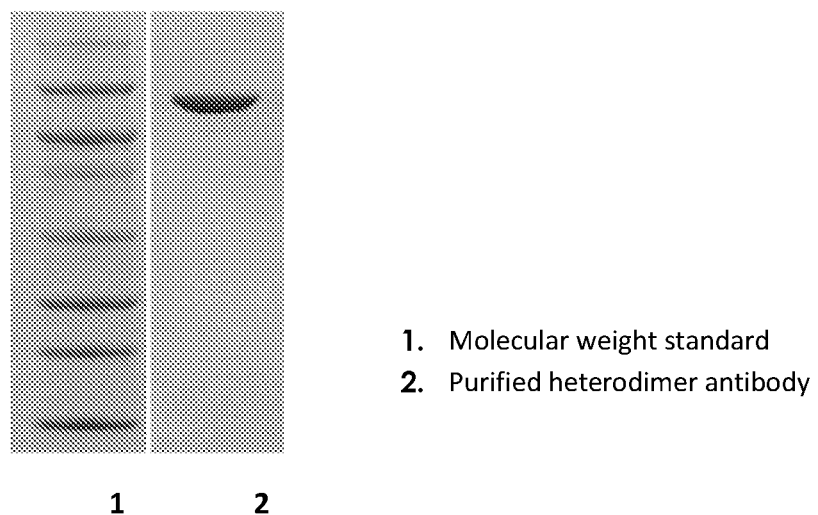

FIG. 18 represents an SDS-PAGE analysis of the anti-CD20/anti CD3-scFv heterodimer.

Figure 19A:
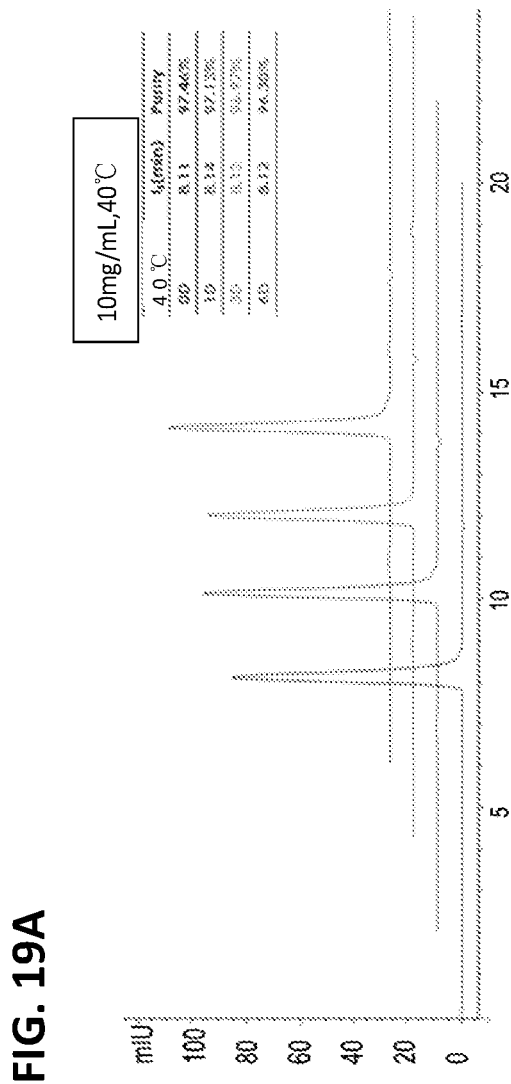
Figure 19B:
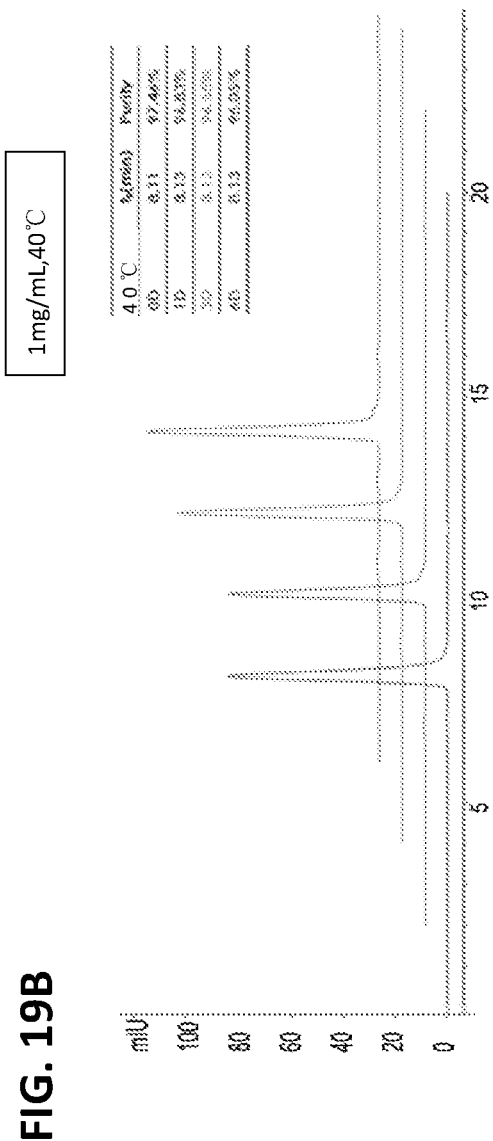

FIGS. 19A and 19B represent stability of the anti-CD20/anti CD3-scFv heterodimer at different concentrations: 10 mg/mL 40° C. (FIG. 19A), 1 mg/mL, 40° C. (FIG. 19B).

Figure 20:
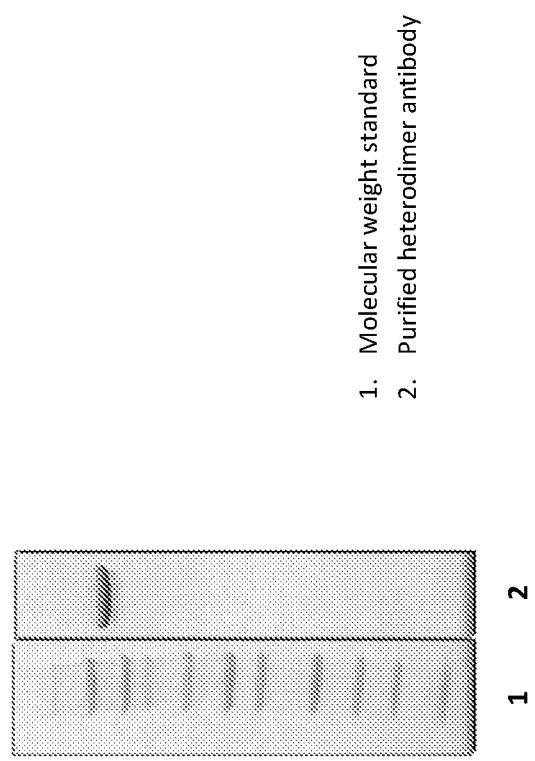

FIG. 20 represents an SDS-PAGE analysis of the anti-PD-L1/anti CD3-scFv heterodimer.

Figure 21:
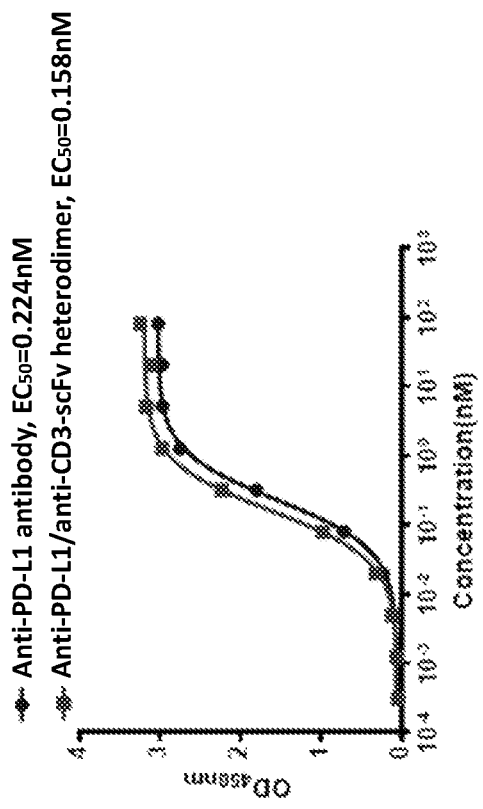

FIG. 21 represents the PD-L1 binding affinity of the anti-PD-L1/anti CD3-scFv heterodimer.

FIGS. 22A, 22B, 22C, and 22D represent simultaneous binding of anti-PD-L1/anti CD3-scFv heterodimer to H460 and Jurkat: Isotype (FIG. 22A), Anti-PD-L1 mAb (FIG.

22B), Anti-CD3 mAb (FIG. 22C), Anti-PD-L1/CD3 heterodimeric BsAb (FIG. 22D).

Figure 23A:
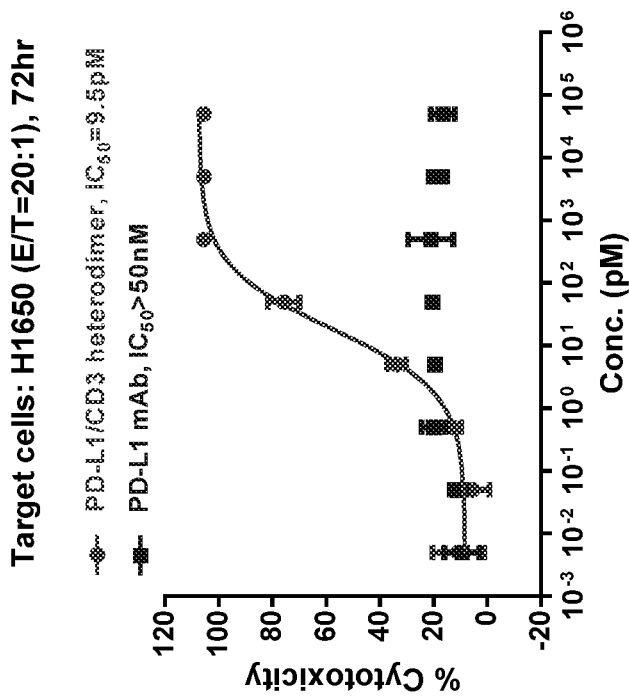
Figure 23B:
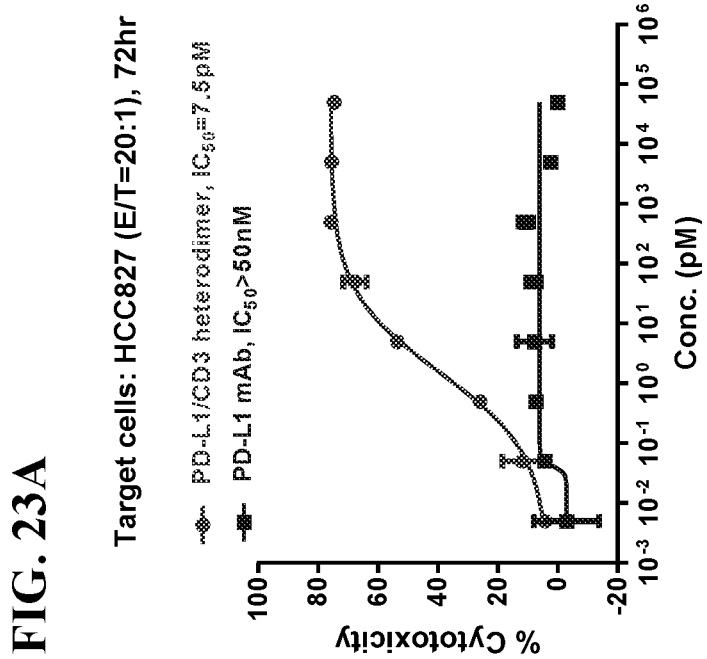

FIGS. 23A and 23B represent in-vitro cytotoxicity of the anti-PD-L1/anti CD3-scFv heterodimer in different cells: HCC827 (FIG. 23A), H1650 (FIG. 23B).

Figure 24:
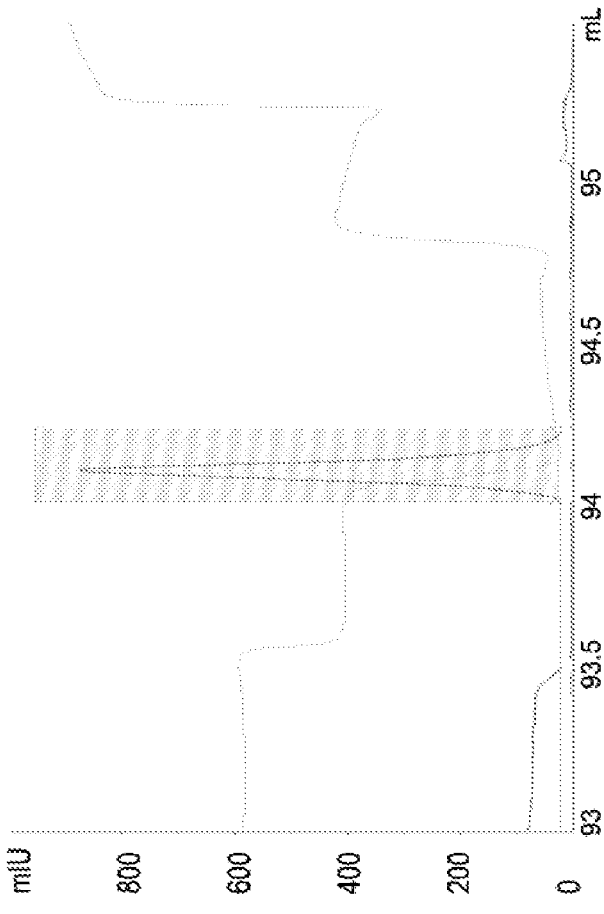

FIG. 24 represents an elution peak of the anti-CD20 expression products.

Figure 25:
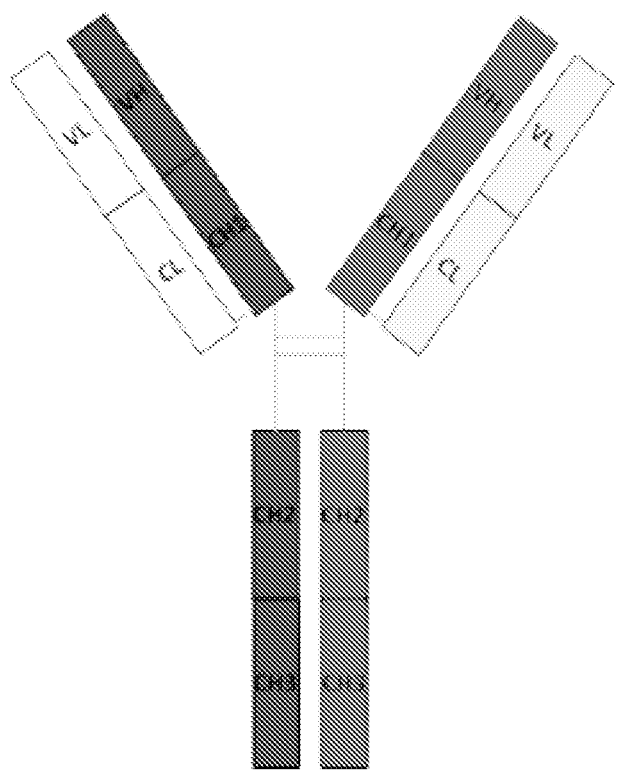

FIG. 25 represents the generic structure of an anti-HER2/anti-CD20 heterodimer.

Figure 26:
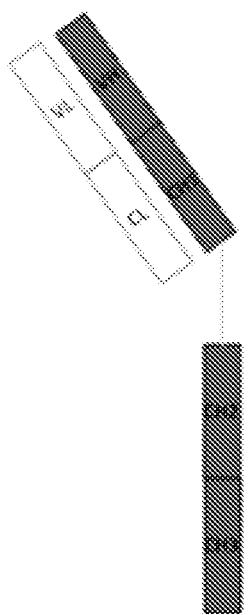

FIG. 26 represents the generic structure of a halfmer.

Figure 27:
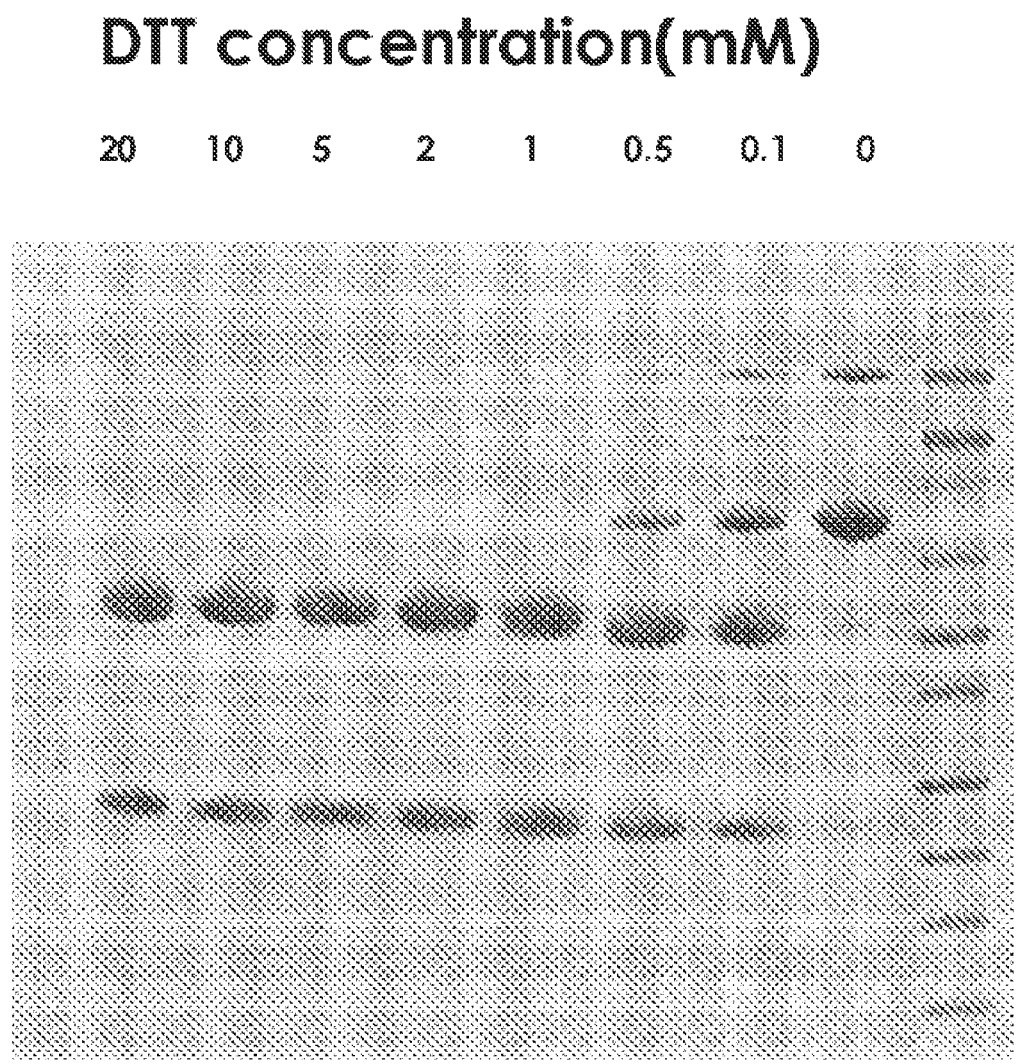

FIG. 27 represents an SDS-PAGE analysis of reduction product.

Figure 28A:
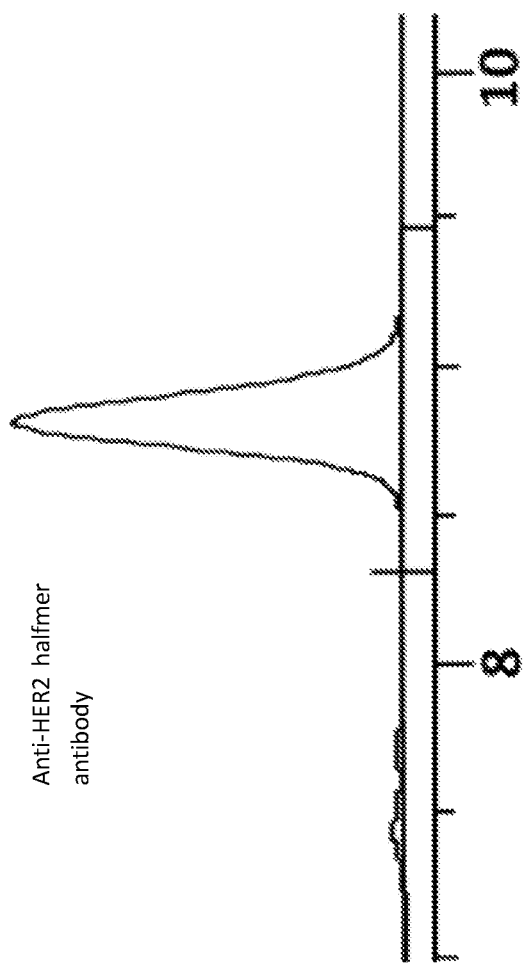
Figure 28B:
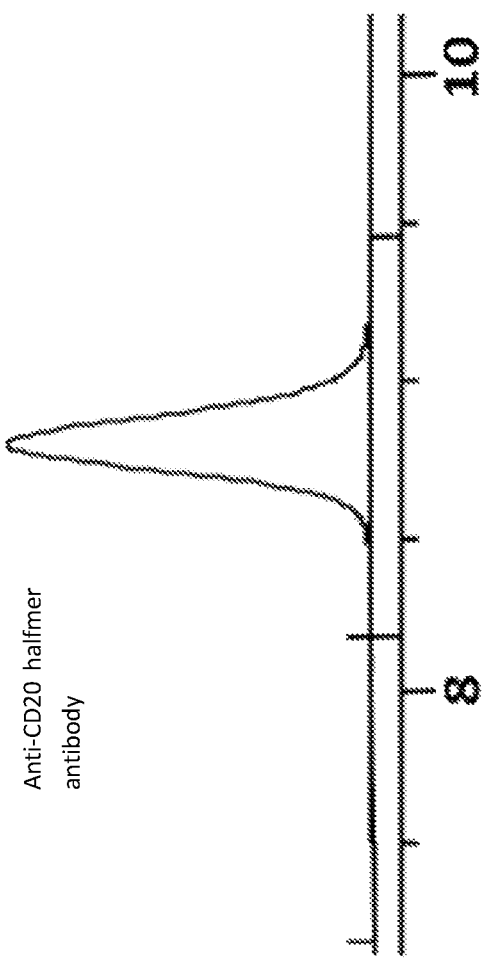

FIG. 28 represents a size exclusion-high performance liquid chromatography (SEC-HPLC) analysis of the reduction product.

Figure 29:
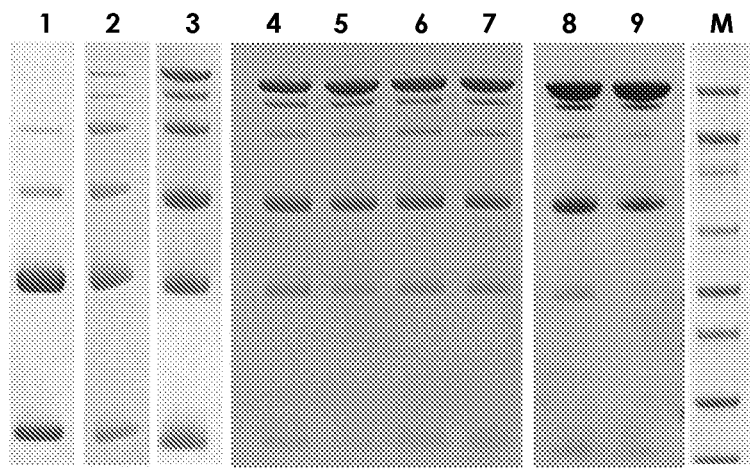

FIG. 29 represents an SDS-PAGE analysis of oxidization product.

Figure 30:
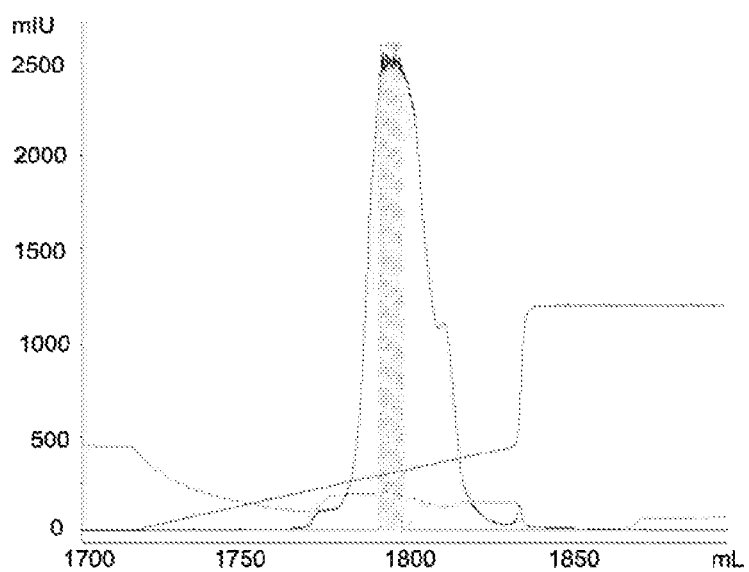

FIG. 30 represents an elution peak of anti-HER2/anti-CD20 heterodimer.

Figure 31:
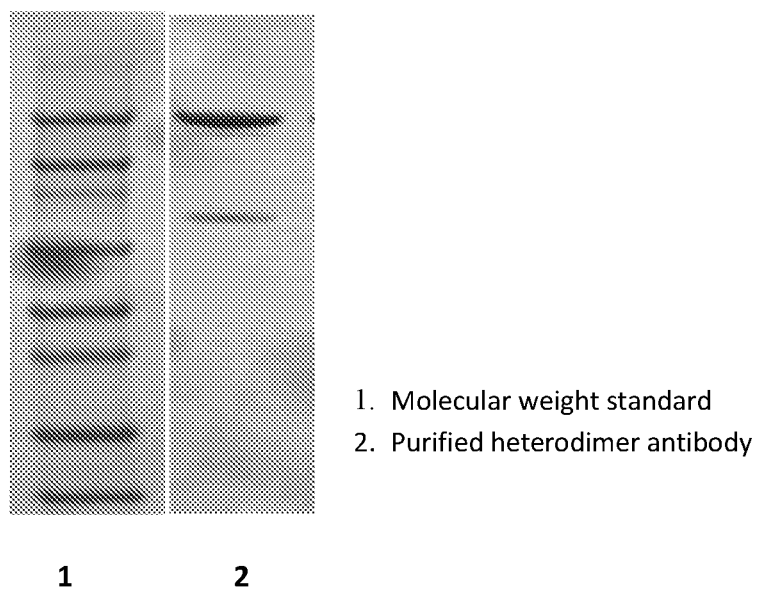

FIG. 31 represents an SDS-PAGE analysis of the anti-HER2/anti-CD20 heterodimer.

Figure 32:
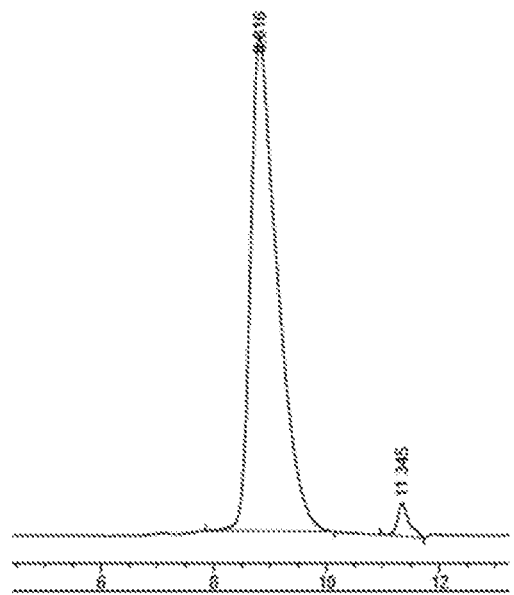

FIG. 32 represents results of a purity test of the anti-HER2/anti-CD20 heterodimer.

Figure 33:
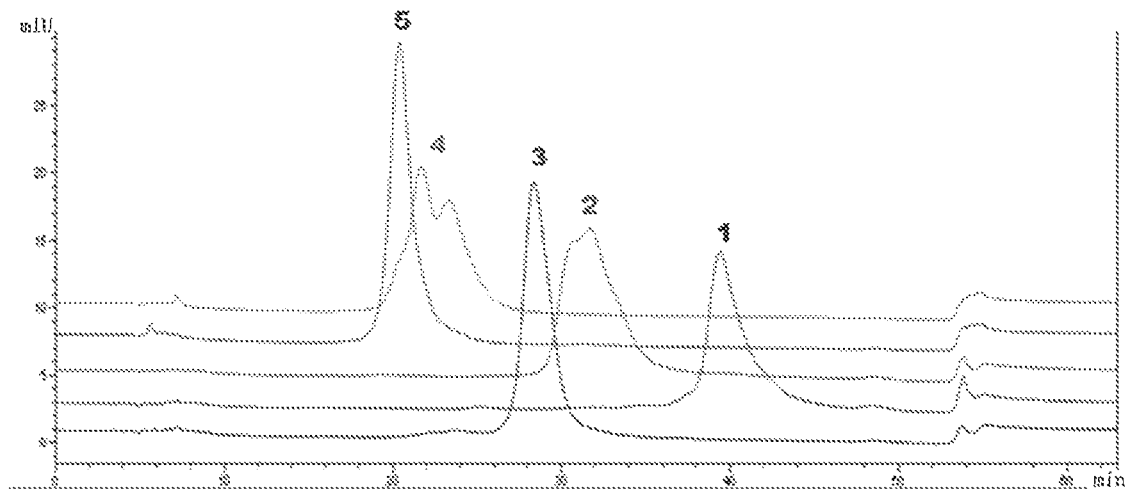

FIG. 33 represents an analysis of the anti-HER2/anti-CD20 heterodimer.

Figure 34A:
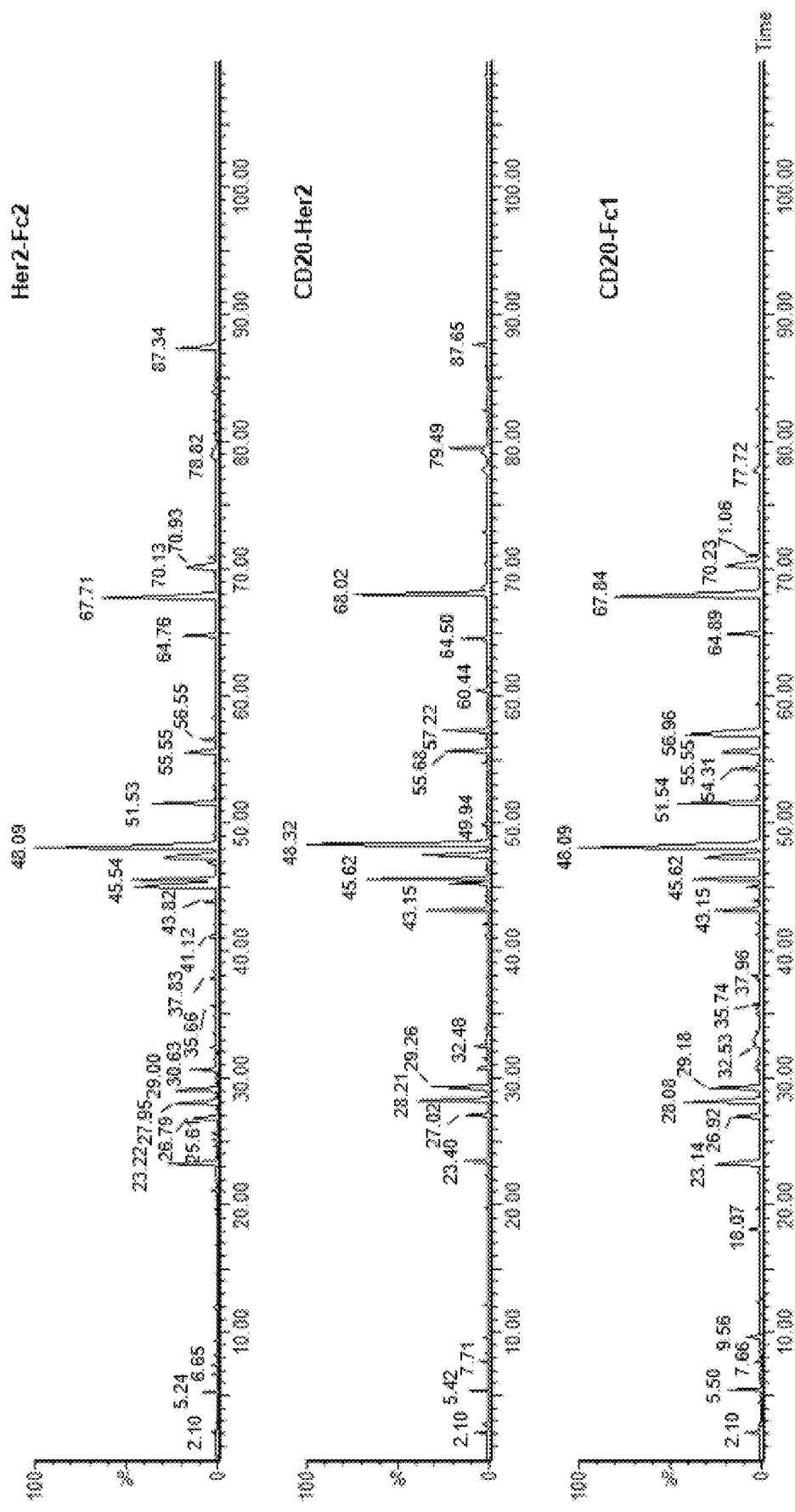
Figure 34B:
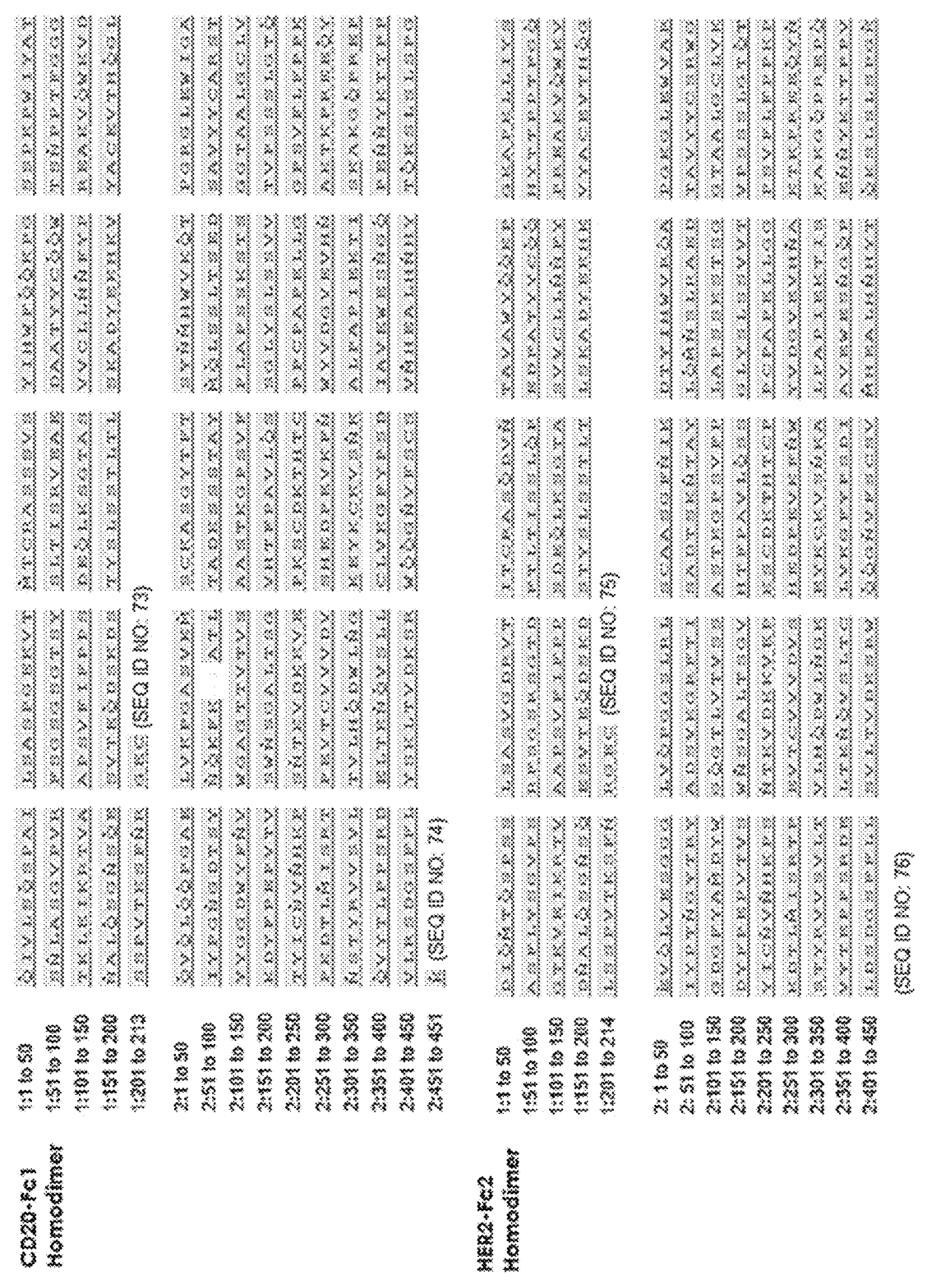
Figure 34B:
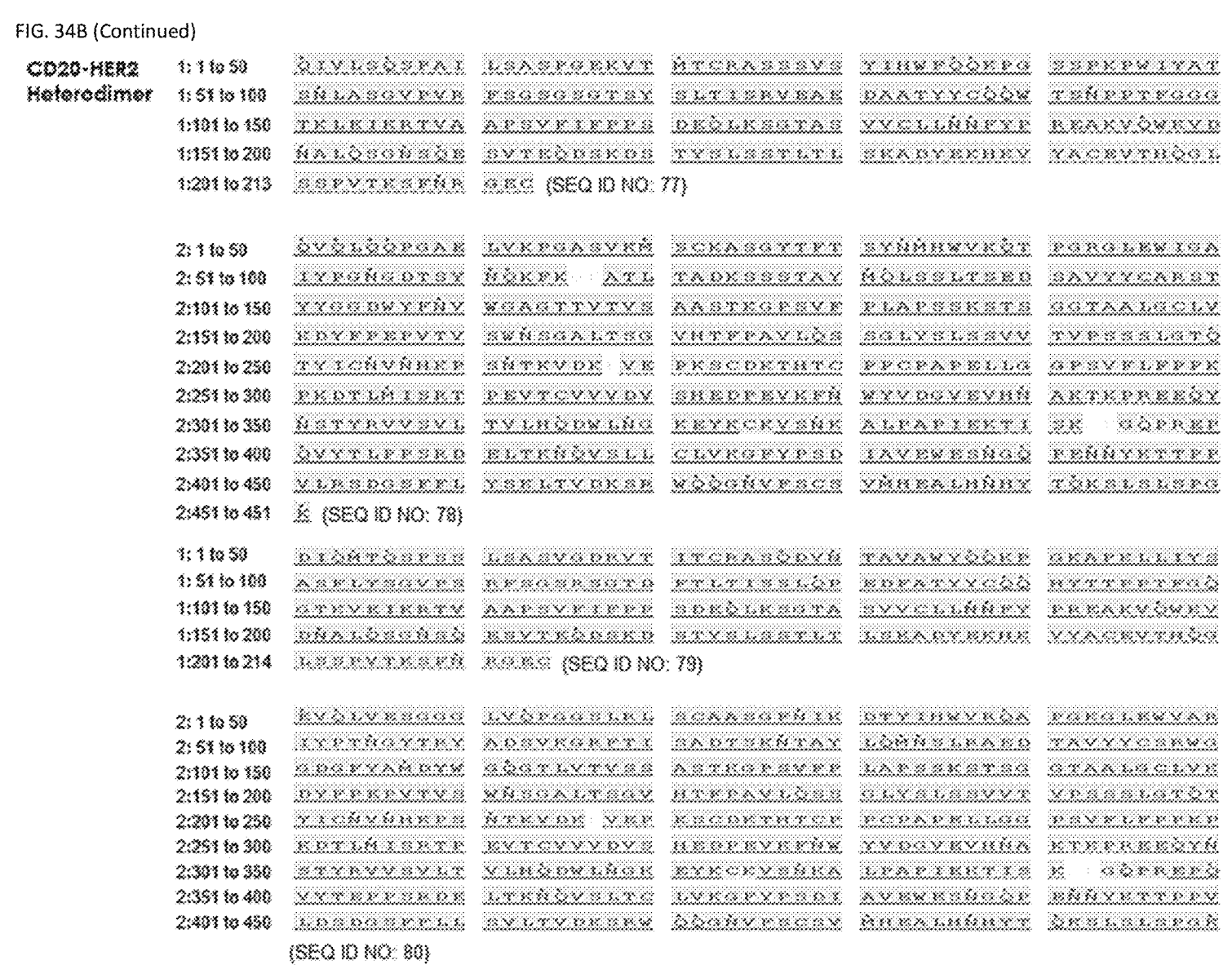

FIGS. 34A and 34B represents a mass spectrum of the anti-HER2/anti-CD20 heterodimer (FIG. 34A) and related sequence alignments (FIG. 34B). The solid line indicates the amino acids are identical to the expected ones in second MS, dotted line indicates the peptides are identical to the expected ones in primary MS, and the unshadowed amino acids indicate "not found".

VI. DETAILED DESCRIPTION OF THE INVENTION

The present disclosure relates to heterodimeric immunoglobulin-like constructs, for example (but not necessarily) bispecific antibodies, having modified heavy chain constant regions (e.g., Fc region), that lend increased stability and therapeutic efficacy to the constructs. These constructs can be made to retain the beneficial characteristics of native IgG and are free of mismatches between light chain and heavy chain. The present disclosure additionally relates to methods of producing the immunoglobulin constructs, generally through a reductive reaction and a subsequent oxidative reaction between two "half antibodies" or "halfmer" to create a heterodimer. The heterodimer of the present disclosure can be viewed as consisting of two such non-identical half antibodies or halfmers joined to each other by one or more disulfide bonds. A halfmer contains a single chain of mutated immunoglobulin heavy chain or a fragment thereof and a recognition moeity that is associated thereto (referred to as the "cognate" recognition moiety to the chain), the association being a covalent bond under typical physiological conditions. These halfmers are designed to have modifications in their heavy chain constant regions such that homodimer formation is suppressed under a reducing condition that otherwise generally favors or is supportive of homodimeric pairing by noncovalent forces, while heterodimeric association is favored between two complementarily designed halfmers in the same reducing condition. By "heterodimeric association", noncovalent forces of association are meant to be included as well as covalent ones. As used herein, "half antibody" or "halfmer" may refer to a molecule or a molecular complex that can be seen as containing only "half" of the full immuoglobulin heterotetramer or derivatives of immunoglobulin (such as scFvs) in that it has only one polypeptide chain out of the usual two that would normally constitute a Fc receptor binding member under typical physiological conditions and one recognition moiety associated with said one polypeptide chain. For example, the half antibody or halfmer may consist of an immunoglobulin heavy chain (or a fragment thereof) containing specified mutations, and an immunoglobulin light chain (or a fragment thereof) that are bound together through a covalent bond or non-covalent interactions such as hydrophobic forces and hydrogen bonding, and may be generally considered "monovalent." Or such "monovalent" half antibody or halfmer may consist of a single chain containing the hinge region and the $C_H2$ and $C_H3$ regions of an immuoglobulin heavy chain with specified mutations that is linked, for example by a covalent bond, to a non-Fab recognition moiety e.g., a single chain variable fragment (scFv) or a binding domain of a receptor. An exemplary "halfmer" or "half antibody" corresponding to the former instance is illustrated in FIG. 26 in which one immunoglobulin heavy chain and one light chain are present.

The product yield of the heterodimer of the present disclosure is similar to the native antibody and the method is simple and easy to handle. In one embodiment where the heterodimer consists of two different "half antibodies" with each half antibody consisting of a full Ig heavy chain carrying specific mutations, and a full Ig light chain, generally the half antibodies are separately expressed e.g., in two different cells, separately purified, separately reduced by reductant addition, mixed together, and then oxidized to form a heterodimer. In another embodiment where the heterodimer consists of two different halfmers in which one halfmer consists of a full heavy chain carrying specific mutations and a full light chain while the other is a FcR-binding heavy chain fragment carrying specific mutations linked to a non-Fab recognition moiety, the heterodimer of the present disclosure may be expressed and purified using a single cell line. Exemplary reductive reagents include, for example, 2-Aminoethanethiol, Dithiothreitol, TRIS™-(2-carboxyethyl)-phosphine hydrochloride, and other chemical derivatives, but such reagents are not limited as such. Exemplary oxidative reagents include, for example, L-dehydroascorbic acid and other chemical derivatives, but the reagents are not limited as such.

The heterodimers of the present disclosure can be characterized by five specific, non-cysteine mutations, in the CH3 domains on the heterodimers. These are T366, D399, L351, Y407, and K409. The numbering of the amino acid residues, as used herein, are numbered according to the Kabat EU index, for example as described in Edelman et al., 1969, Proc Natl Acad Sci USA 63:78-8, hereby incorporated by reference in its entirety. The numbering of the Kabat EU index can be used, for example, to compare a sequence of a target antibody with a consensus sequence identified by the Kabat EU index. Purely by way of example, the five mutations may comprise T366L, D399R, L351E, Y407L, and K409V. The invention, however, is strictly not limited as such. For example, the mutation at T366 may comprise any of the following, non-limiting examples: T366L, T366P, T366C, T366V, T366S, T366R, and T366W. The mutation at D399 may comprise any of the following, non-limiting examples: D399R, D399C, D399H, D399V, D399T, D399A, D399P, D399N, D399I, D399H, D399S, D399G, D399M. The mutation at L351 may comprise any of the following, non-limiting examples: L351E, L351G, L351R, L351Y, L351T, L351K, L351W, L351V, L351P, and L351D. The mutation at Y407 may comprise any of the following, non-limiting examples: 407L, Y407P, Y407A, Y407R, Y407V, Y407T, Y407H, and Y407F. The mutation at K409 may comprise any of the following, non-limiting examples: K409V, K409C, K409P, K409A, K409F, K409Q, K409R, K409T, K409S, K409M, K409Y, and K409N.

In exemplary embodiments, the mutations at T366 and D399 are on a first polypeptide, i.e., in the CH3 domain of the first heavy chain, and the mutations at L351, Y407, and K409 are on a second polypeptide, i.e., in the CH3 domain of the second heavy chain. Although the invention is explicitly not limited as such, this combination yields optimal spontaneous heterodimer formation with good stability and binding activity. Each halfmer has a strong attraction toward its complementary halfmer "partner" or chain, and a strong repulsion against self, thus strongly favoring heterodimer formation and strongly disfavoring homodimer formation. When only one out of the two constituent halfmers is present in an aqueous solution under physiological conditions that are sufficiently reducing, the actual polypeptidyl forms present may include the halfmer form, the homodimeric form in which two halfmers are held by non-covalent forces, and unfolded forms. In such solution, the portion of the polypeptidyl forms in the form of the homodimer is significantly suppressed, provided that the aqueous solution is essentially free of any polypeptide other than the above-mentioned halfmer, such as the complementary "other" halfmer. Put differently, when only one of the first or second polypeptide chain and are cognition moeity associated thereto (the "cognate" recognition moiety to the polypeptide chain) is introduced in an aqueous medium under physiological conditions containing sufficient amount of reductant, such polypeptide chain and its cognate recognition moiety do not tend to form homodimers, but prefers to remain as a halfmer in the aqueous solution, provided that said solution is essentially free of any other polypeptide. Such act of introduction into an aqueous solution includes, for example, expression in a host cell. Likewise, when both of the two such polypeptide chains with their cognate recognition moieties are introduced in an aqueous solution under physiological conditions containing sufficient amount of reductant, the corresponding heterodimer as well as its constituent halfmers may be present, but formation of homodimers is suppressed. The proportion of homodimer formation in the presence of the reducing agent is typically less than 50% by weight based on the total weight of all the polypeptidyl forms (halfmers, homodimers, heterodimers, unfolded species, etc.) present in the aqueous solution when the aqueous solution is essentially free of other polypeptides. For example, the ratio (by weight) of the homodimers formed by the first polypeptide, the second polypeptide, the first polypeptide being covalently joined to the recognition moiety, or the second polypeptide being covalently joined to the recognition moiety are less than 50% in the presence of a reductant. For example, less than 45%, 40%, 35%, 30%, 25%, 20%, 15%, 10%, 5%, 4%, 3%, 2%, 1% or even less.

In certain embodiments, the reductant is selected from the group consisting of glutathione, 2-mercaptoethanol, 2-mercaptoethylamine, TRIS™ (2-carboxyethyl)phosphine (TCEP), cysteine, cysteine hydrochloride, dithiothreitol (DTT), cysteindithiothreitol, dithiolbutylamine, dithioerythritol (DTE), sodium borohydride ($NaBH_4$), sodium cyanoborohydride ($NaCNBH_3$), and/or combinations thereof. In some embodiments, the reductant concentration can be between 1 and 100 fold (e.g., 20 to 50 fold) molar excess relative to the protein concentration. In certain embodiments, the reductant can be at a concentration of about 0.1 mM to about 20 mM. Representative reductants that can be used in sufficient amount include 1 mM dithiothreitol or higher, 50 mM 2-mercaptoethylamine or higher and 50 mM cysteine or higher. In some embodiments, the reductant is removed following incubation with the protein prior to oxidation of the protein.

The first polypeptides and the second polypeptides may separately connect to a recognition moiety by a covalent bond or a flexible linker, wherein the recognition moiety includes but is not limited to an antigen-binding fragment, a single chain antibody fragment (scFv), a receptor-recognizing ligand, or a ligand-recognizing receptor. The covalent bond comprises a chemical link between two or more atoms where the outer electron shell is shared among them. The stable chemical structure forming when these electrons reach at a saturated state, is known as covalent bond. Put differently, the covalent bond comprises the interaction by sharing electron pairs between atoms which are from either a same element or a different element. The covalent bond between the first polypeptides and the second polypeptides in the present disclosure include, but are not limited to, an amido-bond, which is synthesized when the amino group of one amino acid reacts with the carboxyl group of the other amino acid, causing the release of a molecule of water ($H_2O$), or an amido-bond or amide-bond synthesized by ethylene glycol, polyethylene glycol, or aldehyde group of other compounds and their polymers interacting with amino group of one amino acid molecule. The flexible linker may comprise a short amino acid sequence or a polymer. Such amino acid sequence includes but is not limited to GGGGSGGGGSGGGGS (SEQ ID NO: 72).

Other combinations of mutations at T366, D399, L351, Y407, and K409 are explicitly within the scope of the present invention. For example, any of the following combinations of a)-h) from Group I and Group II:

Group I:
a) T366L in the first polypeptide and L351E, Y407L in the second polypeptide;
b) T366L in the first polypeptide and L351G, Y407L in the second polypeptide;
c) T366L in the first polypeptide and L351Y, Y407A in the second polypeptide;
d) T366P in the first polypeptide and L351V, Y407P in the second polypeptide;
e) T366W in the first polypeptide and L351D, Y407P in the second polypeptide;
f) T366P in the first polypeptide and L351P, Y407F in the second polypeptide;
g) T366V in the first polypeptide and L351K, Y407T in the second polypeptide; and
h) T366L in the first polypeptide and L351W, Y407H in the second polypeptide.

Group II:
a) D399R in the first polypeptide and K409V in the second polypeptide;
b) D399C in the first polypeptide and K409C in the second polypeptide;
c) D399C in the first polypeptide and K409P in the second polypeptide;
d) D399N in the first polypeptide and K409S in the second polypeptide;
e) D399G in the first polypeptide and K409S in the second polypeptide;
f) D399I in the first polypeptide and K409F in the second polypeptide;
g) D399T in the first polypeptide and K409Q in the second polypeptide; and h) D399 Å in the first polypeptide and K409R in the second polypeptide.

Any of the following combinations of a)-h) from Group III and Group IV:

Group III:
  a) T366L in the first polypeptide and L351E, Y407L in the second polypeptide;
  b) T366L in the first polypeptide and L351G, Y407L in the second polypeptide;
  c) T366L in the first polypeptide and L351Y, Y407A in the second polypeptide;
  d) T366P in the first polypeptide and L351V, Y407P in the second polypeptide;
  e) T66W in the first polypeptide and L351D, Y407P in the second polypeptide;
  f) T366P in the first polypeptide and L351P, Y407F in the second polypeptide;
  g) T366V in the first polypeptide and L351K, Y407T in the second polypeptide; and
  h) T366L in the first polypeptide and L351W, Y407H in the second polypeptide.

Group IV:
  a) K409V in the first polypeptide and D399R in the second polypeptide;
  b) K409C in the first polypeptide and D399C in the second polypeptide;
  c) K409P in the first polypeptide and D399C in the second polypeptide;
  d) K409S in the first polypeptide and D399N in the second polypeptide;
  e) K409S in the first polypeptide and D399G in the second polypeptide;
  f) K409F in the first polypeptide and D399I in the second polypeptide;
  g) K409Q in the first polypeptide and D399T in the second polypeptide; and
  h) K409R in the first polypeptide and D399 Å in the second polypeptide.

Any of the following members a)-h) from Group V:
Group V:
  a) T366L and D399R in the first polypeptide and L351E, Y407L and K409V in the second polypeptide;
  b) T366L and D399C in the first polypeptide and L351G, Y407L and K409C in the second polypeptide;
  c) T366L and D399C in the first polypeptide and L351Y, Y407A and K409P in the second polypeptide;
  d) T366P and D399N in the first polypeptide and L351V, Y407P and K409S in the second polypeptide;
  e) T366W and D399G in the first polypeptide and L351D, Y407P and K409S in the second polypeptide;
  f) T366P and D399I in the first polypeptide and L351P, Y407F and K409F in the second polypeptide;
  g) T366V and D399T in the first polypeptide and L351K, Y407T and K409Q in the second polypeptide; and
  h) T366L and D399 Å in the first polypeptide and L351W, Y407H and K409R in the second polypeptide.

Any of the following members a)-h) from Group VI:
Group VI:
  a) T366L and K409V in the first polypeptide and L351E, Y407L and D399R in the second polypeptide;
  b) T366L and K409C in the first polypeptide and L351G, Y407L and D399C in the second polypeptide;
  c) T366L and K409P in the first polypeptide and L351Y, Y407A and D399C in the second polypeptide;
  d) T366P and K409S in the first polypeptide and L351V, Y407P and D399N in the second polypeptide;
  e) T366W and K409S in the first polypeptide and L351D, Y407P and D399G in the second polypeptide;
  f) T366P and K409F in the first polypeptide and L351P, Y407F and D399I in the second polypeptide;
  g) T366V and K409Q in the first polypeptide and L351K, Y407T and D399T in the second polypeptide; and
  h) T366L and K409R in the first polypeptide and L351W, Y407H and D399 Å in the second polypeptide.

The first polypeptide and the second polypeptide may each comprise a heavy chain. The heterodimer constructs of the present invention may comprise bispecific antibodies, but are explicitly not limited as such. For example, the heterodimer constructs may comprise one or more scFv fragments, one or more Fab fragments, e.g., an scFv fragment and a Fab fragment, or two Fab fragments. Exemplary sequences of the polypeptides of the heterodimers include, but are specifically not limited to, any one of SEQ ID NOs: 16-31, 33, 35, 37, 39, 41, 43, 45, 48, 49, 51, 53, 55, 57, 59, 61, 63, 68, 69, 70 and 71. Also included are variant sequences that share at least 70% sequence identity (while maintaining biological activity) of any one of SEQ ID NOs: 16-31, 33, 35, 37, 39, 41, 43, 45, 48, 49, 51, 53, 55, 57, 59, 61, 63, 68, 69, 70 and 71. For example, at least 75%, 80%, 85%, 90%, 95%, 96%, 97%, 98%, 99%, 99.1%, 99.2%, 99.3%, 99.4%, 99.5%, 99.6%, 99.7%, 99.8%, 99.9% or even better sequence identity. Additionally, any one of SEQ ID NOs: 16-31, 33, 35, 37, 39, 41, 43, 45, 48, 49, 51, 53, 55, 57, 59, 61, 63, 68, 69, 70 and 71 may have one or more conservative substitution and still be within the scope of the present disclosure.

The bispecific heterodimeric antibodies of the present disclosure form one or more disulfide bonds between the first and second heavy chains. The disfulde bonds can form either during expression in the same cell, or may be formed through an oxidation reaction by addition of an oxidizing agent in vitro. Such disulfide bond formation occurs in those embodiments where the halfmers are expressed, purified, reduced by reductant addition, mixed together, and then oxidized to form a heterodimer.

The heterodimers of the present invention are capable of binding to Fc receptors, e.g., one or more of one of FcγRI, FcγRIIA, FcγRIIB1, FcγRIIB2, FcγRIIIA, FcγRIIIB, FcεRI, FcεRII, FcαRI, Fcα/μR, and FcRn. In exemplary embodiments, the heterodimers retain the ability to bind to FcRn. As used herein, FcRn refers to the structurally homologous to the WIC class I heterodimeric receptor family, comprising a class I transmembrane heavy chain (p51 subunit, alpha chain) and a soluble light chain (p14 subunit, beta chain), which combine together by non-covalent interaction. The binding sites of FcRn on an IgG are located at the interface of CH2-CH3. The most important amino acid sites are 253, 310 and 435.

By nature of their structure, the heterodimers of the present invention may (but not necessarily) target one or more antigens simultaneously. In exemplary embodiments, the antigens comprise one or more of HER2, PD-L1, TROP2, CD3, and/or CD20. However, the invention is strictly not limited as such. This is because the present disclosure relates to modifications of the constant region (CH3) of the antibodies/immunoglobulin constructs for improved stability, serum half-life, and therapeutic efficacy. Thus the technology underlying the present disclosure may be applied to monoclonal antibodies which bind to just one target antigen. This includes, for example, known therapeutic antibodies. Such antibodies may still benefit from the improved stability that comes from having the modified constant regions. In such cases, the recognition moieties on (or connected to) the first polypeptide and the second polypeptides would remain the same, and the differences between the "half antibodies" or "halfmers" may lie exclusively in the CH3 region.

Known therapeutic monoclonal antibodies which may benefit from the modifications disclosed in present disclosure may include any of the following, non-limiting antibodies: 3F8, 8H9, Abagovomab, Abciximab, Abituzumab, Abrilumab, Actoxumab, Adalimumab, Adecatumumab, Aducanumab, Afasevikumab, Afelimomab, Afutuzumab, Alacizumab pegol, ALD518, Alemtuzumab, Alirocumab, Altumomab pentetate, Amatuximab, Anatumomab mafenatox, Anetumab ravtansine, Anifrolumab, Anrukinzumab, Apolizumab, Arcitumomab, Ascrinvacumab, Aselizumab, Atezolizumab, Atinumab, Atlizumab, Atorolimumab, Avelumab Bapineuzumab, Basiliximab, Bavituximab, Bectumomab, Begelomab, Belimumab, Benralizumab, Bertilimumab, Besilesomab, Bevacizumab, Bezlotoxumab, Biciromab, Bimagrumab, Bimekizumab, Bivatuzumab mertansine, Bleselumab, Blinatumomab, Blontuvetmab, Blosozumab, Bococizumab, Brazikumab, Brentuximab vedotin, Briakinumab, Brodalumab, Brolucizumab, Brontictuzumab, Burosumab, Cabiralizumab, Canakinumab, Cantuzumab mertansine, Cantuzumab ravtansine, Caplacizumab, Capromab pendetide, Carlumab, Carotuximab, Catumaxomab, cBR96-doxorubicin immunoconjugate, Cedelizumab, Cergutuzumab amunaleukin, Certolizumab pegol, Cetuximab, Citatuzumab bogatox, Cixutumumab, Clazakizumab, Clenoliximab, Clivatuzumab tetraxetan, Codrituzumab, Coltuximab ravtansine, Conatumumab, Concizumab, CR6261, Crenezumab, Crotedumab, Dacetuzumab, Daclizumab, Dalotuzumab, Dapirolizumab pegol, Daratumumab, Dectrekumab, Demcizumab, Denintuzumab mafodotin, Denosumab, Depatuxizumab mafodotin, Derlotuximab biotin, Detumomab, Dinutuximab, Diridavumab, Domagrozumab, Dorlimomab aritox, Drozitumab, Duligotumab, Dupilumab, Durvalumab, Dusigitumab, Ecromeximab, Eculizumab, Edobacomab, Edrecolomab, Efalizumab, Efungumab, Eldelumab, Elgemtumab, Elotuzumab, Elsilimomab, Emactuzumab, Emibetuzumab, Emicizumab, Enavatuzumab, Enfortumab vedotin, Enlimomab pegol, Enoblituzumab, Enokizumab, Enoticumab, Ensituximab, Epitumomab cituxetan, Epratuzumab, Erenumab, Erlizumab, Ertumaxomab, Etaracizumab, Etrolizumab, Evinacumab, Evolocumab, Exbivirumab, Fanolesomab, Faralimomab, Farletuzumab, Fasinumab, FBTA05, Felvizumab, Fezakinumab, Fibatuzumab, Ficlatuzumab, Figitumumab, Firivumab, Flanvotumab, Fletikumab, Fontolizumab, Foralumab, Foravirumab, Fresolimumab, Fulranumab, Futuximab, Galcanezumab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Idarucizumab, Igovomab, IMAB362, Imalumab, Imciromab, Imgatuzumab, Inclacumab, Indatuximab ravtansine, Indusatumab vedotin, Inebilizumab, Infliximab, Inolimomab, Inotuzumab ozogamicin, Intetumumab, Ipilimumab, Iratumumab, Isatuximab, Itolizumab, Ixekizumab, Keliximab, Labetuzumab, Lampalizumab, Lanadelumab, Landogrozumab, Laprituximab emtansine, Lebrikizumab, Lemalesomab, Lendalizumab, Lenzilumab, Lerdelimumab, Lexatumumab, Libivirumab, Lifastuzumab vedotin, Ligelizumab, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, MABp1, Mapatumumab, Margetuximab, Maslimomab, Matuzumab, Mavrilimumab, Mepolizumab, Metelimumab, Milatuzumab, Minretumomab, Mirvetuximab soravtansine, Mitumomab, Mogamulizumab, Monalizumab, Morolimumab, Motavizumab, Moxetumomab pasudotox, Muromonab-CD3, Nacolomab tafenatox, Namilumab, Naptumomab estafenatox, Naratuximab emtansine, Narnatumab, Natalizumab, Navicixizumab, Navivumab, Nebacumab, Necitumumab, Nemolizumab, Nerelimomab, Nesvacumab, Nimotuzumab, Nivolumab, Nofetumomab merpentan, Obiltoxaximab, Obinutuzumab, Ocaratuzumab, Ocrelizumab, Odulimomab, Ofatumumab, Olaratumab, Olokizumab, Omalizumab, Onartuzumab, Ontuxizumab, Opicinumab, Oportuzumab monatox, Oregovomab, Orticumab, Otelixizumab, Otlertuzumab, Oxelumab, Ozanezumab, Ozoralizumab, Pagibaximab, Palivizumab, Pamrevlumab, Panitumumab, Pankomab, Panobacumab, Parsatuzumab, Pascolizumab, Pasotuxizumab, Pateclizumab, Patritumab, Pembrolizumab, Pemtumomab, Perakizumab, Pertuzumab, Pexelizumab, Pidilizumab, Pinatuzumab vedotin, Pintumomab, Placulumab, Plozalizumab, Pogalizumab, Polatuzumab vedotin, Ponezumab, Prezalizumab, Priliximab, Pritoxaximab, Pritumumab, PRO 140, Quilizumab, Racotumomab, Radretumab, Rafivirumab, Ralpancizumab, Ramucirumab, Ranibizumab, Raxibacumab, Refanezumab, Regavirumab, Reslizumab, Rilotumumab, Rinucumab, Risankizumab, Rituximab, Rivabazumab pegol, Robatumumab, Roledumab, Romosozumab, Rontalizumab, Rovalpituzumab tesirine, Rovelizumab, Ruplizumab, Sacituzumab govitecan, Samalizumab, Sapelizumab, Sarilumab, Satumomab pendetide, Secukinumab, Seribantumab, Setoxaximab, Sevirumab, SGN-CD19A, SGN-CD33A, Sibrotuzumab, Sifalimumab, Siltuximab, Simtuzumab, Siplizumab, Sirukumab, Sofituzumab vedotin, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tamtuvetmab, Tanezumab, Taplitumomab paptox, Tarextumab, Tefibazumab, Telimomab aritox, Tenatumomab, Teneliximab, Teplizumab, Teprotumumab, Tesidolumab, Tetulomab, Tezepelumab, TGN1412, Ticilimumab, Tigatuzumab, Tildrakizumab, Timolumab, Tisotumab vedotin, TNX-650, Tocilizumab, Toralizumab, Tosatoxumab, Tositumomab, Tovetumab, Tralokinumab, Trastuzumab, Trastuzumab emtansine, TRBS07, Tregalizumab, Tremelimumab, Trevogrumab, Tucotuzumab celmoleukin, Tuvirumab, Ublituximab, Ulocuplumab, Urelumab, Urtoxazumab, Ustekinumab, Utomilumab, Vadastuximab talirine, Vandortuzumab vedotin, Vantictumab, Vanucizumab, Vapaliximab, Varlilumab, Vatelizumab, Vedolizumab, Veltuzumab, Vepalimomab, Vesencumab, Visilizumab, Vobarilizumab, Volociximab, Vorsetuzumab mafodotin, Votumumab, Xentuzumab, Zalutumumab, Zanolimumab, Zatuximab, Ziralimumab, Zolimomab aritox, and combinations thereof.

The targets may comprise any of the following, non-limiting targets: β-amyloid, 4-1BB, SAC, 5T4, α-fetoprotein, angiopoietin, AOC3, B7-H3, BAFF, c-MET, c-MYC, C242 antigen, C5, CA-125, CCL11, CCR2, CCR4, CCR5, CD4, CD8, CD11, CD18, CD125, CD140a, CD127, CD15, CD152, CD140, CD19, CD2, CD20, CD22, CD23, CD25, CD27, CD274, CD276, CD28, CD3, CD30, CD33, CD37, CD38, CD4, CD40, CD41, CD44, CD47, CD5, CD51, CD52, CD56, CD6, CD74, CD80, CEA, CFD, CGRP, CLDN, CSF1R, CSF2, CTGF, CTLA-4, CXCR4, CXCR7, DKK1, DLL3, DLL4, DR5, EGFL7, EGFR, EPCAM, ERBB2, ERBB3, FAP, FGF23, FGFR1, GD2, GD3, GDF-8, GPNMB, GUCY2C, HER1, HER2, HGF, HIV-1, HSP90, ICAM-1, IFN-α, IFN-γ, IgE, CD221, IGF1, IGF2, IGHE, IL-1, IL2, IL-4, IL-5, IL-6, IL-6R, IL-9, IL-12 IL-15, IL-15R, IL-17, IL-13, IL-18, IL-1β, IL-22, IL-23, IL23A, integrins, ITGA2, IGTB2, Lewis-Y antigen, LFA-1, LOXL2, LTA, MCP-1, MIF, MS5A1, MUC1, MUC16, MSLN, myostatin, MMP superfamily, NCA-90, NFG, NOGO-A, Notch 1, NRP1, OX-40, OX-40L, P2X superfamily, PCSK9, PD-1, PD-L1, PDCD1, PDGF-R, RANKL, RHD, RON, TRN4, serum albumin, SDC1, SLAMF7, SIRPα, SOST, SHP1, SHP2, STEAP1, TAG-72, TEM1, TIGIT, TFPI, TGF-β, TNF-α, TNF superfamily, TRAIL superfamily, Toll-like receptors, WNT superfamily, VEGF-A, VEGFR-1, VWF, cytomegalovirus (CMV), respiratory syncytial virus (RSV), hepatitis B, hepatitis C, influenza A hemagglutinin, rabies virus, HIV virus, herpes simplex virus, and combinations thereof.

The heterodimer constructs of the present disclosure may have one or more substitutions, deletions, additions and/or insertions, beyond the specific five amino acid substitutions in the CH3 domain disclosed herein. For example, certain amino acids may be substitute for other amino acids in the protein structure without significant loss of ability to bind to other polypeptides such as antigens or cells. Since the binding capacity and protein properties determine the biological activity of the protein, certain amino acid sequence substitutions can be made in the protein sequence without significant loss of their biological utility or activity. In many cases, polypeptide variants contain one or more conservative substitutions.

The heterodimer constructs of the present disclosure may be provided in the form of a pharmaceutical composition comprising a pharmaceutically acceptable carrier, excipient, or solvent. The composition may optionally contain one or more additional pharmaceutically active ingredients, such as another antibody or a therapeutic agent. The pharmaceutical compositions of the invention also can be administered in a combination therapy with, for example, another immune-stimulatory agent, anti-cancer agent, an antiviral agent, or a vaccine, etc. In certain embodiments, a composition comprises a heterodimer at a concentration of at least 1 mg/mL, 5 mg/mL, 10 mg/mL, 50 mg/mL, 100 mg/mL, 150 mg/mL, or 200 mg/mL. In some embodiments, the heterodimer can be at a concentration of 1-300 mg/mL, or 100-300 mg/mL.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: The Science and Practice of Pharmacy, 20$^{th}$ Ed. (Lippincott Williams & Wilkins 2003), the disclosure of which is incorporated herein by reference.

Preferably, a pharmaceutical composition is suitable for intravenous, intramuscular, subcutaneous, parenteral, spinal or epidermal administration (e.g., by injection or infusion). Depending on the route of administration, the active compound can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the present invention described herein can be administered via a non-parenteral route, such as a topical, epidermal or mucosal route of administration, e.g., intranasally, orally, vaginally, rectally, sublingually or topically.

The pharmaceutical composition of the invention can be in the form of pharmaceutically acceptable salts. A "pharmaceutically acceptable salt" refers to a salt that retains the desired biological activity of the parent compound and does not impart any undesired toxicological effects. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The pharmaceutically acceptable composition may be in liquid form or solid form. A solid formulation is generally, but not necessarily, lyophilized and brought into solution prior to administration for either single or multiple dosing. The formulations should not be exposed to extreme temperature or pH so as to avoid thermal denaturation. Thus, an antibody composition of the present disclosure should be formulated within a biologically relevant pH range. A solution buffered to maintain a proper pH range during storage is often necessary, especially for liquid formulations stored for longer periods of time between formulation and administration. Typically, both liquid and solid formulations require storage at lower temperatures (usually 2-8° C.) in order to retain stability for longer periods. Formulated antibody compositions, especially liquid formulations, may contain a bacteriostat to prevent or minimize proteolysis during storage, including but not limited to effective concentrations (usually <1% w/v) of benzyl alcohol, phenol, m-cresol, chlorobutanol, methylparaben, and/or propylparaben. A bacteriostat may be contraindicated for some patients. Therefore, a lyophilized formulation may be reconstituted in a solution either containing or not containing such a component. Additional components may be added to either a buffered liquid or solid antibody formulation, including but not limited to sugars as a cryoprotectant (including but not necessarily limited to polyhydroxy hydrocarbons such as sorbitol, mannitol, glycerol and dulcitol and/or disaccharides such as sucrose, lactose, maltose or trehalose) and, in some instances, a relevant salt (including but not limited to NaCl, KCl or LiCl). Such antibody formulations, especially liquid formulations slated for long term storage, will rely on a useful range of total osmolarity to both promote long term stability at temperature of 2-8° C., or higher, while also making the formulation useful for parenteral injection. For example, but not necessarily, an effective range of total osmolarity (the total number of molecules in solution) may be from about 200 mOs/L to about 800 mOs/L. It will be apparent that the amount of a cyroprotectant, such as sucrose or sorbitol, will depend upon the amount of salt in the formulation in order for the total osmolarity of the solution to remain within an appropriate range. Therefore a salt free formulation may, but not necessarily, contain from about 5% to about 25% sucrose.

Alternatively, a salt free sorbitol-based formulation may, but not necessarily, contain sorbitol within a range from about 3% to about 12%. Salt-free formulations will of course warrant increased ranges of the respective cryoprotectant in order to maintain effective osmolarity levels. These formulation may also contain a divalent cation (including but not necessarily limited to $MgCl_2$, $CaCl_2$) and $MnCl_2$); and a non-32 ionic surfactant (including but not necessarily limited to Polysorbate-80 (TWEEN 80®), Polysorbate-60 (TWEEN 60®), Polysorbate-40 (TWEEN 40®) and Polysorbate-20 (TWEEN 20®), polyoxyethylene alkyl ethers, including but not limited to BRIJ 58®, BRIJ 35®, as well as others such as Triton X-100®, TRITON X 114®, NP40®, SPAN™ 85 and the PLURONIC™ series of nonionic surfactants (e.g., PLURONIC™ 121)). Any combination of such components, including probable inclusion of a bacteriostat, may be useful to fill the antibody-containing formulations of the present disclosure. A heterodimer of the present disclosure may also be a "chemical derivative", which describes an antibody that contains additional chemical moieties which are not normally a part of the immunoglobulin molecule (e.g., pegylation). Such moieties may improve the solubility, half-life, absorption, etc. of the base molecule. Alternatively the moieties may attenuate undesirable side effects of the base molecule or decrease the toxicity of the base molecule. The pharmaceutical composition of the present invention can be in the form of sterile aqueous solutions or dispersions. It can also be formulated in a microemulsion, liposome, or other ordered structure suitable to high drug concentration.

The heterodimeric constructs of the present disclosure are capable of binding multiple target molecules simultaneously and are thus more effective in the treatment of complex diseases. The heterodimer constructs of the present disclosure may be administered to a subject in need thereof to treat a disease or disorder, for example, a viral or bacterial infection, a metabolic or autoimmune disorder, or cancer or other cellular proliferative disorder. In some embodiments, the autoimmune diseases comprise at least one of arthritis, rheumatoid arthritis, psoriasis, multiple sclerosis (MS), ulcerative colitis, Crohn's disease, systemic lupus erythematosus (SLE), glomerulonephritis, dilated cardiomyopathy-like diseases, Sjogren's syndrome, allergic contact dermatitis, polymyositis, scleroderma, periarteritis nodosa, rheumatic fever, vitiligo, insulin-dependent diabetes mellitus, Behcet's syndrome, chronic thyroiditis, and combinations thereof. In some embodiments, the neurodegenerative diseases comprise at least one of Parkinson's disease, Huntington's disease, Machado-Joseph disease, amyotrophic lateral sclerosis (ALS), Creutzfeldt-Jakob disease, and combinations thereof. In some embodiments, theneoplastic diseases and cellular proliferative disorders comprise at least one of leukemia, lymphoma, myeloma, brain tumors, head and neck squamous cell carcinoma, non-small cell lung cancer (NSCLC), nasopharyngeal cancer, esophageal cancer, stomach cancer, pancreatic cancer, gallbladder cancer, liver cancer, colorectal cancer, breast cancer, ovarian cancer, cervical cancer, endometrial cancer, uterine sarcoma, prostate cancer, bladder cancer, renal cell carcinoma, melanoma, and combinations thereof.

The present disclosure is additionally directed to one or more nucleic acids encoding one or more polypeptides of the heterodimeric constructs of the present disclosure. The nucleic acids may encode any one of SEQ ID NOs: 16-31, 33, 35, 37, 39, 41, 43, 45, 48, 49, 51, 53, 55, 57, 59, 61, 63, 68, 69, 70 and 71. In some embodiments, the nucleic acids may comprise any one of SEQ ID NOs: 32, 34, 36, 38, 40, 42, 44, 46, 47, 50, 52, 54, 56, 58, 60, 62, and 64-67. Also included are variant sequences that share at least 70% sequence identity with any one of SEQ ID NOs: 32, 34, 36, 38, 40, 42, 44, 46, 47, 50, 52, 54, 56, 58, 60, 62, and 64-67. For example, at least 75%, 80%, 85%, 90%, 95%, 96%, 97%, 98%, 99%, 99.1%, 99.2%, 99.3%, 99.4%, 99.5%, 99.6%, 99.7%, 99.8%, 99.9% or even better sequence identity. The variant nucleic acid sequences may be codon optimized. As used herein, codon optimization refers to an in vitro mutagenesis of a nucleic acid to increase or maximize expression of a gene (e.g., a transgene relative to the unmodified nucleic acid, without changing (or with minimal change) to the amino acid sequence of the synthesized protein, i.e., synonymous mutations. Codon optimization can affect protein expression rates up to 1,000× fold, particularly by favoring efficient soluble protein expression. The codons changed are typically ones not generally used by the host cell translation system.

Within scope of this invention are nucleic acid sequences capable of hybridizing to a nucleic acid or a fragment (or a complementary sequence) of the present disclosure under moderate to high stringency conditions. Hybridization techniques are well known in the field of molecular biology. For example, suitable conditions for testing include prewashing in a solution of 5×SSC, 0.5% SDS, 1.0 mM EDTA (pH 8.0); hybridize overnight at 50-60° C., 5×SSC; followed by washing twice for 20 minutes with 2×, 0.5× and 0.2×SSC containing 0.1% SDS solution respectively. Alternatively, a suitable high stringency hybridization condition includes the conditions described above, except that the hybridization temperature is increased, for example, to 60-65° C. or 65-70° C.

The nucleic acids of the present disclosure may be contained in a vector or vector system. The vector may be, for example but not necessarily, a plasmid. Other explicitly non-limiting recombinant vectors may include shuttle vectors and expression vectors. In general, a plasmid construct includes an origin of replication (e.g., ColE1 origin) and selection markers (e.g., ampicillin or tetracycline resistance). Expression vectors comprise those vectors comprising a control sequence or regulatory element required for expression of, e.g., a heterodimeric construct according to the present disclosure. Other explicitly non-limiting recombinant vectors are known in the art and may include, e.g., phage vectors such as a λ phage vector, other viral vectors such as non-replicating adenoviral vector, lentiviral vector, pSV, pCMV series of plasmid vectors, vaccinia and retroviral vectors, baculoviral vectors, cosmids, artificial chromosomes. The vector may be a mammalian expression vector. For example, vectors may be transfected into mammalian cells and the DNA may be integrated into the genome by homologous recombination in the case of stable transfection, or alternatively the cells may be transiently transfected. Common to most engineered vectors are origins of replication, multicloning sites, and selectable markers, so as long as a vector (including systems of vectors, e.g., multiple plasmids) contain such a system they are considered to be covered by the scope of this invention. Common promoters for mammalian expression vectors include CMV and SV40 promoters. Nonviral promoters such as EF-1 promoters are also known. Exemplary vectors include plasmid vectors pX0GC modified from pCDNA vectors.

The present disclosure also embodies host cells containing a vector or vector system according to any aspect of the present disclosure. One of ordinary skill in the art will appreciate that different cell types may lead to different heterodimeric construct products and may possibly impact the therapeutic efficacy of the products. For example, the host cells may (but not necessarily) comprise any of the following cell types: human embryonic kidney cells (HEK293) or HEK293T, HEK293E, HEK293F modified from HEK293, Chinese hamster ovary cells (CHO) or CHO—S, CHO-dhfr⁻, CHO/DG44, ExpiCHO modified from CHO cells, and related cell lines. Other cell lines known in the art include NS0 murine myeloma cells, PER.C6 human cells, yeast cells, e.g., *S. cerevisiae, S. pombe* and *P. pastoris*, and bacterial cells, e.g., *E. coli*. Cell-free expression systems also exist, for example, based on *E. coli* cell lysates, containing cellular components necessary for transcription/translation. Eukaryotic and mammalian cell-free systems are also known in the art, for example wheat germ cell-free expression system, and those described in Brodel et al (2015), *Methods Mol Bio.* 1261: 129-40, hereby incorporated by reference in its entirety. Some recombinant antibody production systems express the recombinant antibodies on the surface of the host cell before harvesting, and others simply release the antibodies into a medium for collection. Such variations are intended to be within the scope of the present disclosure.

As used herein, the term "antibody" (Ab) is used in the broadest sense and specifically may include any immunoglobulin, whether natural or partly or wholly synthetically produced, including but not limited to monoclonal antibodies, polyclonal antibodies, multispecific antibodies (for example, bispecific antibodies and polyreactive antibodies), and antibody fragments. Thus, the term "antibody" as used in any context within this specification is meant to include, but not be limited to, any specific binding member, immunoglobulin class and/or isotype (e.g., IgG1, IgG2a, IgG2b, IgG3, IgG4, IgM, IgA1, IgA2, IgD, and IgE) and biologically relevant fragment or specific binding member thereof, including but not limited to Fab, F(ab')2, scFv (single chain or related entity) and (scFv)$_2$.

As used herein, the term "antibody fragments" may include those antibody fragments obtained using techniques readily known and available to those of ordinary skill in the art, as reviewed herein. Therefore, in addition to the definition for "antibody" presented supra, the term "antibody" may further encompass any polypeptide or protein comprising a portion of an intact antibody, such as the antigen binding or variable region of the intact antibody. These can be derived from natural sources, or they may be partly or wholly synthetically produced. Examples of antibody fragments include, but are not limited to, Fab, Fab', F(ab')2, and Fv fragments; diabodies, and linear antibodies.

As used herein, the term "antibody-dependent cell-mediated cytotoxicity" or "ADCC" may refer to a cell-mediated reaction in which cytotoxic cells (e.g., nonspecific) that express FcRs (e.g., Natural Killer (NK) cells, neutrophils, and macrophages) recognize bound antibody on a target cell and subsequently cause lysis of the target cells. The primary cells for mediating ADCC, NK cells, express FcγRIII, whereas monocytes express FcγRI, FcγRII and FcγRIII As used herein, the term "bispecific antibody" refers to an antibody having the capacity to bind to two distinct epitopes either on a single antigen or two different antigens. Epitopes can be formed both from contiguous amino acids (linear epitope) or noncontiguous amino acids juxtaposed by tertiary folding of a protein (conformational epitopes). Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. A bispecific antibody of the present disclosure may be bivalent, trivalent, or tetravalent. As used herein, "valent", "valence", "valencies", or other grammatical variations thereof, mean the number of antigen binding sites in an antibody molecule. These antigen recognition sites may recognize the same epitope or different epitopes.

As used herein, the term "carriers" may include pharmaceutically acceptable carriers, excipients, or stabilizers that are nontoxic to the cell or mammal being exposed thereto at the dosages and concentrations employed. Often the pharmaceutically acceptable carrier is an aqueous pH buffered solution. Examples of physiologically acceptable carriers include, but not limited to, buffers such as phosphate, citrate, and other organic acids; antioxidants including, but not limited to, ascorbic acid; low molecular weight (less than about 10 residues) polypeptide; proteins, such as, but not limited to, serum albumin, gelatin, or immunoglobulins; hydrophilic polymers such as, but not limited to, polyvinylpyrrolidone; amino acids such as, but not limited to, glycine, glutamine, asparagine, arginine or lysine; monosaccharides, disaccharides, and other carbohydrates including, but not limited to, glucose, mannose, or dextrins; chelating agents such as, but not limited to, EDTA; sugar alcohols such as, but not limited to, mannitol or sorbitol; salt-forming counterions such as, but not limited to, sodium; and/or nonionic surfactants such as, but not limited to, TWEEN; polyethylene glycol (PEG), and PLURONICS. Any combination of such components, including probable inclusion of a bacteriostat, may be useful to fill the formulations of the present disclosure.

The terms "conservative sequence modifications" or "conservative substitutions" as used herein may refer to amino acid modifications to a target epitope or antibodies and antigen-binding portions thereof of the disclosure that does not significantly affect or alter the binding characteristics of the heterodimeric immunoglobulin constructs of the present invention. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Such substitutions are typically based on the relative similarity of the amino acid side chain substituents, such as their hydrophobicity, hydrophilicity, charge, size etc. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

As used herein, the term "extracellular domain" or "extracellular domain of membrane receptors" refers to molecular recognition sequence(s) that typically includes extracellular regions outside the cell that recognize and bind the corresponding antigen or ligand, anchor the receptor at transmembrane domain on the cell surface, and are involved with the intracellular domain with intracellular kinase activity or signalling pathways. A ligand may refer to a protein, a small peptide, or a compound that can be recognized and bound by extracellular domain of membrane receptor. Immunogenic, mitogenic, or other stimulants could induce various cells to produce low molecular weight soluble proteins. It may modulate innate and adaptive immunity, hematopoiesis, cell growth, APSC pluripotent cells, and repair damaged tissue repair. Cytokines can be divided into interleukin, interferon, tumor necrosis factor superfamily, colony-stimulating factor, chemokines, growth factors. Protein expression tag refers to an amino acid sequence added at the N-terminus or C-terminus of the target protein, which can be a small peptide or a long amino acid. The addition of the tag could facilitate the correct folding of the protein, and can be used for the separation and purification of protein. It may be useful for reducing the degradation of proteins in the cell. Commonly used tags include, but are not limited to HA, SUMO, His, GST, GFP, and Flag.

As used herein, the term "Fab fragment" may refer to a recognition moiety that is a fragment of antigen binding fragment (Fab), equivalently the two arms of an antibody molecule, which is comprised of an integrated light chain and the VH and the CH1 domains of a heavy chain.

As used herein, the term "Fc" refers to the "fragment crystallisable" region, which is comprised of the CH2 and CH3 constant domains and is an interacting region of immunoglobulin that interacts with effector molecules or cells, e.g., Fc receptors.

As used herein, the term "Fc receptor" or "FcR" is used to describe a receptor that binds to an Fc region (e.g. the Fc region of an antibody or antibody fragment). The term includes the neonatal receptor, FcRn, which is responsible for the transfer of maternal IgGs to the fetus. Other Fc receptors include any one of FcγRI, FcγRIIA, FcγRIIB1, FcγRIIB2, FcγRIIIA, FcγRIIIB, FcεRI, FcεRII, FcαRI, and Fcα/μR.

The term "homology" as used herein may refer to the existence of shared structure between two compositions. The term "homology" in the context of proteins may refer to the amount (e.g., expressed in a percentage) of overlap between two or more amino acid and/or peptide sequences. In the context of nucleic acids, the term may refer to the amount (e.g., expressed in a percentage) of overlap between two or more nucleic acid sequences. As used herein, the percent (%) homology between two sequences is equivalent to the percent identity between the two sequences. The percent identity between the two sequences is a function of the number of identical positions shared by the sequences (i.e., % homology=# of identical positions/total # of positions ×100), taking into account the number of gaps, and the length of each gap, which need to be introduced for optimal alignment of the two sequences. The comparison of sequences and determination of percent identity between two sequences can be accomplished using a mathematical algorithm. Such homology is well-represented in the art via local alignment tools and/or algorithms, and may include pairwise alignment, multiple sequence alignment methods, structural alignment methods, and/or phylogenetic analysis methods. Where sequences differ in conservative substitutions, the percent sequence identity may be, but not necessarily is, adjusted upwards to correct for the conservative nature of the substitution. Means for making this adjustment are well known to those of skill in the art. Typically, but not necessarily, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1.

As used herein, the term "immunoglobulin" refers to a symmetrical structure with four polypeptide chains, including two heavy chains with longer sequence containing 450-550 amino acid residues and higher relative molecular mass between 55000-70,000 Da and two light chains (L chain) with shorter sequence containing about 210 amino acid residues and smaller relative molecular mass about 24,000 Da. There are significant differences in the N-terminus near the end of the 110-amino acid sequence in different immunoglobulin heavy and light chains, known as the variable region (variable region, V region), and the remaining amino acid sequence close to the C-terminal is relatively constant, which termed as Constant region (Constant region, C area). The variable region of the heavy chain accounts for approximately one-fourth of the whole heavy chain sequence and the constant region approximately accounts for three-fourths. IgGs have three constant regions within the H chain, called CH1, CH2 and CH3. The constant region is both the skeleton of the immunoglobulin molecule and one of the sites that activate the immune response. In the present invention, the constant region involves the region where the first polypeptides interact with the second polypeptides, wherein the region comprises amino acids located in CH3 domain. These amino acids include but are not limited to: glutamine347, tyrosine349, threonine350, leucine351, serine354, arginine355, aspartic acid356, glutamic acid357, lysine360, serine364, threonine366, leucine368, lysine370, asparagine390, lysine392, threonine394, proline395, valine397, aspartic acid399, serine400, phenylalanine405, tyrosine407, lysine409, and lysine439.

As used herein, the terms "purified" or "isolated" antibody, peptide, polypeptide, or protein may refer to a peptide, polypeptide, or protein, that has been separated from other proteins, lipids, and nucleic acids with which it is naturally associated. The polypeptide/protein can constitute at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis.

As used herein, the term "scFv" may refer to a single-chain variable fragment. scFv is a fusion protein of the variable regions of the heavy ($V_H$) and light chains ($V_L$) of immunoglobulins, connected with a linker peptide. The linker peptide can be from about 5 to 40 amino acids or from about 10 to 30 amino acids or about 5, 10, 15, 20, 25, 30, 35, or 40 amino acids in length. An exemplary linker is GGGGSGGGGSGGGGS (SEQ ID NO: 72).

The terms "specific binding," "selective binding," "selectively binds," and "specifically binds," may refer to antibody binding to an epitope on a predetermined antigen but not to other antigens. Typically, the antibody binds with an equilibrium dissociation constant ($K_D$) of approximately less than $10^{-6}$M, such as approximately less than $10^{-7}$ M, $10^{-8}$ M, $10^{-9}$M or $10^{-10}$ M or even lower when determined by, e.g., equilibrium dialysis or surface plasmon resonance (SPR) technology in a BIACORE® 2000 surface plasmon resonance instrument using the predetermined antigen, e.g., an epitope on Her2, PD-L1, Trop2, CD3, and/or CD20, as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen.

As used herein, the terms "subject" or "patient" may refer to a biological system to which a treatment can be administered. A biological system can include, for example, an individual cell, a set of cells (e.g., a cell culture), an organ, a tissue, or a multi-cellular organism. A subject of the present invention may include birds, reptiles, mammals and the like. Preferably, the mammal comprises rodents and primates, including human.

As used herein, the term "treating" or "treatment" of a disease may refer to executing a protocol, which may include administering one or more drugs to a patient (human or otherwise), in an effort to alleviate signs or symptoms of the disease. Alleviation can occur prior to signs or symptoms of the disease appearing as well as after their appearance. Thus, "treating" or "treatment" includes "preventing" or "prevention" of disease. In addition, "treating" or "treatment" does not require complete alleviation of signs or symptoms, does not require a cure, and specifically includes protocols that may have only a marginal effect on the patient.

As used herein, the term "variant Fc region" refers to amino acid sequence that differs from that of a native sequence Fc region (or portions thereof) by virtue of at least one amino acid modification (e.g., substitution, insertion, or deletion), including heterodimeric variants in which the heavy chain subunit sequences may differ from one another. Exemplary amino acid modifications of the present disclosure include T366L, D399R, L351E, Y407L, and/or K409V in the CH3 region.

As used herein and in the appended claims, the singular forms "a", "and" and "the" include plural references unless the context clearly dictates otherwise The term "about" refers to a range of values which would not be considered by a person of ordinary skill in the art as substantially different from the baseline values. For example, the term "about" may refer to a value that is within 20%, 15%, 10%, 9%, 8%, 7%, 6%, 5%, 4%, 3%, 2%, 1%, 0.5%, 0.1%, 0.05%, or 0.01% of the stated value, as well as values intervening such stated values, for which context will define.

The term "binding member" as used herein refers to an agent, e.g., a protein or a protein complex (such as antibody or a fragment thereof), a small molecule, and the like, that specifically binds to a target, such as an Fc receptor. An Fc receptor binding member refers to such an agent that specifically binds to an Fc receptor. The terms "specific binding," "specifically binds," and the like, refer to the preferential binding to a molecule relative to other molecules or moieties in a solution or reaction mixture. In some embodiments, the affinity between a binding member and the target to which it specifically binds is characterized by a $K_d$ (dissociation constant) of $10^{-6}$ M or less, such as $10^{-7}$ M, $10^{-8}$ M, $10^{-9}$ M, $10^{-10}$ M or less.

As used herein, the term "recognition moieties" refers to regions of an agent that can interact specifically with target molecules (e.g., antigens, ligands, receptors, substrates) in a high degree of selectivity. Representative recognition moieties include: a variable region of an antibody, a structural variant of an antibody variable region, a binding domain of a receptor, a binding domain of a ligand or a binding domain of an enzyme. In the present disclosure, a recognition moiety is identified as a cognate recognition moiety to the chain it is associated with. The association can be covalent or non-covalent in nature depending on the context and the surroundings. For example, the bispecific heterodimeric antibody of the present disclosure has the recognition moieties covalently linked to their respective chains, while a halfmer of such bispecific antibody can be associated, at least in part, non-covalently with the constituent chain under a sufficiently reducing condition.

As used herein, the term "physiological condition" or "physiological conditions" refers to a condition or conditions of a surrounding environment that may occur in nature for an organism or cell system or a condition in which some variables (e.g, temperature) are allowed to lie out of the typical range observable in a living organism but nonetheless supportive of some functioning of the bispecific heterodimeric antibody of the disclosure. A non-limiting example of a physiological condition is the temperature, ionic strength, pH, and concentration of ions (e.g., $Ca^{2+}$ or $Mg^{2+}$) normally found in or surrounding a cell such as a mammalian cell. A temperature range of about 2-40° C. (e.g., 20-40° C.), atmospheric pressure of about 1, pH of about 6-8, glucose concentration of about 1-20 mM, about atmospheric oxygen concentration, and earth gravity are also examples of physiological conditions. As used herein, the term can also be combined with other specific limitations in characterizing a condition. It is to be understood that in such cases the term should be properly interpreted within the context of the condition so characterized. For example, when an aqueous solution is described herein as being under physiological conditions and sufficiently reducing, e.g., containing 1 mM dithiothreitol, such as in phosphate buffered saline (PBS) at 2-4° C. with 1 mM dithiothreitol, it is not meant that this solution as a whole is literally supportive of functioning of an antibody even in the presence of the reductant, but it is meant that apart from dithiothreitol, the rest of the elements or variables in the solution lie within the range considered supportive.

As used herein, the term "essentially free" refers to levels of a particular component, such as a polypeptide, that are undetectable using routine detection methods and protocols known to the skilled artisan, such as Western Blot, ELISA, RIA, HPLC (including chiral HPLC, chiral HPLC/MS, LC/MS/MS etc.), thin layer chromatography, mass spectrometry, polarimetry measurements, gas-chromatography-mass spectrometry, or others.

Publications disclosed herein are provided solely for their disclosure prior to the filing date of the present disclosure. Nothing herein is to be construed as an admission that the present disclosure is not entitled to antedate such publication. Further, the dates of publication provided may be different from the actual publication dates which may need to be independently confirmed.

Each of the applications and patents cited in this text, as well as each document or reference, patent or non-patent literature, cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference in their entirety. More generally, documents or references are cited in this text, either in a Reference List before the claims; or in the text itself; and, each of these documents or references ("herein-cited references"), as well as each document or reference cited in each of the herein-cited references (including any manufacturer's specifications, instructions, etc.), is hereby expressly incorporated herein by reference.

The following non-limiting examples serve to further illustrate the present disclosure.

VII. EXAMPLES

Example 1—Mutation Sites for Heterodimer Screening

Mutations were introduced in the CH3 domain of IgG1 heavy chain regions to promote heterodimerization. The most important amino acids in the interaction between two IgG1 homologous CH3 domains (indicated hereinafter as CH3-A and CH3-B) were analyzed, as indicated by J. Biol. Chem. 2010, 285:19637-19646, hereby incorporated by reference in its entirety. From Protein Data Bank (PDB), 27 antibody sequences were searched and the amino acids were chosen according to the criteria based on the contact-based method, wherein interface residues are defined as residues whose sidechain heavy atoms are positioned closer than a specified limit 4.5 Å from the heavy atoms of any residues in the second chain.

Amino acids in the CH3 interface were additionally screened by alanine mutation, and the changes in free energy of dissociation and unfolding by guanidine hydrochloride denaturation were detected to select the amino acids that influenced the energy most, compared with those of the wild type. The results showed that mutations in Thr366, Leu368, Phe405, Tyr407, Lys409 caused a free energy change of more than 2 kcal/mol.; see also Biochemistry. Jun. 30, 1998; 37(26):9266-73, hereby incorporated by reference in its entirety. The distance of amino acids in the interface was additionally analyzed by Pymol and DS software, results of which are shown in Table 1. Hydrogen bonds between interfaces are marked in italics and underline. Based on the distance of amino acid in the interface and the alanine mutation scanning results, the following mutation sites to promote heterodimer formation were selected: Thr366, Asp399 in the first polypeptide/CH3 domain, and Leu351, Tyr407, and Lys409 in the second polypeptide/CH3 domain.

TABLE 1

Distance of heavy atoms in the CH3 interface

| A chain | B chain(unit: Å) | | | |
|---|---|---|---|---|
| GLN 347 | | | LYS 360 3.9 | |
| TYR 349 | SER 354 3.7 | ASP 356 3.9 | GLU 357 3.6 | LYS 360 4.1 |
| THR 350 | SER 354 3.8 | | ARG355 5.9 | |
| *LEU 351* | LEU 351 4.1 | SER 354 3.6 | *THR 366 3.8* | |
| SER 354 | TYR 349 4.1 | THR 350 3.8 | LEU 351 3.8 | |
| ARG 355 | | THR 350 5.9 | | |
| *ASP 356* | TYR 349 3.9 | | *LYS 439 2.8* | |
| GLU 357 | TYR 349 3.7 | | LYS 370 4.2 | |
| LYS 360 | GLN 347 3.8 | | TYR 349 4.1 | |
| SER 364 | LEU 368 3.9 | | LYS 370 3.9 | |
| *THR 366* | LEU 351 3.7 | | *TYR 407 2.9* | |
| LEU 368 | SER 364 3.8 | | LYS 409 4.2 | |
| LYS 370 | GLU 357 3.9 | | SER 364 4.1 | |
| ASN 390 | | SER 400 3.5 | | |
| LYS 392 | ASP 399 3.6 | SER 400 4.0 | PHE 405 3.7 | |
| THR 394 | THR 394 3.7 | VAL 397 4.1 | PHE 405 4.0 | TYR 407 4.3 |
| PRO 395 | | VAL 397 3.9 | | |
| VAL 397 | THR 394 4.0 | | PRO 395 4.0 | |
| *ASP 399* | LYS 392 3.7 | | *LYS 409 2.8* | |
| *SER 400* | ASN 390 3.2 | | LYS 392 4.1 | |
| PHE 405 | LYS 392 3.5 | THR 394 4.6 | LYS 409 3.6 | |
| *TYR 407* | *THR 366 2.7* | THR 394 4.3 | TYR 407 3.9 | LYS 409 3.4 |
| *LYS 409* | LEU 368 4.0 | *ASP 399 2.8* | PHE 405 4.0 | TYR 407 3.6 |
| *LYS 439* | | *ASP 356 2.9* | | |

Example 2—Eukaryotic Cell Display Library Construction for Fc Heterodimer 2.1—Construction of the Display Vector for the Fc Heterodimer The display vector of Fc heterodimer pDis3 was modified from display vector pDisplay (Invitrogen, Cat. No. V66020). The PDGFR gene and myc gene thereof were deleted by NotI (NEB, Cat. No. R-0189S)/SfiI (NEB, Cat. No. R-0123S) digestion. The MCS (Multiple cloning site) was made by amplifying the plasmid of the pDisplay vector with the following primers: TGGGGCCCAGCCGGCCA-GATCT (SEQ ID NO: 1) and ATAAGAATGCGGCCGCGTCGACCTGCA (SEQ ID NO: 2). These primers have NotI/SfiI restriction sites respectively. The MCS was cleaved by NotI/SfiI restriction sites and inserted into above-mentioned digested vector. This resulted in the intermediate product pDisvector.

The F1 ori gene in pDis was deleted and Orip was inserted by following method. The Orip gene was amplified from pTT5 vector (Biovetor, Cat. No. 3574108) using the following primers, which contains Ssp I (NEB, Cat. No. R1032S) restriction site: 5'-ATCGAGTCAATATTAGGGT-TAGTAAAAGGGTCCTAAGGAAC (SEQ ID NO: 3), 5'-CAGTCGATAATATTAAGAATTAATTCT-CATGTTTGACAGCTTAT (SEQ ID NO: 4). Then the Orip gene was cleaved by SspI and ligated to the SspI digested pDis vector. This resulted in the pDis1 vector. Next, the neo-resistant gene was deleted from the pDis1 vector by AvrII (NEB, Cat. No. R0174S) digestion. The hygroresistant gene was inserted by amplification of the pCEP4 (Invitrogen, Cat. No. V04450) with the following primers to add AvrII restriction site:

upstream primer 5'-TAGccTcccccTAGGGTGGGcGAAGAAcTccAGcATG (SEQ ID NO: 5), 5'-TTTG-GAGGCCTAGGCTTTTGCAAAGATCGATCAAGA-GACAGGATGAGGA (SEQ ID NO: 6). After digestion, the hygro gene was inserted into pDis1 vector, resulting in the pDis2 vector.

Figure 1:
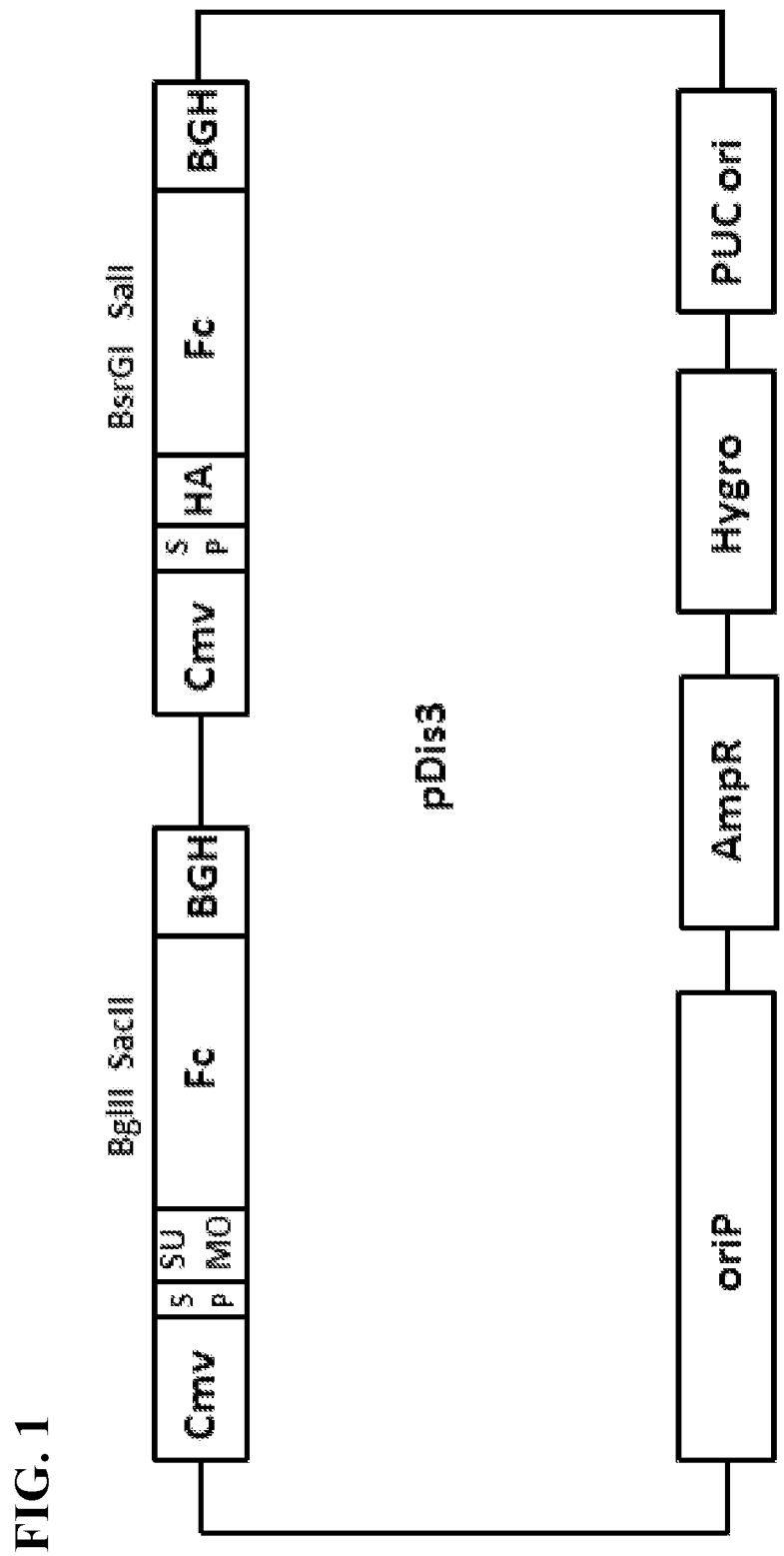

A DNA sequence (SEQ ID NO: 7) was synthesized by GENEWIZ company of China. This sequence from left to right comprises SUMO gene (from CHAMPION™ pET SUMO vector, Invitrogen, Cat. No. K30001), human Fc gene (hereinafter designated as Fc1, comprising CH3-A domain), bovine growth hormone (BGH) polyadenylation signal, signal peptide gene (from pDisplay vector), human influenza hemagglutinin (HA) gene (Genbank: NC_007362.1, from No. 98 to No. 106 amino acids) and human Fc gene (hereinafter designated as Fc2, comprising CH3-B domain). Two enzyme restriction sites SfiI and PstI are at opposite ends of the whole gene sequences. Fc sequence, SUMO sequence and HA sequence were optimized according to mammalian codon bias. Fc1 domain has BglII/SacII restriction sites and Fc2 domain has BsrGI/SalI restriction sites. The enzyme restriction sites used do not change Fc amino acid sequences. DNA sequences and pDis2 were digested using SfiI/PstI, and then ligated into pDis2, which resulted in the final vector pDis3, as shown in FIG. 1.

2.2 Construction of the Heterodimeric Fc Library

The pUC57-TCZHC (by GENEWIZ, China) contained natural human Fc sequences. The first site-directed random Fc sequences were made by amplifying the pUC57-TCZHC with the degenerate primers which degenerate codon NNS, which made the amino acids at position 366 and position 399 of Fc1 randomly mutate to 20 kinds of different natural amino acids. The upstream primer was TCCCAGCCGG-GATGAGCTGACCAAGAACCAAGTCTCCCTCNN-STGCCTGGTCAAGGGATTCTAC CCTTC (SEQ ID NO: 8), and the downstream primer was GTCCACGGT-GAGCTTGGAGTACAGGAAGAAGGATCCGTCGCTS NNCAGGACGGGGGGGGTTGTC TT (SEQ ID NO: 9).

The second Fc gene was amplified from pUC57-TCZHC with the following primers: the upstream primer was TACTCCAAGCTCACCGTGGAcAAGAGc (SEQ ID NO: 10), and the downstream primer was CGATCCAATC-GATGGAAGATCTTCATCATTTGCCGGGGCT-GAGGCTCAGGCT (SEQ ID NO: 11).

The site-directed random Fc1 fragment was spliced together by overlap extension using the following primers: 5'-CAAGGGCCAGCCGCGGGAACCT-CAAGTGTATACCCTCCCTCCCAGCCGGGAT-GAGCTGACCAAG AACCAA (SEQ ID NO: 12),5 CGATCCAATCGATGGAAGATCTTCATCAT-TTGCCGGGGCTGAGGCTCAGGCT (SEQ ID NO: 13).

The Fc1 fragment was subcloned into the pDis3 vector by BglII (NEB, Cat No. R0144S) and SacII (NEB, Cat. No. R0157S) restriction sites. Then the desalted construct was transformed into *E. coli* Top10 strain using a Bio-Rad GENE PULSER XCELL™ electroporation apparatus.

The transformants were plated directly on selective agar media containing 100 mg/L ampicillin. The mutated library size was calculated by the number of colonies. 20 colonies were picked randomly and verified the variety of insertion by DNA sequencing. The Fc1 site-directed random mutation library was constructed until reaching $10^5$ capacity by repeated electroporation.

A plasmid extraction kit (Qiagen, Cat. No. 27106) was used to extract Fc1 site-directed random mutation library. The library was used as a template for Fc1+Fc2 site-directed random mutation library construction. The site-directed random Fc2 fragment was cloned into Fc1 library using degenerate primers to add BsrGI and SalI restriction sites 5' and 3' respectively:

```
                                    (SEQ ID NO: 14)
5'-GGCCAGCCCAGGGAACCTCAAGTGTACACCNNSCCTCCCAGCCGGGA
TGAGCTG,, (SEQ ID NO: 15)
5'-GCCCTGTTGCCACCGGCTCTTGTCGACGGTGAGSNNGGASNNCAGGA
AGAAGGATCCGTCGCT.
```

There are BsrGI and SalI sites in the primers, and this method introduced 20 amino acids into 351, 407 and 409 sites of Fc using NNS codon. The Fc2 fragment and the linearized Fc2 vector (by BsrGI (NEB, Cat. No. R3575L) and SalI (NEB, Cat. No. R3138L) digestion) were co-transformed into the *E. coli* Top10 strain using a Bio-Rad GENE PULSER XCELL™ electroporation apparatus.

Figure 2:
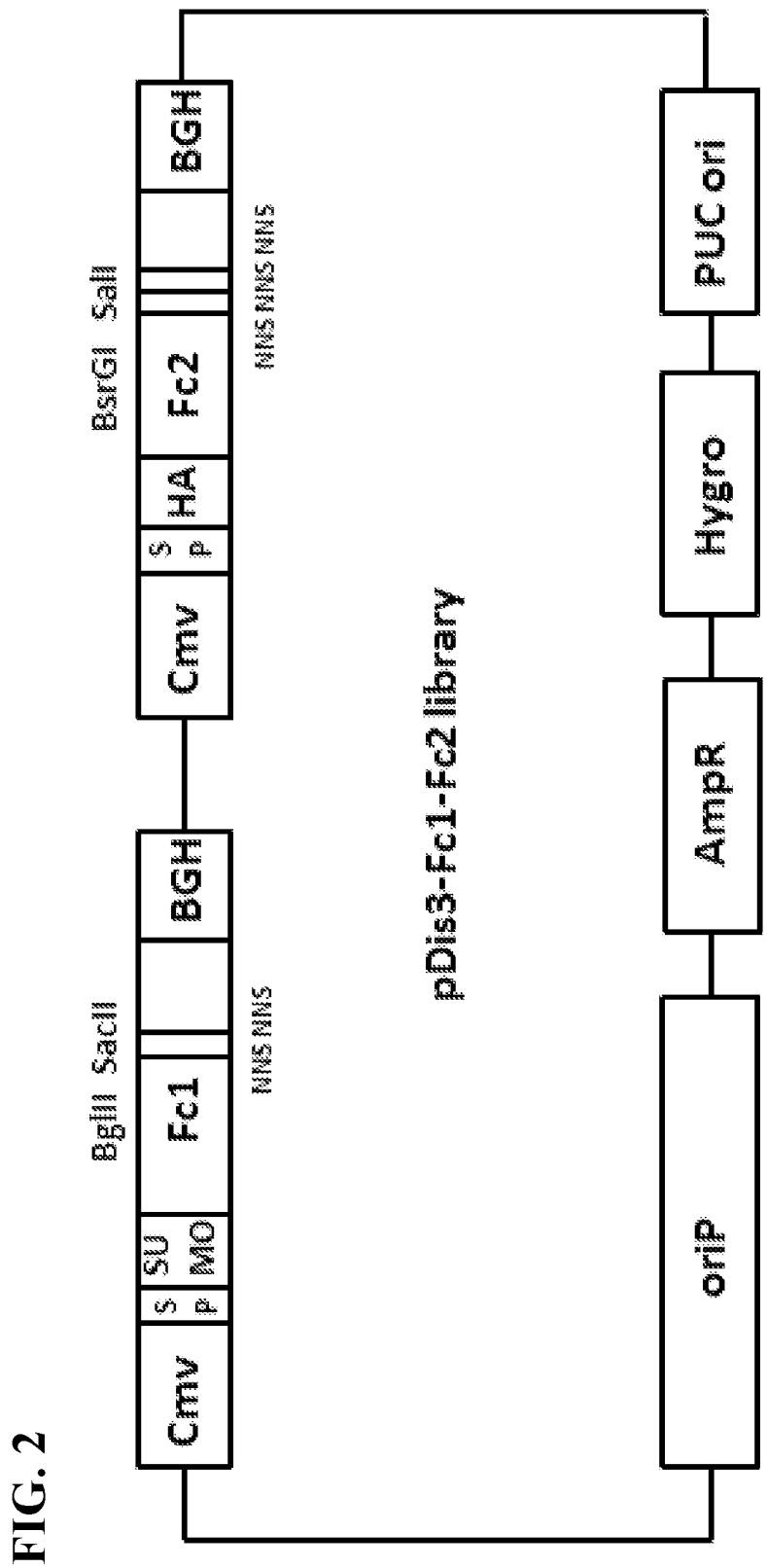
FIG. 2 represents the structure of a heterodimer Fc library.

The transformants were plated directly on selective agar media containing 100 mg/L ampicillin. The Fc1+Fc2 site-directed random mutation library was constructed until reaching $3 \times 10^8$ capacity by repeated electroporation. The processes of construction of the heterodimeric Fc library are shown in FIG. 2. The plasmids of Fc1+Fc2 library were extracted by QIAGEN® plasmid Plus 96 kits (Qiagen, Cat. No. 16181) through picking single colonies randomly from selective agar media.

The purified plasmid was transfected into FREE-STYLE™ 293-F Cells (Invitrogen, Cat. No. R79007) in a 96-well plate. On the day before the transfection, 293-F cells were subcultured and expanded to allow them to grow overnight. On the day of transfection, cells were collected by centrifugation and re-suspended using fresh FREE-STYLE™ 293 expression medium (Gibco, Cat. No. 12338001) to a final density of $200 \times 10^5$ viable cells/mL. The plasmids (final concentration 36.67 µg/mL) were transiently co-transfected at the indicated molar ratios with polyethylenimine (25 kDa, final concentration 55 µg/mL, Alfa Aesar, Cat. No. 43896), mixed and incubated at 37° C. for 1 hour. Fresh medium was added as 19-fold of transfection volume and continued to incubate. The cell culture supernatant was harvested 5-6 days after transfection.

Figure 3:
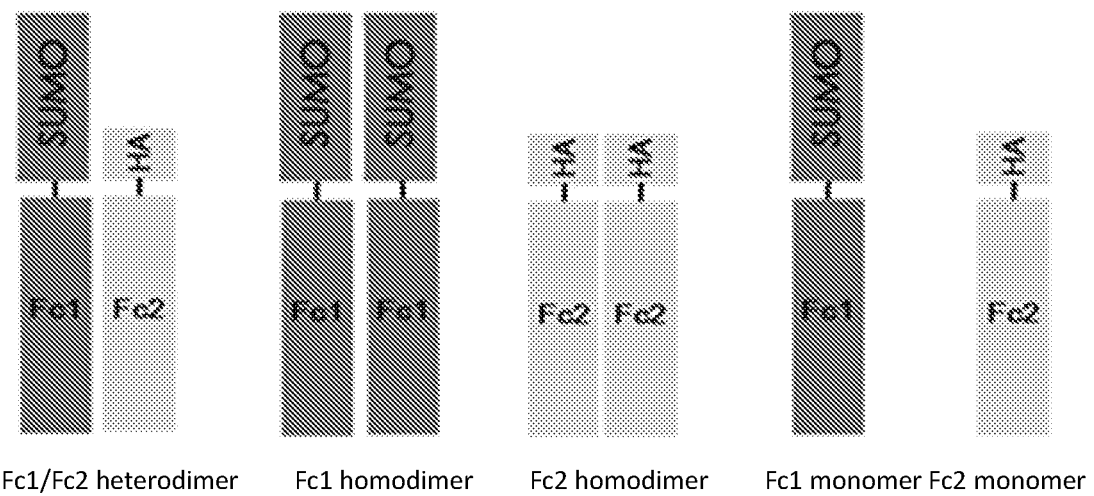
FIG. 3 represents homodimer and heterodimer pairing.

As shown in FIG. 3, heterodimeric Fc with two different tags has 5 kinds of structures in the supernatant. The heterodimer was detected by ELISA. Briefly, a 96-well plate was coated with anti-HA antibody (Abcam, Cat. No. ab181181) in carbonate buffer pH 9.6 and washed by PBST (Sigma, Cat. No. P-3563). Any nonspecific binding sites on the surface of plate were blocked by PBST containing 5% skim milk. The plate was washed using PBST. The supernatant was diluted by PBST containing 1% BSA and added to the plate, incubate at 25° C. for 1 hour.

The plate was washed by PBST to remove unbound sample. Anti-SUMO antibody (Abcam, Cat. No. ab179907) labeled biotin was diluted by PBST containing 5% skim milk and added to the plate, then incubated at 25° C. for 1 hour. The plate was washed by PBST. Then the secondary antibody, Streptomycin avidin labeled horseradish peroxidase (Abcam, Cat. No. 59653) was diluted by PBST containing 5% skim milk and added to the plate, then incubated at 25° C. for 1 hour. The plate was washed by PBST. TMB (BD OptEIA, Cat. No. 555214) was added to be converted by the enzyme into a color for 10 minutes. 1 M H2SO4 was added to stop coloration. Absorbance at 450 nm was read by Microplate Reader.

The 20 clones with highest OD values were selected in each screening round and expanded correspondent cells in 96-well plate. The proteins were purified from the culture supernatants using Protein-A agarose chromatography (ACRO Biosystems, Cat. No. MA0422-S1) and analyzed by SDS-PAGE. The clone with highest heterodimerization yield was obtained and verified by DNA sequencing after multi-rounds screening. Results are shown in Table 2 below. The amino acid sequences of positive clones are shown in SEQ ID NOS: 16-31.

TABLE 2

Fc1 and Fc2 sequencing result

| | Fc1 | | | Fc2 | | | | Heterodimer ratio (SDS-PAGE, by quantity One) |
|---|---|---|---|---|---|---|---|---|
| | 366 | 399 | SEQ ID NO. | 351 | 407 | 409 | SEQ ID NO. | |
| #1 | L | C | SEQ ID NO: 16 | G | L | C | SEQ ID NO: 17 | 61.45 |
| #6 | L | C | SEQ ID NO: 18 | Y | A | P | SEQ ID NO: 19 | 57.59 |
| #23 | V | T | SEQ ID NO: 20 | K | T | Q | SEQ ID NO: 21 | 52.13 |
| #41 | L | A | SEQ ID NO: 22 | W | H | R | SEQ ID NO: 23 | 52.33 |
| #46 | P | N | SEQ ID NO: 24 | V | P | S | SEQ ID NO: 25 | 47.77 |
| #53 | P | I | SEQ ID NO: 26 | P | F | F | SEQ ID NO: 27 | 42.97 |
| #65 | W | G | SEQ ID NO: 28 | D | P | S | SEQ ID NO: 29 | 47.30 |
| #76 | L | R | SEQ ID NO: 30 | E | L | V | SEQ ID NO: 31 | 69.73 |

Example 3—Construction of a Vector for Heterodimeric Antibody Expression

X0GC expression vectors were constructed encoding the heavy chain and light chain of anti HER2 antibody, wherein antibody variable region sequences were from www-.drugbank.ca/drugs/DB00072. The constant domain for heavy chain used was human IgG1 (Fc1). The nucleic acid sequences encoding the variable light chain ($V_L$) was SEQ ID NO: 32 and the amino acid sequence was SEQ NO: 33. Nucleic acid sequences encoding the constant domain of light chain ($C_L$) was SEQ ID NO: 34, and the amino acid sequence was SEQ NO: 35. The nucleic acid sequence encoding the variable heavy chain ($V_H$) was SEQ ID NO: 36, and the amino acid sequence was SEQ ID NO: 37. The nucleic acid sequence encoding the constant heavy chain ($C_H$) was SEQ ID NO: 38, and the amino acid sequence was SEQ ID NO: 39.

The $V_L$, $C_L$, $V_H$, $C_H$ were amplified by polymerase chain reaction (PCR) as follows. The reaction system was H$_2$O 8.9 µL, 5× PHUSION® DNA polymerase buffer 4 µl, 1 mM dNTP 4 µL, upstream primer 1 µL, downstream primer 1 µL, PHUSION® DNA polymerase (NEB, Cat. No. F-530L) 0.1 µL, and template 1 µL. The PCR products of the variable and constant fragments were separated on 1.5% agarose gel electrophoresis and were recovered using DNA purification kit (Promega, Cat. No. A9282). The next round of PCR was carried on using the recovered variable and constant fragments as templates in conjunction with the upstream primers of variable fragments and downstream primers of constant fragments. Then the full-length fragments of light chain or heavy chain were obtained after recovering. The fragments and X0GC vector were respectively digested and linked by the same EcoRI (NEB, Cat. No. R3101L)/HindIII (NEB, Cat. No. R3104L) restriction sites. The digestion system was 10× reaction buffer 32 µL, EcoRI and HindIII 0.5 µL, the fragments of recycling 3 µL, H$_2$O 14.5 µL. The reaction occurred at 37° C. for 3 hours. The ligation system was 10×T4 DNA ligase buffer 2 µL, T4 DNA ligase (New England Biolabs, Cat. No. M0202V) 0.5 µL, the fragments of recycling 3 µL, the vector of recycling 3 µL, H$_2$O 11.5 µL. The reaction occurred at room temperature for 12 hours. The constructs were transformed into *E. coli* DH5α strain (TIANGEN™, Cat. No. CB104, China), then the plasmid was generated with either heavy chain (Fc1) or light chain of antibody for expression in a eukaryotic cell.

X0GC expression vectors were constructed encoding the heavy chain of anti HER2 antibody. The sequences in constant heavy region were IgG1 (Fc2) (SEQ ID NO: 40). The sequences of amino acid were SEQ NO: 41. The expression plasmid of heavy chain of antibody was used for expressing the antibody's heavy chain (Fc2) in eukaryocyte.

X0GC expression vectors were constructed encoding the heavy chain and light chain of anti CD20 antibody. The variable sequences of antibody came from U.S. Pat. No. 5,736,137, hereby incorporated by reference in its entirety. The sequences in constant heavy region were from human IgG1 (Fc1). The nucleic acid sequence encoding the variable light chain ($V_L$) was SEQ ID NO: 42, and the amino acid sequence was SEQ ID NO: 43. The amino acid sequence of the constant light chain ($C_L$) was SEQ ID NO: 35. The nucleic acid sequence encoding the variable heavy chain ($V_H$) was SEQ ID NO: 44, and the amino acid sequence was SEQ ID NO: 45. The nucleic acid sequence encoding the constant heavy chain ($C_H$) was SEQ ID NO: 46 or 47, the amino acid was SEQ ID NO: 48 or 49. The expression vector was created as described above. The expression plasmid of heavy chain or light chain of antibody was used for expressing the heavy chain (Fc1 or Fc2) or light chain in a eukaryocyte.

X0GC expression vectors were constructed encoding the heavy chain and light chain of anti Trop-2 antibody as described above. The variable sequences of antibody came from WO/2003074566, hereby incorporated by reference in its entirety. The sequence in constant heavy chain was human IgG1 (Fc1). The nucleic acid sequences encoding the variable light chain ($V_L$) was SEQ ID NO: 50, and amino acid sequence was SEQ ID NO: 51. The amino acid sequence of constant light chain ($C_L$) was SEQ ID NO: 35. The nucleic acid sequence of variable heavy chain ($V_H$) was SEQ ID NO: 52, the amino acid sequence was SEQ ID NO: 53. The nucleic acid sequence encoding constant heavy chain ($C_H$) was SEQ ID NO: 54, amino acid sequence was SEQ ID NO: 55.

X0GC expression vectors were constructed encoding the heavy chain and light chain of anti PD-L1 antibody as described above. The variable sequences of antibody came from US/20100203056, hereby incorporated by reference in its entirety. The sequences in constant heavy region were from human IgG1 (Fc1). Nucleic acid sequence of variable light chain was SEQ ID NO: 56, amino acid sequence of variable light chain was SEQ ID NO: 57, amino acid sequences of constant light chain was SEQ ID NO: 35, nucleic acid sequence of the variable heavy chain was SEQ ID NO: 58, amino acid sequences of variable heavy chain was SEQ ID NO: 59, nucleic acid sequence of the constant heavy chain was SEQ ID NO: 60, and amino acid sequence of constant heavy chain was SEQ ID NO: 61.

X0GC expression vectors were constructed encoding anti CD3 scFv and human IgG1 (Fc2) fusion sequence as described above. The variable sequences of antibody came from U.S. Pat. No. 7,112,324, hereby incorporated by reference in its entirety. The sequence of constant heavy region was human IgG1 (Fc2). Nucleic acid sequence of variable domain was SEQ ID NO: 62, amino acid sequence of variable domain was SEQ ID NO: 63, nucleic acid sequence of constant domain was any one of SEQ ID NOs: 64-67, and amino acid sequence of constant domain was any one of SEQ ID NOs: 68-71. The expression plasmid of fusion sequences of anti CD3 scFv and human IgG1 (Fc2) was used for expressing fusion sequences of anti CD3 scFv and human IgG1 (Fc2) in eukaryotes.

Example 4—Expression of Heterodimeric Antibodies

Two expression vectors of heavy and light chains of antibody were transfected into FREESTYLE™ 293-F Cells (FREESTYLE™ 293-F Cells, Cat No. R79007, invitrogen). On the day prior to transfection, 293-F Cells were subcultured and expanded to allow grow overnight. On the day of transfection, cells were collected by centrifugation and resuspended using fresh FREESTYLE™ 293 expression medium (Gibco, Cat. No. 12338001) to a final density of 200×10$^5$ viable cells/mL. The plasmids (final concentration 36.67 µg/mL) were transiently co-transfected at the indicated molar ratios with polyethylenimine (25 kDa, final concentration 55 µg/uL, Alfa Aesar, Cat. No. 43896) gently mixed and incubated at 37° C., 120 rpm for 1 hour. Then fresh medium was added at 19-fold volume of transfection, and continued to incubate. The cell culture supernatant was harvested 5-6 days after transfection.

Three expression vectors were also transfected into cells. The heavy chain (human IgG1-Fc1) of antibody A, light chain of antibody A, and fusion sequences of antibody B' scFv and human IgG1-Fc2 were transfected together. There were Fc1 homodimer, scFv-Fc2 homodimer and Fc1/scFv-Fc2 heterodimer in the cell culture supernatant. Fc1/scFv-Fc2 heterodimer was the main product because of the mutual repulsion effect between Fc1 and Fc2. Additionally, Fc1 and Fc2 have a high tendency to form heterodimers.

The yields of anti-HER2-Fc1 and anti-CD3-Fc2 were 70-100 mg/L by ELISA. Before purification by columns, the supernatant was filtered through 0.22 μm filter to remove the cell debris at 4° C.

Example 5—Anti HER2/Anti CD3-scFv Heterodimeric Antibody Purification

Figure 4:
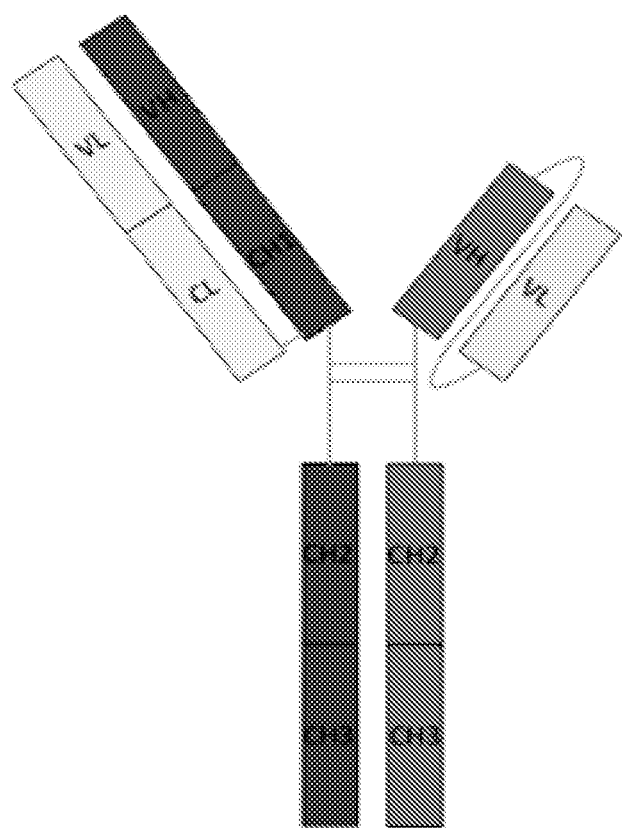
FIG. 4 represents the generic structure of an anti-HER2/anti CD3-scFv heterodimer.

The generic structure of an anti HER2/anti CD3-scFv heterodimeric antibody is shown in FIG. 4. The proteins were purified from the culture supernatants using Protein-A SEPHAROSE® Fast Flow (16 mm I.D., 22 ml, GE Healthcare). The collected proteins were concentrated by ultrafiltration tube (10 kDa molecular-weight cut-off) and changing buffer into PBS solution. Next, 3M $(NH_4)_2SO_4$ was added to a final concentration of 1 M with half volume of the solution. The proteins were diluted with buffer A (20 mM sodium phosphate, 1 M $(NH_4)_2SO_4$, pH 7.0).

Figure 5:
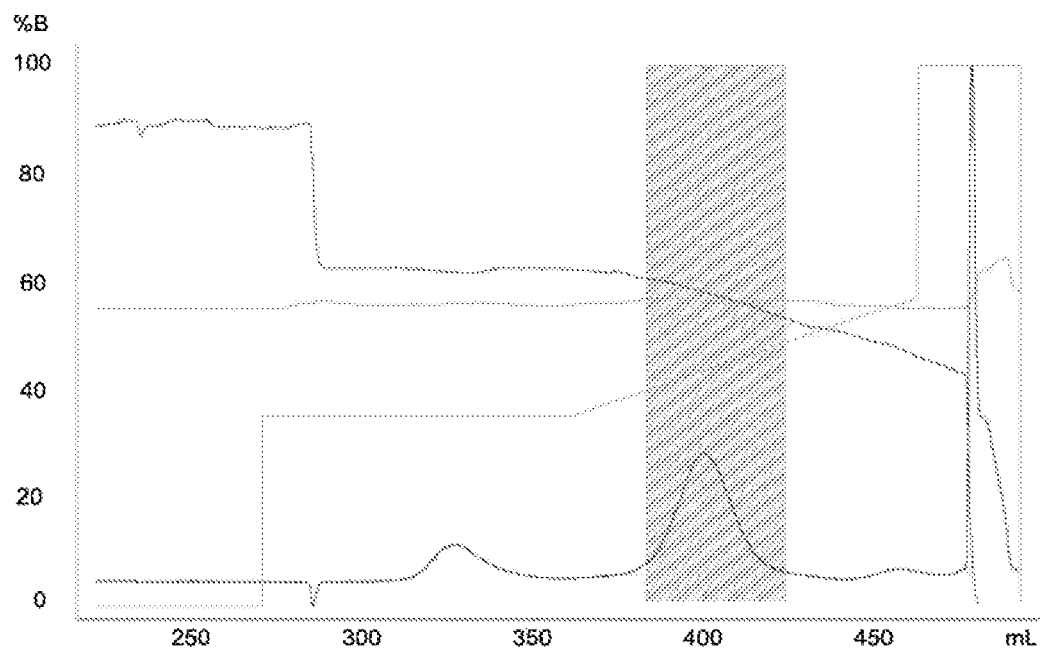
FIG. 5 represents the elution peak of the anti-HER2/anti CD3-scFv heterodimer.
Figure 6:
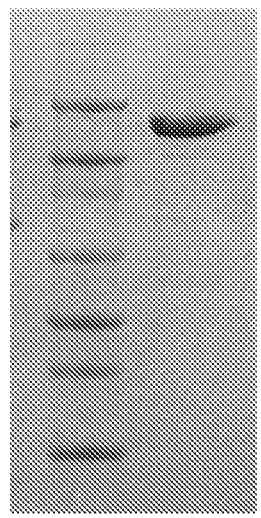
FIG. 6 represents the SDS-PAGE analysis of the anti-HER2/anti CD3-scFv heterodimer.
Figure 7:
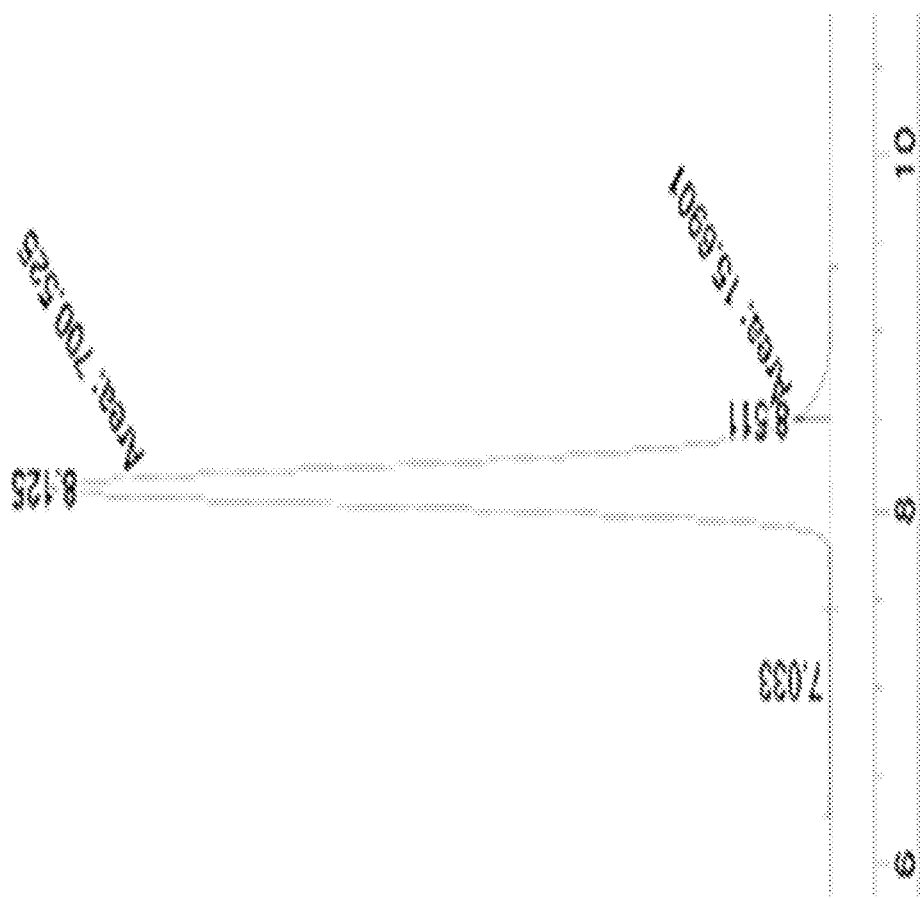
FIG. 7 represents the purity analysis of the anti-HER2/anti CD3-scFv heterodimer.

The following purification also used—AKTA explorer 100 (GEHealthcare) protein purification system. The proteins were purified by Source phenyl (16 mm I.D., 22 ml, GE Healthcare). The protein samples were loaded on the column previously equilibrated with buffer A (20 mM $Na_3PO_4$, 1 M $(NH_4)_2SO_4$, pH 7.0). The flow rate was 3 mL/min. Then the column was equilibrated with buffer A and washed 15 column volumes by gradient from buffer A (0% B) to 100% buffer B (20 mM Sodium phosphate, pH7.0) within 180 minutes. The flow rate was 2 mL/min. The fractions shown in FIG. 5 were pooled and concentrated with ultrafiltration tube (10 kDa molecular-weight cut-off) to change buffer into PBS solution. The proteins were filtered through 0.22 μm and preserved at 4° C. The purified protein were analyzed by SDS-PAGE. The result is shown in FIG. 6. The purity was 97.65% by size exclusion-high performance liquid chromatography (SEC-HPLC) (FIG. 7).

Figure 8A:
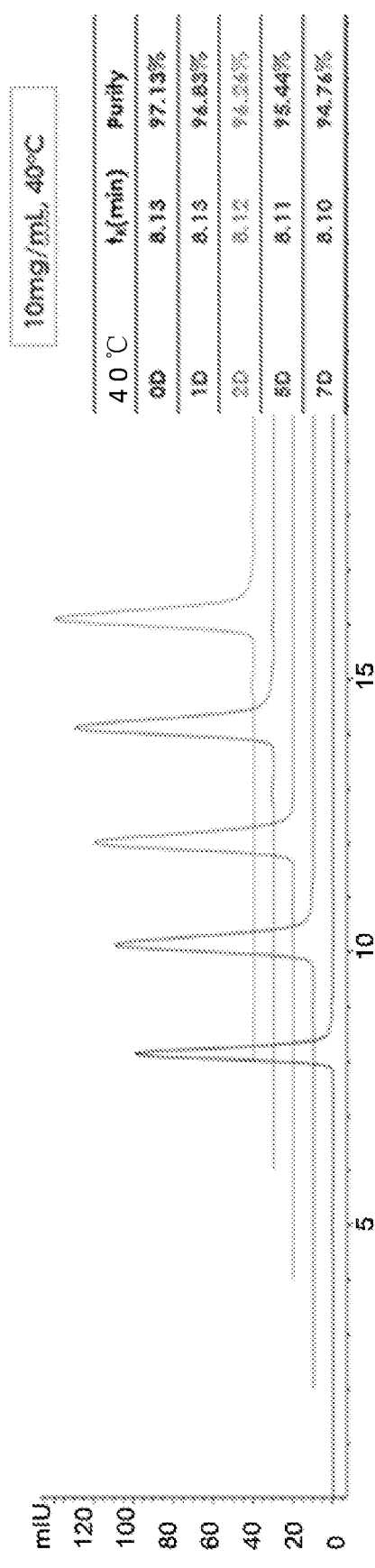
FIGS. 8A and 8B represent the stability of the anti-HER2/anti CD3-scFv heterodimer at different concentrations: 10 mg/mL 40° C.
Figure 8B:
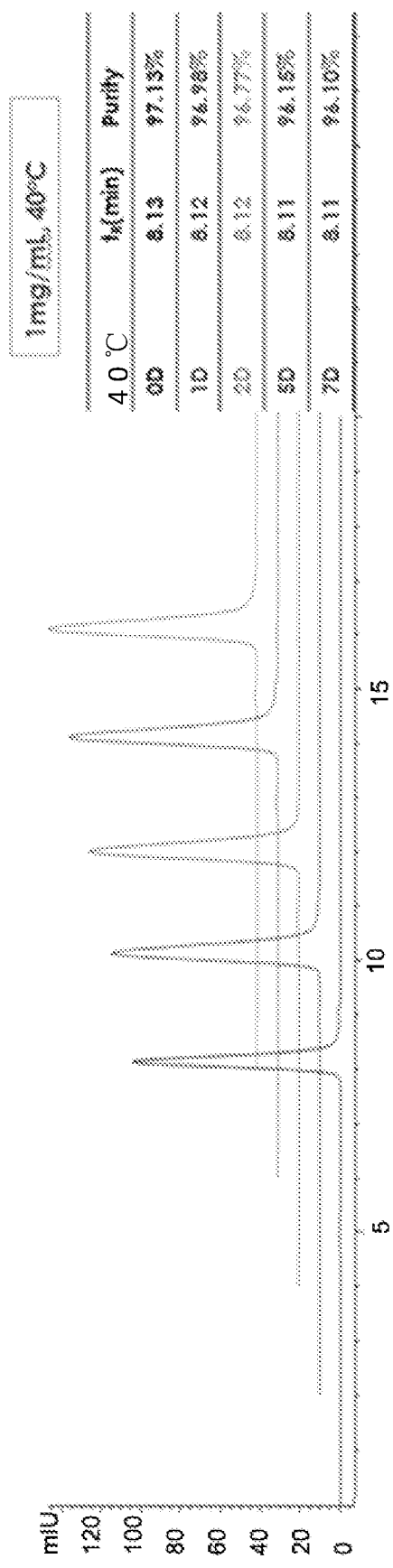

Example 6—Stability Test of Heterodimeric Anti-HER2/Anti-CD3-scFv Bispecific Antibody The fully sealed heterodimericanti-HER2/anti-CD3-scFv samples (1 mg/mL and 10 mg/mL) were stored in the incubator at 40° C. (BINDER, KBF240). Stability was tested with 20 sample at different time points (baseline (Day 0), Day 1, Day 2, Day 5, Day7) using high performance exclusion liquid chromatography (SEC-HPLC). The SEC-HPLC conditions were as follows: (1) chromatographic column: TSKGEL® G3000SWxl (Tosoh Bioscience), 5 μm, 7.8 mm×30 cm; (2) mobile phase: 5 mM PBS, 150 mM NaCl, pH 6.7; (3) flow rate: 0.6 mL/min; (4) UV detection wavelength: 280 nm; (5) acquisition time: 30 min. The instrument used was an Agilent 1200 Infinity chromatograph, using ChemStation Agilent to record the graph and calculate the proportion of the remaining monomer. As shown in FIG. 8 under the experimental conditions at 40° C., the heterodimericanti-HER2/anti-CD3-scFv did not undergo significant aggregation. The data demonstrated that the heterodimericanti-HER2/anti-CD3-scFv has good thermal stability.

Figure 9:
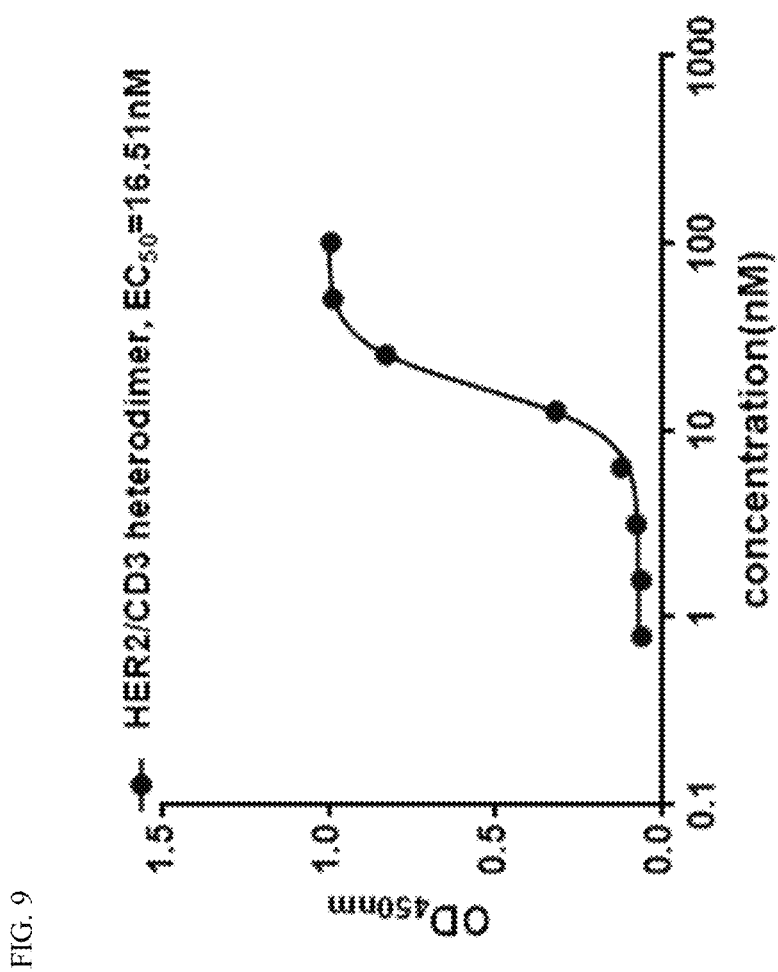
FIG. 9 represents the binding affinity of the anti-HER2/anti CD3-scFv heterodimer to FcRn.

Example 7—Binding Activity Between Heterodimeric Anti-HER2/Anti-CD3-scFv Bispecific Antibody and FcRn FcRn binding activity of heterodimeric anti-HER2/anti-CD3-scFv was tested by ELISA. Briefly, an ELISA plate was coated with anti-HER2/anti-CD3-scFv heterodimer and controls in carbonate/bicarbonate buffer (pH9.6) overnight at 4° C. The plate was washed 5 times with PBST (pH 6.0). 300 μL per well of PBST containing 0.5% BSA was added to block the plate and the plate was incubated for a minimum of 1 h at 25° C. The plate was washed as above, then 100 μL per well of FcRn-his tag (Sino Biological, Cat. No. CT009-H08H) at 1 μg/mL diluted in 0.5% BSA in PBST was added to each well and the plate was incubated for 2 h at 25° C. The plate was washed as above and then 100 μL per well of anti-his mouse antibody (CWBIO, Cat. No. CW0228) at 1:5000 dilution in 0.5% BSA in PBST was added and incubated for 1 h at 25° C. The plate was washed as above and then 100 μL per well of anti-mouse IgG antibody (Abcam, Cat. No AB7068) labeled by horseradish peroxidase (HRP) was added and incubated for 1 h at 25° C. The plate was washed as above and 100 μL per well of TMB was added and colorized for 10 min at room temperature. The reaction was stopped by the addition of 100 μL per well of 1 M $H_2SO_4$. The optical density at 450 nm was read using a microplate reader. As shown in FIG. 9, the heterodimeric anti-HER-2/anti-CD3-scFv binds to FcRn.

Example 8—In-Vitro Binding Activity of Heterodimeric Anti-HER2/Anti-CD3-scFv Bispecific Antibody Heterodimeric anti-HER2/anti-CD3-scFv was tested for binding activity to SK-BR-3 cells with high expression of HER2, and Jurkat cells with high expression of CD3 by flow cytometry (FACS).

SK-BR-3 cells and Jurkat cells were collected and washed once with cold assay buffer which is cold PBS (GIBCO, Cat No. 14190-235) containing 2% FBS (Hyclone, Cat. No. SH30084.03) respectively. Then, aliquots of SK-BR-3 cells ($1×10^6$/tube) were resuspended in cold assay buffer (200 μL DPBS containing 2% FBS), and incubated with 0.5 nM of heterodimeric anti-HER2/anti-CD3-scFv, or homodimer tetravalent anti-HER2/anti-CD3, or anti-HER2, or isotype control (human immunoglobulin, Jiangxi Boya Bio-pharmaceutical, Approval No. S19993012, China) on ice in the dark for 30 minutes. Aliquots of Jurkat cells were treated similarly except the concentration of those samples were changed to 5 nM. At the end of incubation, cells were washed twice with cold assay buffer, and then resuspended in cold assay buffer and incubated with 50-fold diluted anti-human IgG-FITC conjugate (ZSGB-Bio, Cat. No. ZF0306, China) on ice in the dark for 30 minutes. At the end of incubation, cells were washed twice with cold assay buffer and then resuspended in cold PBS. Flow cytometry was performed using FACS Calibur (Becton Dickinson). Results are indicated in Tables 3 and 4. The results indicated that the heterodimeric anti-HER2/anti-CD3-scFv construct bound to its antigens HER2 and CD3 with good activity.

TABLE 3

Binding activity to SK-BR-3 cells with HER2 high expression

| Sample | Mean Fluorescence Intensity (MFI) |
| --- | --- |
| Isotype | 2.88 |
| Anti-HER2 (Herceptin) | 20.55 |
| heterodimeric anti-HER2/anti-CD3 | 14.16 |

TABLE 4

Binding activity to Jurkat cells with CD3 high expression

| Sample | MFI |
| --- | --- |
| Isotype | 3.16 |
| Anti-HER2 (Herceptin) | 3.16 |
| heterodimeric anti-HER2/anti-CD3 | 5.19 |

Example 9—Simultaneous Binding Activity Against HER2 and CD3 of Heterodimeric Anti-HER2/Anti-CD3-scFv Bispecific Antibody Heterodimericanti-HER2/anti-CD3-scFv constructs were tested for simultaneous binding activity against HER2 and CD3 using SK-BR-3 cells and Jurkat cells by FACS.

SK-BR-3 cells were stained following the operation instruction of PKH26 kit (Sigma, Cat. No. SLBH4568V). Briefly, SK-BR-3 cells were collected and washed in serum-free medium once, and then prepared the SK-BR-3 cells into $2\times10^7$ cells/mL cell suspension and diluted the PKH26 to 4 μM respectively by using the Diluent C in the PKH26 kit. Next, they were mixed 1:1 to obtain the mixture in which cell density is $1\times10^7$ cells/mL while the concentration of PKH26 is 2 μM. Next, the mixture was incubated at room temperature for 1 minute, and then incubated with equal volume of FBS for 1 minute to terminate staining. The mixture was then centrifuged at 400 g for 10 minutes, washed with complete medium twice and then resuspended in the complete medium. Jurkat cells were stained according to the operation instruction of CFSE kit (Life technology, Cat. No. C34554). Briefly, CFSE was diluted to working concentration 0.5 μM with PBS, preheated at 37° C. Jurkat cells were centrifuged at 1000 rpm for 5 minutes and then resuspended in the preheated CFSE working solution, and incubated at 37° C. for 15 min. The stained Jurkat cells were centrifuged at 1000 rpm for 5 min and resuspended in complete medium, and incubated for 30 min. After incubation, the cells were washed with complete medium once and then resuspended in complete medium.

The above stained SK-BR-3 cells and Jurkat cells were collected by centrifugation and washed once with cold assay buffer which is cold PBS containing 2% FBS. The cells were resuspended at a cell density of $5\times10^6$ cells/mL in the cold assay buffer. SK-BR-3 cells and Jurkat cells were mixed in proportion of 1:1 and pipetted 100 μL aliquot of the mixtures for each tube (namely $2.5\times10^5$ SK-BR-3 cells and $2.5\times10^5$ Jurkat cells). Next, 100 μL of heterodimeric anti-HER2/anti-CD3-scFv sample or isotype control was added (human immunoglobulin, Jiangxi BoyaBio-pharmaceutical, S19993012). Diluted in the assay buffer, the final concentration was 5 nM. The tubes were incubated for 30 minutes on ice in the dark, washed twice with cold assay buffer, and then resuspended in 500 μL of cold PBS. Flow cytometry was performed using FACS Calibur.

As shown in FIG. 10, heterodimeric anti-HER2/anti-CD3-scFv can induce the association of SK-BR-3 and Jurkat cells by simultaneously binding to SK-BR-3 cells with high expression HER2 and the Jurkat cells with high expression CD3, which means the heterodimer may recruit T cells to tumor cells, and result in improved cancer cell killing activity.

Example 10—In-Vitro Cytotoxicity of Heterodimeric Anti-HER2/Anti CD3-scFv Bispecific Antibody on Tumor Cells Target cells (BT-474 and SK-BR-3) were collected and resuspended in a complete medium (RPMI 1640, containing 10% FBS) with a cell density of $2\times10^5$ cells/mL. The target cells BT-474 and SK-BR-3 were seeded into the 96-well plates, 50 μL/well ($1\times10^4$ cells per well), respectively, and then serially diluted heterodimeric anti-HER2/anti-CD3-scFv samples and control with the complete medium were added at an amount of 100 μL/well. According to the pre-experiment, the effect v.s. target ratio (E/T) was determined as 20:1. The effector cells (human PBMC cells, Lonza, Cat. No. CC-2702) were resuspended in the complete medium with a cell density of $4\times10^6$ cell/mL, and then seeded 50 μL for each well ($2\times10^5$ cells per well). The culture plate was incubated for 4 days in a carbon dioxide incubator at 37° C. After incubation, the supernatant was removed and the cells were washed with 200 μL DPBS twice to scour off the effector cells. 100 μL the complete medium and 20 μLMTS were added, and then incubated in a carbon dioxide incubator at 37° C. for 2-3 hours. Absorbance was read at 490 nm (OD value) by microplate reader. Cytotoxicity was calculated as follows:

$$Cytotoxicity = \frac{ODcontrol - ODexperimental}{ODcontrol}$$

As shown in FIG. 11, the heterodimeric anti-HER2/anti-CD3-scFv construct killed the breast cancer cells SK-BR-3 and BT-474 with HER2 high expression in a concentration dependent manner. The cytotoxicity of the construct was far superior to HERCEPTIN® (HER2 mAb), showing a strong tumor cell killing activity.

Example 11—Pharmacokinetic Study of Heterodimeric Anti-HER2/Anti-CD3-scFv Bispecific Antibody in Mice A pharmacokinetic study of heterodimeric anti-HER2/anti-CD3-scFv was tested in 8-week-old female BALB/c mice, purchased from Beijing HFK Bioscience Co., Ltd. After one week for acclimation, the mice were randomly assigned into two groups with 21 mice in each group. Mice were injected intraperitoneally with a single dose of 20 nmol/kg of monoclonal antibody HERCEPTIN®, and heterodimeric anti-HER2/anti-CD3-scFv bispecific antibody respectively. Blood samples were collected by retro-orbital bleed into tubes without anticoagulant in a staggered manner at following time points:predose, 1, 3, 6, 10, 24, 48, 72, 96, 120, 168, 216, 264, 312 hr post administration. Each mouse was bled for two time points. The number of mice used for each time point was 2. The blood samples were allowed to clot for 30 min to 1 hr at room temperature, and centrifuged at 3000 rmp for 10 min, and then serum samples were harvested and stored at −80° C. for detection.

Serum samples were analyzed by ELISA to determine the concentrations of HERCEPTIN®, HER2/CD3 heterodimer therein. Briefly, a 96 well NuncMaxisorp assay plate was coated with 100 μL per well of recombinant human HER2 (Sino Biological, Cat. No: 10004-H08H) at 1 μg/mL in carbonate/bicarbonate buffer (pH9.6) overnight at 4° C. The plate was washed 5 times with PBST (Sigma, Cat. No: P-3563). 300 μL per well of 5% skim milk in PBST was added to block the plate and the plate was incubated for a minimum of 1 h at 25° C. The plate was washed as above, then 100 μL per well of serum samples diluted in 10% pooled mouse serum, 1% BSA in PBST was added to each well and the plate was incubated for 1 h at 25° C. The plate was washed as above and then 100 μL per well of anti-human IgG-HRP conjugate (Chemicon, Cat. No: AP309P) at 1:2000 dilution in 5% skim milk in PBST was added and incubated for 1 h at 25° C. The plate was washed as above and then 100 μL per well of TMB (BD OptEIA, Cat. No: 555214) was added and colorized for 10 min at room temperature. The reaction was stopped by the addition of 100 μL per well of 1 M $H_2SO_4$. The optical density at 450 nm was read using a microplate reader.

As shown in FIG. 12, heterodimeric anti-HER2/anti-CD3-scFv showed similar PK profile with HERCEPTIN® following single-dose intraperitoneal injection (20 nmol/kg) in mice. The pharmacokinetic parameters of heterodimeric anti-HER2/anti-CD3-scFv were as follows: half-life $t_{1/2}$ is 129 hours; $AUC_{last}$ is 30611 nM·hr; $T_{max}$ is 3 hours; $C_{max}$ is 264 nM; Vd is 85 mL/kg; CL is 0.45 mL/hr/kg; $MRT_{last}$ is 88 hours. A summary of the heterodimer production process for the anti-HER-2/Anti-CD3 construct is found in Table 5 below.

TABLE 5

| Table 5 | Her2/CD3 |
|---|---|
| Purity | 99.7% |
| Stability | Stable at least 7 days at 40° C. |
| Binding activity | HER2 MFI = 14.16 (Herceptin MFI = 20.55) |
|  | CD3 MFI = 5.19 (Bivalent Her2/CD3 MFI = 8.17) |
| Cell-to-cell association | Confirmed by SK-BR-3 and Jurkat cell association |

Example 12—Purification of Heterodimeric Anti-Trop-2/Anti-CD3-scFv Bispecific Antibody The harvested culture supernatant was purified as described in the example 5. The purified product was analyzed by SDS-PAGE. The result is shown in FIG. 13. The purity of the heterodimeric anti-Trop-2/anti-CD3-scFv product was above 95%.

Example 13—Stability and In Vitro Binding Activity of Heterodimeric Anti-Trop-2/Anti-CD3-scFv Bispecific Antibody Trop-2 binding activity of heterodimeric anti-Trop-2/anti-CD3-scFv constructs was tested by ELISA. Briefly, an ELISA plate was coated with 100 μL per well of recombinant human Trop-2 (Sino Biological, Cat. No: 10428-H08H) at 1 μg/mL in carbonate/bicarbonate buffer (pH 9.6) overnight at 4° C. The plate was washed 5 times with PBST. 300 μL per well of 1% BSA in PBST was added to block the plate and the plate was incubated for a minimum of 1 h at 25° C. The plate was washed as above, then 100 μL per well of samples diluted in 1% BSA in PBST was added to each well and the plate was incubated for 1 h at 25° C. The plate was washed as above and then 100 μL per well of anti-human IgG-HRP conjugate (Chemicon, Cat. No: AP309P) at 1:2000 dilution in 1% BSA in PBST was added and incubated for 1 h at 25° C. The plate was washed as above and then 100 μL per well of TMB (BD OptEIA, Cat. No: 555214) was added and colorized for 10 min at room temperature. The reaction was stopped by the addition of 100 μL per well of 1 M $H_2SO_4$. The optical density at 450 nm was read using a microplate reader. As shown in FIG. 14, the heterodimeric anti-Trop-2/anti-CD3-scFv construct possessed a high binding affinity to Trop-2.CD3 binding activity of heterodimeric anti-Trop-2/anti-CD3-scFv was tested using Jurkat cells with high expression CD3 by FACS. The FACS was performed as described in the example 8. As shown in Table 6, the heterodimeric anti-Trop-2/anti-CD3-scFv construct bound to Jurkat cells with high affinity, indicating it binds to its antigen CD3 with good activity.

TABLE 6

Binding activity to Jurkat cells with CD3 high expression

| Sample | MFI |
|---|---|
| Isotype | 3.34 |
| Anti-Trop-2 mAb | 3.10 |
| heterodimeric anti-Trop-2/anti-CD3-scFv | 17.51 |

Example 14—Simultaneous Binding Activity Against Trop-2 and CD3 of Heterodimeric Anti-Trop-2/Anti-CD3-scFv Bispecific Antibody Heterodimeric anti-Trop-2/anti-CD3-scFv was tested for simultaneous binding activity against Trop-2 and CD3 using BxPC3 cells and Jurkat cells by FACS. The FACS was performed as described in Example 9 above. BxPC3 cells were stained according to the operation instruction of PKH26 kits and Jurkat cells were stained by CFSE kit. As shown in FIG. 15, by simultaneous binding to BxPC3 cells with high expression Trop-2 and the Jurkat cells with high expression CD3, heterodimeric anti-Trop-2/anti-CD3-scFv can induce the association of BxPC3 and Jurkat cells, which means the heterodimer may recruit T cells to tumor cells, and result in improved cancer cell killing activity.

Example 15—In-Vitro Cytotoxicity of Heterodimeric Anti-Trop-2/Anti CD3-scFv Bispecific Antibody on Tumor Cells Target cells (H1650 and BxPC-3) were collected and resuspended in a complete medium (RPMI 1640, containing 10% FBS) with a cell density of $1\times10^5$ cells/mL. The target cells H1650 and BxPC-3 were seeded into 96-well plates, 50 μL/well ($5\times10^3$ cells per well), respectively, and then serially diluted heterodimeric anti-Trop-2/anti-CD3-scFv samples and control with the complete medium were added at an amount of 100 μL/well. The effector cells (human PBMC cells, Lonza, Cat. No. CC-2702) were resuspended in the complete medium with a cell density of $2\times10^6$ or $0.5\times10^6$ cells/mL, and then seeded 50 μL for each well ($1\times10^5$ or $0.25\times10^5$ cells per well). The culture plate was incubated for 3 days in a carbon dioxide incubator at 37° C. After incubation, the supernatant was removed, and cells were washed with 200 μL DPBS twice to scour off the effector cells. 100 μL the complete medium and 20 μLMTS were added, and the sample was incubated in a carbon dioxide incubator at 37° C. for 2-3 hours. Absorbance was read at 490 nm (OD value) by microplate reader. Cytotoxicity was calculated as follows:

$$Cytotoxicity = \frac{ODcontrol - ODexperimental}{ODcontrol}$$

As shown in FIG. 16 (with effector cells), the heterodimericanti-Trop-2/anti-CD3-scFv killed the Trop-2 high expression cancer cells (non-small-cell lung carcinoma cells H1650 and human pancreatic cancer cells BxPC-3) in a concentration dependent manner. The killing activity of the bispecific antibody was far superior to anti-Trop-2 mAb, showing a strong tumor cell killing activity.

Example 16—Pharmacokinetic Study of Heterodimeric Anti-Trop-2/Anti-CD3-scFv Bispecific Antibody in Mice A pharmacokinetic study of heterodimeric anti-Trop-2/anti-CD3-scFv was tested in 8-week-old female BALB/c mice, purchased from Beijing HFK Bioscience Co., Ltd. The injection, collection of blood sample and analytical method were performed as described in Example 11 above. Serum samples were analyzed by ELISA through coating with Trop-2 (Sino Biological, Cat. No: 10428-H08H) to determine the concentration of anti-Trop2/anti-CD3-scFv heterodimer therein. As shown in FIG. 17, the heterodimeric anti-Trop-2/anti-CD3-scFv showed a similar PK profile with anti-Trop-2 following single-dose intraperitoneal injection (20 nmol/kg) in mice. The pharmacokinetic parameters of heterodimeric anti-Trop-2/anti-CD3-scFv were as follows: half-life $t_{1/2}$ is 165 hours; $AUC_{last}$ is 26072 nM·hr; $T_{max}$ is 6 hours; $C_{max}$ is 203 nM; Vd is 107 mL/kg; CL is 0.45 mL/hr/kg; $MRT_{last}$ is 92 hours.

Example 17—Purification of Heterodimeric Anti-CD20/Anti-CD3-scFv Bispecific Antibody The harvested culture supernatant was purified as described in Example 5 above. The purified product was analyzed by SDS-PAGE. The result is shown in FIG. 18. The purity of the heterodimeric anti-CD20/anti-CD3-scFv product was above 95%.

Example 18—Stability and In Vitro Binding Activity of Heterodimeric Anti-CD20/Anti-CD3-scFv Bispecific Antibody The fully sealed heterodimeric anti-CD20/anti-CD3-scFv samples (1 mg/mL and 10 mg/mL) were stored in an incubator at 40° C. (BINDER, KBF240). Stability was tested with 20 sample at different time points (baseline (Day 0), Day 1, Day 3, Day 6) using high performance exclusion liquid chromatography (SEC-HPLC). As shown in FIG. 19, under experimental conditions at 40° C., there was not significant aggregation of the heterodimeric anti-CD20/anti-CD3-scFv. The data demonstrated that the heterodimeric anti-CD20/anti-CD3-scFv construct had good thermal stability. CD20 and CD3 binding activity of heterodimeric anti-CD20/anti-CD3-scFv was tested using Raji cells (having high expression of CD20) and Jurkat cells (having high expression of CD3) by FACS. The FACS was performed as described in the Example 8 above. As shown in Table 7 and Table 8, the heterodimeric anti-CD20/anti-CD3-scFv construct bound to Raji cells and Jurkat cells, which indicated the construct bound to both antigens CD20 and CD3.

TABLE 7

Binding activity to Raji cells with CD20 high expression

| Sample | MFI |
| --- | --- |
| Isotype | 2.77 |
| heterodimeric anti-CD20/anti-CD3-scFv | 7.28 |

TABLE 8

Binding activity to Jurkat cells with CD3 high expression

| Sample | MFI |
| --- | --- |
| Isotype | 2.75 |
| heterodimeric anti-CD20/anti-CD3-scFv | 5.61 |

Example 19—Purification of Heterodimeric Anti-PD-L1/Anti-CD3-scFv Bispecific Antibody Harvested culture supernatant was purified as described in the Example 5 above. The purified product was analyzed by SDS-PAGE. The result is shown in FIG. 20. The purity of the heterodimeric anti-PD-L1/anti-CD3-scFv product was above 95%.

Example 20—In-Vitro Binding Activity of Heterodimeric Anti-PD-L1/Anti-CD3-scFv Bispecific Antibody PD-L1 binding activity of the heterodimeric anti-PD-L1/anti-CD3-scFv construct was tested by ELISA. The ELISA was performed as described in Example 13 above. The ELISA plate was coated with PD-L1 (Sino Biological, Cat. No. 10084-H08H). As shown in FIG. 21, the heterodimeric anti-PD-L1/anti-CD3-scFv has high binding affinity to PD-L1.

CD3 binding activity of heterodimeric anti-PD-L1/anti-CD3-scFv was tested using Jurkat cells (having high expression CD3) by FACS. The FACS was performed as described in Example 8 above. As shown in Table 9, the heterodimeric anti-PD-L1/anti-CD3-scFv bound to Jurkat cells, which indicated it bound to its antigen CD3.

TABLE 9

Binding activity to Jurkat cells with CD3 high expression

| Sample | MFI |
| --- | --- |
| Isotype | 2.70 |
| heterodimeric anti-PD-L1/anti-CD3-scFv | 8.90 |

Example 21—Simultaneous Binding Activity Against PD-L1 and CD3 of Heterodimeric Anti-PD-L1/Anti-CD3-scFv Bispecific Antibody Heterodimeric anti-PD-L1/anti-CD3-scFv was tested for simultaneous binding activity against PD-L1 and CD3 using H460 cells and Jurkat cells by FACS. The process was performed as described in Example 9 above. As shown in FIG. 22, the heterodimeric anti-PD-L1/anti-CD3-scFv construct can induce the association of H460 cells (having high expression of PD-L1) and Jurkat cells (having high expression of CD3), which means the heterodimer may recruit T cells to tumor cells, and result in improved cancer cell killing activity.

Example 22—In-Vitro Cytotoxicity of Heterodimeric Anti-PD-L1/Anti CD3-scFv Bispecific Antibody Target cells (H1650 and HCC827) were collected and resuspended in the complete medium RPMI 1640 (10% FBS) at a cellular density of $1 \times 10^5$ cells/mL. The target cells H1650 and HCC827 were seeded into the 96-well plates at an amount of 50 μL/well (5×10³ cells per well), and then serially diluted heterodimeric anti-PD-L1/anti-CD3-scFv samples and control with the complete medium was added at an amount of 100 μL/well. The effector cells (human PBMC cells, Lonza, Cat. No. CC-2702) were resuspended in the complete medium at a cellular density of 2×10⁶ cell/mL, and then seeded at 50 μL for each well (1×10⁵ cells per well). The culture plate was incubated for 3 days in a carbon dioxide incubator at 37° C. After incubation, the supernatant was removed, and the cells were washed with 200 μL DPBS twice to scour off the effector cells. 100 μL the complete medium and 20 μL MTS were added to the sample, which was then incubated in a carbon dioxide incubator at 37° C. for 2-3 hours. Absorbance was read at 490 nm (OD value) by microplate reader. Cytotoxicity was calculated as follows:

$$\text{Cytotoxicity} = \frac{OD\text{control} - OD\text{experimental}}{OD\text{control}}$$

As shown in FIG. 23 (with effector cells), the heterodimeric anti-PD-L1/anti-CD3-scFv construct killed the PD-L1 high expression cancer cells (non-small-cell lung carcinoma cells H1650 and HCC827) in a concentration dependent manner, showing a strong tumor cell killing activity.

Example 23—Purification of Anti-Her2 and Anti-CD20 Expression Products for Production of Fab-Fab Format Bispecific Antibody An AKTA explorer 100 system (GE Healthcare) with the affinity chromatographic column Protein A SEPHAROSE® Fast Flow (16 mm I.D. 22 mL GE Healthcare) was used for purification at 4° C. The column was initially equilibrated using Buffer A (20 mM PBST; 150 mM NaCl, pH 7.4) wherein the cell supernatant was loaded after the base line was steady at a flow speed of 5 mL/min, and then equilibration was carried out using buffer A. The samples were anti-Her2 and anti-CD20 expression products with amino acid mutations in the CH3 domains, expressed by the methods described in Example 4 above. Next, the column was rinsed with 5× column volume of buffer B1 (buffer A+0.5M Arg) and then was eluted with 5× column volume of buffer B2 (100 mM citric acid, pH 3.0), to collect the eluted peak, which is the desired protein. The flow speed of the elution step was 5 mL/min. The representative chromatogram for the anti-CD20 product is shown in FIG. 24, with the anti-Her2 product yielding similar results (unshown). The elution peak marked in gray was collected and 1 M sodium acetate was added to adjust pH to 5.0.

Example 24—Purification of Anti-Her2/Anti-CD20 Natural IgG-Like Heterodimeric Bispecific Antibody The generic structure of the anti-Her2/anti-CD20 heterodimer is shown in FIG. 25.

The purified products of Example 23 were re-assembled ex vivo to form heterodimers. First, the buffer was changed to phosphate buffered saline (PBS) using ultrafiltration concentration (10 kDa molecular-weight cut-off). The concentrations of each of the anti-Her2 and anti-CD20 products were adjusted to 1 mg/mL in PBS, and 1/200 volume of 1 M dithiothreitol (DTT) was added (the final concentration of DTT was 0.1 mM, 0.5 mM, 1 mM, 2 mM, 5 mM, 10 mM, or 20 mM). This was followed by reduction at 4° C. for 3-8 hours. During this reduction step, disulfide bonds, such as those in the hinge region of homodimers that may be present among the anti-Her2 and anti-CD20 expression products open up, leading to the formation of half antibodies (or halfmers) with one light chain and one heavy chain as shown in FIG. 26. The sample after the reduction step was analyzed by SDS-PAGE under denaturing conditions. The representative results for the anti-CD20 product are shown in FIG. 27, with the anti-Her2 product yielding similar results (unshown). In the figure, the four major bands present in lanes 2-4 from the right side are from top to bottom: LC—HC—HC-LC homodimer, HC-LC halfmer, HC, and LC, respectively. As shown in the figure, as DTT concentration increased, only two bands (HC and LC) appeared prominent and virtually no homodimers were observable. The result by analysis of SEC-HPLC in the presence of 1 mM DTT in PBS is shown in FIG. 28 for the anti-Her2 half product (A) and anti-CD20 half product (B). As shown in FIG. 28, when the concentration of DTT was equal to or above 1 mM, both anti-Her2 and anti-CD20 products had the proportion of homodimers below 10%, and the proportion of half antibody molecules (halfmers) above 90% by weight of the total polypeptidyl species concerned.

The reduced anti-Her2 and anti-CD20 halfmers were then mixed in a 1:1 (molar ratio), and re-assembled at 4° C. for 0.5-24 hour. During this reassembly process, the anti-Her2 and anti-CD20 halfmers formed the anti-Her2/anti-CD20 heterodimer that contain both halfmers held mostly together by non-covalent interactions between CH2/CH3. Afterwards, the buffer was changed to PBS using ultrafiltration concentration (10 kDa molecular-weight cut-off). The reduced state was terminated by air or oxidant-driven oxidation to form the inter-chain disulfide bonds of the heterodimeric bispecific antibody. Oxidation conditions included exposing to air for 1 day, 3 days, 4 days, or with the addition of the oxidant100 mM L-dehydroascorbic acid (the final protein concentration was 1 mg/mL, and the final oxidant concentration was 0.5 mM, 1 mM, 5 mM or 10 mM) at 4° C. and incubating for 5 or 24 hours. After oxidation, the product was analyzed by SDS-PAGE. The result is shown in FIG. 29.

Using ultrafiltration concentration (10 kDa molecular-weight cut-off), the above anti-Her2/anti-CD20 heterodimer obtained from reduction-oxidation of anti-Her2 and anti-CD20 halfmers, was concentrated and the buffer composition was changed into 10 mM PBST, pH5.8). The AKTA explorer 100 system (GE Healthcare) with the ion exchange chromatographic column Source 15S (16 mm I.D., 17 mL, GE Healthcare) was used to purify samples at 4° C. The column was initially equilibrated using Buffer A (10 mM Na₃PO₄, pH7.0), wherein the protein solution treated as mentioned above was loaded after the base line was steady at a flow speed of 3 mL/min, and then equilibration was carried out using Buffer A. Next, using a gradient from Buffer A (10 mM Na₃PO₄, pH7.0) to Buffer B (10 mM Na₃PO₄, pH5.8), the column was rinsed with 20 column volumes (0% B-100% B in 170 mins, flowspeed 2 mL/min). The main elution peak as marked was collected (shown in FIG. 30). The collected protein solution was concentrated and its buffer composition changed again to PBS (pH 7.4) using ultrafiltration tube (10 kDa molecular-weight cut-off) and sterile filtered at 4° C. for preservation. The purified product was analyzed by SDS-PAGE. The result is shown in FIG. 31. The product was also analyzed by SEC-HPLC, result shown in FIG. 32. The purity was 97.3%.

Example 25—Setting Up Analysis Method for Anti-HER2/Anti-CD20 Heterodimer

The following five samples were identified by HPLC: anti-HER2 half antibody, anti-HER2 homodimer, anti-CD20 half antibody, anti-CD20 homodimer, and anti-HER2/anti-CD20 heterodimer. The experimental details were as follows: (1) hydrophobic interaction chromatographic column (TSK-GEL Phenyl-5PW, 7.5 mm ID×7.5 cm, 10 μm); (2) Mobile phase and gradient: bufferA: 20 mM PBS, pH 7.0, 1 M $(NH_4)_2SO_4$; bufferB: 20 mM PBS, pH 7.0; the gradient ran from 40% buffer B-100% buffer B in 40 minutes; (3) Flow speed: 0.5 mL/min; (4) temperature: 25° C.; (5) detection wavelength: 280 nm. As can be readily observed from the results shown in FIG. 33, anti-CD20-Fc1 homodimer (peak1 in FIG. 33), anti-HER2-Fc2 homodimer (peaks in FIG. 33) and anti-HER2/anti-CD20 heterodimer (peak3 in FIG. 33) could be effectively distinguished through different retention times using this method. This confirmed the product of Example 24 is a heterodimer, and not a homodimer.

Example 26—Anti-HER2/Anti-CD20 Heterodimer Identification by Mass Spectra

The three following samples of anti-HER2 homodimer, anti-CD20 homodimer, and anti-HER2/anti-CD20 heterodimer were analyzed by LC-MS method to test the amino acid coverage. The above samples were digested by trypsin and incubated at 37° C. for 18 hours. The LC-MS conditions were as follows: column:WatersACQUITY UPLC BEH C18, 300 Å, 1.7 μm, 2.1 mm×100 mm. Column Temperature: 50° C. FlowSpeed: 0.2 mL/min. Buffer A: 0.1% formic acid. Buffer B: 0.1% formic acid/100% acetonitrile. Elution Gradient: 2-35% buffer B in 90 mins; 35-45% Buffer B in 20 mins. ESI source: positive ion mode. Capillary voltage: 2.5 kV. Cone voltage: 25V. Scan scope: 100-2500 Da. $MS^e$ voltage: 20-40V.

FIG. 34A and FIG. 34B show the base peak ion chromatogram (BPI) of anti-HER2 homodimer, anti-CD20 homodimer and anti-HER2/anti-CD20 heterodimer (FIG. 34A), along with the amino acid coverage for each sample (FIG. 34B). The coverage of anti-CD20 homodimer was 99.7%, anti-HER2 homodimer was 100%, anti-HER2/anti-CD20 heterodimer was 99.4%. The amino acid sequences of anti-CD20 light chain and heavy chain comprising two specific amino acid substitutions in anti-CD20 homodimer obtained from LC-MS were shown in SEQ ID NO: 73 and 74, respectively. The amino acid sequences of anti-HER2 light chain and heavy chain comprising three specific amino acid substitutions in anti-HER2 homodimer obtained from LC-MS were shown in SEQ ID NO: 75 and 76, respectively. The amino acid sequences of anti-CD20 light chain and heavy chain comprising two specific amino acid substitutions in anti-CD20/HER2 heterodimer obtained from LC-MS were shown in SEQ ID NO: 77 and 78, respectively. The amino acid sequences of anti-HER2 light chain and heavy chain comprising three specific amino acid substitutions in anti-CD20/HER2 heterodimer obtained from LC-MS were shown in SEQ ID NO: 79 and 80, respectively. The amino acid glycine at position 66 and lysine at position 67 in SEQ ID NO: 74, the amino acid glysine at position 66, lysine at position 67, lysine at position 218, alanine at position 343, lysine at position 344 in SEQ ID NO: 78, and the amino acid lysine at position 217, alanine at position 342, lysine at position 343 in SEQ ID NO: 80 were not found in LC-MS analysis. The results indicated that the anti-HER2/anti-CD20 heterodimer had the same sequence as expected.

It will be understood by those of skill in the art that numerous and various modifications can be made without departing from the scope and spirit of the present disclosure. Therefore, it should be understood that various embodiments of the invention described herein are illustrative only and not intended to limit the scope of the invention. All references cited herein are hereby incorporated by reference in their entirety.

---

The invention claimed is:

1. A heterodimer comprising an Fc receptor (FcR)-binding member and one or more recognition moieties covalently linked to the FcR-binding member,
   wherein said FcR-binding member comprises an Fc domain mutant, said Fc domain mutant comprising a first polypeptide and a second polypeptide joined to each other by one or more disulfide bonds, and
   wherein the one or more recognition moieties covalently linked to the N-terminus or the C-terminus of the first polypeptide and/or the second polypeptide, and
   wherein the first polypeptide and the second polypeptide each comprises an immunoglobulin G (IgG) CH3 domain mutant with amino acid substitutions of any one of the following a)-h):
   a) T366L and D399R in the first polypeptide and L351E, Y407L and K409V in the second polypeptide;
   b) T366L and D399C in the first polypeptide and L351G, Y407L and K409C in the second polypeptide;
   c) T366L and D399C in the first polypeptide and L351Y, Y407A and K409P in the second polypeptide;
   d) T366P and D399N in the first polypeptide and L351V, Y407P and K409S in the second polypeptide;
   e) T366W and D399G in the first polypeptide and L351D, Y407P and K409S in the second polypeptide;
   f) T366P and D399I in the first polypeptide and L351P, Y407F and K409F in the second polypeptide;
   g) T366V and D399T in the first polypeptide and L351K, Y407T and K409Q in the second polypeptide; and
   h) T366L and D399A in the first polypeptide and L351W, Y407H and K409R in the second polypeptide wherein amino acid positions in the a)-h) are according to Kabat EU index.

2. The heterodimer of claim 1, wherein Fc domain of the Fc domain mutant comprises one selected from the group consisting of an IgG1 Fc domain, an IgG2 Fc domain, an IgG3 Fc domain, and an IgG4 Fc domain.

3. The heterodimer of claim 1, wherein the one or more recognition moieties comprise at least one of fragment antigen-binding (Fab) fragments, single chain variable (scFv) fragments, extracellular domains of membrane receptors, peptide ligands of cell membrane receptors, cytokines, coagulation factors, affinity tags, and combinations thereof.

4. The heterodimer of claim 3, wherein the one or more recognition moieties comprise two recognition moieties, and wherein the two recognition moieties comprise a Fab fragment and a scFv fragment.

5. The heterodimer of claim 4, wherein the Fab fragment and the scFv fragment are selected from a pair of recognition moieties selected from the following a)-d):
   a) Fab specifically binding to HER2 and scFv specifically binding to CD3;
   b) Fab specifically binding to Trop2 and scFv specifically binding to CD3;
   c) Fab specifically binding to CD20 and scFv specifically binding to CD3; and
   d) Fab specifically binding to PD-L1 and scFv specifically binding to CD3.

6. The heterodimer of claim 3, wherein the one or more recognition moieties comprise two recognition moieties, and wherein the two recognition moieties each comprise Fab fragments.

7. The heterodimer of claim 6, wherein the two Fab fragments are non-identical.

8. The heterodimer of claim 7, wherein the two non-identical Fab fragments comprise a first Fab fragment that specifically binds to HER2 and a second Fab fragment that specifically binds to CD20.

9. The heterodimer of claim 7, wherein the heterodimer comprises an immunoglobulin-like molecule.

10. The heterodimer of claim 7, wherein the heterodimer comprises a bispecific antibody.

11. The heterodimer of claim 1, wherein less than 50% by weight of each of the first and second polypeptides and the recognition moiety of said first or second polypeptide exist in a homodimeric form, when present in an aqueous solution under physiological conditions containing 1 mM dithiothreitol, based on the weight of all polypeptidyl forms in the solution, provided that said solution is essentially free of polypeptides other than said first or second polypeptide and the recognition moiety thereof.

12. The heterodimer of claim 1, wherein the substitutions comprise T366L and D399R in the first polypeptide and L351E, Y407L and K409V in the second polypeptide.

13. The heterodimer of claim 1, wherein one of the first polypeptide and the second polypeptide comprises the amino acid sequence of SEQ ID NOs: 16, 18, 20, 22, 24, 26, 28, or 30, and the other polypeptide comprises the amino acid sequence of SEQ ID NOs: 17, 19, 21, 23, 25, 27, 29, or 31.

14. The heterodimer of claim 1, wherein the FcR-binding member binds to an Fc receptor selected from the group consisting of FcγRI, FcγRIIA, FcγRIIB1, FcγRIIB2, FcγRIIIA, FcγRIIIB, FcεRI, FcεRII, FcαRI, Fcα/μR, FcRn, and combinations thereof.

15. The heterodimer of claim 14, wherein the FcR-binding member binds to FcRn.

16. The heterodimer of claim 14, wherein binding to the Fc receptor triggers ADCC.

17. A pharmaceutical composition comprising
a pharmaceutically acceptable carrier and
one of the following i)-v):
  i) the heterodimer of claim 1;
  ii) a nucleic acid encoding at least one of the first polypeptide and the second polypeptide of claim 1;
  iii) a vector or vectors comprising the nucleic acid of ii);
  iv) a cell of comprising the vector or vectors of (iii); and
  v) a combination thereof.

18. A heterodimer comprising a first heavy chain and a second heavy chain, and a first light chain and a second light chain, wherein the first heavy chain and the second heavy chain are non-identical, and wherein the first light chain and the second light chain are non-identical,
wherein the first heavy chain and the second heavy chain polypeptide each comprises an immunoglobulin G (IgG) CH3 domain mutant with amino acid substitutions of any one of the following a)-h):
  a) T366L and D399R in the first heavy chain and L351E, Y407L and K409V in the second heavy chain;
  b) T366L and D399C in the first heavy chain and L351G, Y407L and K409C in the second heavy chain;
  c) T366L and D399C in the first heavy chain and L351Y, Y407A and K409P in the second heavy chain;
  d) T366P and D399N in the first heavy chain and L351V, Y407P and K409S in the second heavy chain;
  e) T366W and D399G in the first heavy chain and L351D, Y407P and K409S in the second heavy chain;
  f) T366P and D399I in the first heavy chain and L351P, Y407F and K409F in the second heavy chain;
  g) T366V and D399T in the first heavy chain and L351K, Y407T and K409O in the second heavy chain; and
  h) T366L and D399 Å in the first heavy chain and L351W, Y407H and K409R in the second heavy chain,
wherein amino acid positions in the a)-h) are according to Kabat EU index.

19. A method of producing the heterodimer of claim 1 comprising
  1) expressing one or more nucleic acids encoding the first polypeptide in a first host cell and one or more nucleic acids encoding the second polypeptide in a second host cell, the first host cell and the second host cell being separated from one another;
  2) reducing the first polypeptide and the second polypeptides while separated;
  3) combining the first polypeptide and the second polypeptide to form a resultant mixture;
  4) oxidizing the resultant mixture; and
  5) recovering the formed heterodimer.

20. The method of claim 19, wherein the one or more nucleic acids are contained within a vector or system of vectors.

21. The method of claim 20, wherein the vector or system of vectors comprises plasmid vectors pX0GC modified from pCDNA vectors.

22. The method of claim 21, wherein the vector or system of vectors are introduced into a cell or cells.

23. The method of claim 22, wherein the cell or cells comprises one of HEK293, HEK293T, HEK293F or CHO, CHO—S, CHO-dhfr-, CHO/DG44 and ExpiCHO cells.

24. The method of claim 19, wherein the reducing step comprises:
  i) adding a reductant, wherein the reductant comprises one of 2-aminoethanethiol, dithiothreitol (DTT), three (2-carboxyethyl) phosphine, derivatives thereof, and combinations thereof;
  ii) reducing for at least about 3 hours at about 4° C.; and
  iii) removing the reductant.

25. The method of claim 24, wherein the reductant comprises DTT at a concentration of about 0.1 mM or higher.

26. The method of claim 24, wherein the reductant is removed via a desalting column.

27. The method of claim 19, wherein the oxidizing step comprises oxidizing by air for at least about 5 hours.

28. The method of claim 19, wherein the oxidizing step comprises:
  i) addition of an oxidant comprising L-dehydroascorbic acid, its derivatives, or combinations thereof
  ii) oxidizing for at least about 5 hours at about 4° C.; and
  iii) removing the oxidant.

29. The method of claim 28, wherein the oxidant comprises L-dehydroascorbic acid at a concentration of about 0.5 mM or higher.

30. The method of claim 19, further comprising a separation step.

31. A method of producing the heterodimer of claim 18, comprising:
  1) expressing one or more nucleic acids encoding the first heavy chain and the first light chain in a first host cell and one or more nucleic acids encoding the second heavy chain and the second light chain in a second host cell, the first host cell and the second host cell being separated from one another;
  2) reducing the first heavy chain and first light chain together and the second heavy chain and second light chain together;

3) combining the first heavy chain, first light chain, second heavy chain, and second light chain to form a resultant mixture;
4) oxidizing the resultant mixture; and
5) recovering the formed heterodimer,
wherein the Fc region comprises at least five amino acid substitutions, the at least five amino acid substitutions comprising any one of the following a)-h):
a) T366L and D399R in the first heavy chain and L351E, Y407L and K409V in the second heavy chain;
b) T366L and D399C in the first heavy chain and L351G, Y407L and K409C in the second heavy chain;
c) T366L and D399C in the first heavy chain and L351Y, Y407A and K409P in the second heavy chain;
d) T366P and D399N in the first heavy chain and L351V, Y407P and K409S in the second heavy chain;
e) T366W and D399G in the first polypeptide and L351D, Y407P and K409S in the second heavy chain;
f) T366P and D399I in the first polypeptide and L351P, Y407F and K409F in the second heavy chain
g) T366V and D399T in the first heavy chain and L351K, Y407T and K409Q in the second heavy chain; and
h) T366L and D399 Å in the first heavy chain and L351W, Y407H and K409R in the second heavy chain,
wherein amino acid positions in the a)-h) are according to Kabat EU index.

32. A nucleic acid encoding at least one of the first polypeptide and the second polypeptide of claim 1.

33. The nucleic acid of claim 32, wherein the nucleic acid comprises at least one of SEQ ID NOs: 32, 34, 36, 38, 40, 42, 44, 46, 47, 50, 52, 54, 56, 58, 60, 62 and 64-67.

34. A vector or system of vectors comprising the nucleic acid of claim 32.

35. The vector or system of vectors of claim 34, wherein the vector or system of vectors comprise plasmid vectors pX0GC modified from pCDNA vectors.

36. A cell comprising the vector or system of vectors of claim 34.

37. The cell of claim 36, wherein the cell comprises one of HEK293, HEK293T, HEK293F or CHO, CHO—S, CHO-dhfr-, CHO/DG44 and ExpiCHO cells.

* * * * *